United States Patent
Stephanopoulos et al.

(10) Patent No.: US 10,064,885 B2
(45) Date of Patent: Sep. 4, 2018

(54) METABOLIC GENE, ENZYME, AND FLUX TARGETS FOR CANCER THERAPY

(75) Inventors: Gregory Stephanopoulos, Winchester, MA (US); Christian M. Metallo, San Diego, CA (US); Joanne K. Kelleher, Cambridge, MA (US); Othon Iliopoulos, Cambridge, MA (US); Paulo Alexandre da Costa Gameiro Guerreiro, Cambridge, MA (US)

(73) Assignees: Massachusetts Institute of Technology, Cambridge, MA (US); The General Hospital Corporation, Boston, MA (US)

( * ) Notice: Subject to any disclaimer, the term of this patent is extended or adjusted under 35 U.S.C. 154(b) by 239 days.

(21) Appl. No.: 13/809,333

(22) PCT Filed: Jul. 8, 2011

(86) PCT No.: PCT/US2011/043324
§ 371 (c)(1),
(2), (4) Date: Aug. 23, 2013

(87) PCT Pub. No.: WO2012/006506
PCT Pub. Date: Jan. 12, 2012

(65) Prior Publication Data
US 2013/0331432 A1    Dec. 12, 2013

Related U.S. Application Data

(60) Provisional application No. 61/363,192, filed on Jul. 9, 2010, provisional application No. 61/434,094, filed on Jan. 19, 2011.

(51) Int. Cl.
| | |
|---|---|
| *C12N 15/11* | (2006.01) |
| *A61K 31/713* | (2006.01) |
| *C12N 15/113* | (2010.01) |
| *A61K 31/194* | (2006.01) |
| *A61K 31/433* | (2006.01) |
| *A61K 31/655* | (2006.01) |
| *A61K 45/06* | (2006.01) |

(52) U.S. Cl.
CPC .......... *A61K 31/713* (2013.01); *A61K 31/194* (2013.01); *A61K 31/433* (2013.01); *A61K 31/655* (2013.01); *A61K 45/06* (2013.01); *C12N 15/1137* (2013.01); *C12Y 101/01041* (2013.01); *C12N 2310/14* (2013.01); *C12N 2310/531* (2013.01)

(58) Field of Classification Search
CPC ...... A61K 31/713; C12Q 1/6886; C12Q 1/32; C12N 2310/14; C12N 15/1137; C12N 15/1135; C12Y 101/01042
See application file for complete search history.

(56) References Cited

U.S. PATENT DOCUMENTS

2008/0300208 A1* 12/2008 Einat et al. ............ 514/44
2012/0121515 A1*  5/2012 Dang ............. C12Y 101/01042
                                                424/9.3

FOREIGN PATENT DOCUMENTS

| EP | 0 656 210 A1 | 6/1995 |
| WO | WO 2008/024858 A2 | 2/2008 |
| WO | WO 2011143160 A2 * | 11/2011 |

OTHER PUBLICATIONS

Zhao et al, Glioma-Derived Mutations in IDH1 Dominantly Inhibit IDH1 Catalytic Activity and Induce HIF-1a, Apr. 10, 2009, Science, vol. 324, pp. 261-265.*
Seltzer et al, Inhibition of Glutaminase Preferentially Slows Growth of Glioma Cells with Mutant IDH1, published online Nov. 2, 2010, Cancer Research, vol. 70, 22: 8981-8987.*
Lobo et al, Inhibition of glutaminase expression by antisense mRNA decreases growth and tumourigenicity of tumour cells, 2000, Biochem J., 348: 257-261.*
Bratslavsky et al, Pseudohypoxic Pathways in Renal Cell Carcinoma, 2007, Clin. Cancer Res., v.13, 16: 4667-4671.*
Dang et al., Cancer-associated IDH1 mutations produce 2-hydroxyglutarate. Nature. Dec. 10, 2009;462(7274):739-44. doi: 10.1038/nature08617.
Erdmann et al., Glutamate production by HIV-1 infected human macrophage is blocked by the inhibition of glutaminase J Neurochem. Jul. 2007;102(2):539-49.
Holleran et al., Glutamine metabolism in AS-30D hepatoma cells. Evidence for its conversion into lipids via reductive carboxylation. Mol Cell Biochem. Nov. 22, 1995;152(2):95-101.
Jones et al., Tumor suppressors and cell metabolism: a recipe for cancer growth. Genes Dev. Mar. 1, 2009;23(5):537-48. doi: 10.1101/gad.1756509.
Kil et al., Small interfering RNA-mediated silencing of mitochondrial NADP+-dependent isocitrate dehydrogenase enhances the sensitivity of HeLa cells toward tumor necrosis factor-alpha and anticancer drugs. Free Radic Biol Med. Oct. 15, 2007;43(8):1197-207. Epub Jul. 20, 2007.

(Continued)

*Primary Examiner* — Ekaterina Poliakova-Georgantas
(74) *Attorney, Agent, or Firm* — Wolf, Greenfield & Sacks, P.C.

(57) ABSTRACT

A novel pathway in cancer cell metabolism is identified. Targeting of any gene, protein, or enzyme that modulates activity or flux through this pathway, including, but not limited to IDH1, isocitrate dehydrogenase 2 (IDH2), aconitase 1 (ACO1), aconitase 2 (ACO2), glutaminase (GLS), glutamate dehydrogenase (GDH) and transaminase, provides effective means of inhibiting tumor growth.

5 Claims, 47 Drawing Sheets

Specification includes a Sequence Listing.

(56) References Cited

OTHER PUBLICATIONS

Mecinović et al., 2-Oxoglutarate analogue inhibitors of prolyl hydroxylase domain 2. Bioorg Med Chem Lett. Nov. 1, 2009;19(21):6192-5. doi: 10.1016/j.bmcl.2009.09.005. Epub Sep. 6, 2009.

Metallo et al., Analyzing Cancer as a Metabolic Disease Using 13C Metabolic Flux Analysis to Decipher Pathway Regulation. AICHE. 2010 Annual Meeting. Nov. 11, 2010. Abstract.

Metallo et al., Evaluation of 13C isotopic tracers for metabolic flux analysis in mammalian cells. J Biotechnol. Nov. 2009;144(3):167-74. doi: 10.1016/j.jbiotec.2009.07.010. Epub Jul. 19, 2009.

Murugan et al, Identification and functional characterization of isocitrate dehydrogenase 1 (IDH1) mutations in thyroid cancer. Biochem Biophys Res Commun. Mar. 12, 2010;393(3):555-9. doi: 10.1016/j.bbrc.2010.02.095. Epub Feb. 18, 2010.

Reitman et al., Isocitrate dehydrogenase 1 and 2 mutations in cancer: alterations at a crossroads of cellular metabolism. J Natl Cancer Inst. Jul. 7, 2010;102(13):932-41. doi: 10.1093/jnci/djq187. Epub May 31, 2010.

Ward et al., The common feature of leukemia-associated IDH1 and IDH2 mutations is a neomorphic enzyme activity converting alpha-ketoglutarate to 2-hydroxyglutarate. Cancer Cell. Mar. 16, 2010;17(3):225-34. doi: 10.1016/j.ccr.2010.01.020. Epub Feb. 18, 2010.

Bardella et al., SDH mutations in cancer. Biochim Biophys Acta. Nov. 2011;1807(11):1432-43. doi: 10.1016/j.bbabio.2011.07.003.

Bayley et al., Warburg tumours and the mechanisms of mitochondrial tumour suppressor genes. Barking up the right tree? Curr Opin Genet Dev. Jun. 2010;20(3):324-9. doi: 10.1016/j.gde.2010.02.008.

Cardaci et al., TCA cycle defects and cancer: when metabolism tunes redox state. Int J Cell Biol. 2012;2012:161837. doi: 10.1155/2012/161837.

Carvajal-Carmona et al., Adult Leydig cell tumors of the testis caused by germline fumarate hydratase mutations. J Clin Endocrinol Metab. Aug. 2006;91(8):3071-5.

King et al., Succinate dehydrogenase and fumarate hydratase: linking mitochondrial dysfunction and cancer. Oncogene. Aug. 7, 2006;25(34):4675-82.

Launonen et al., Inherited susceptibility to uterine leiomyomas and renal cell cancer. Proc Natl Acad Sci U S A. Mar. 13, 2001;98(6):3387-92

Lehtonen et al., Increased risk of cancer in patients with fumarate hydratase germline mutation. J Med Genet. Jun. 2006;43(6):523-6.

Mackenzie et al., Cell-permeating alpha-ketoglutarate derivatives alleviate pseudohypoxia in succinate dehydrogenase-deficient cells. Mol Cell Biol. May 2007;27(9):3282-9.

Pollard et al., Accumulation of Krebs cycle intermediates and over-expression of HIF1alpha in tumours which result from germline FH and SDH mutations. Hum Mol Genet. Aug. 1, 2005;14(15):2231-9.

Pollard et al., The TCA cycle and tumorigenesis: the examples of fumarate hydratase and succinate dehydrogenase. Ann Med. 2003;35(8):632-9.

Spinella et al., Endothelin-1 inhibits prolyl hydroxylase domain 2 to activate hypoxia-inducible factor-1alpha in melanoma cells. PLoS One. Jun. 21, 2010;5(6):e11241. doi: 10.1371/journal.pone.0011241.

Teicher et al., Targeting cancer metabolism. Clin Cancer Res. Oct. 15, 2012;18(20):5537-45. doi: 10.1158/1078-0432.CCR-12-2587.

Tomlinson et al., Germline mutations in FH predispose to dominantly inherited uterine fibroids, skin leiomyomata and papillary renal cell cancer. Nat Genet. Apr. 2002;30(4):406-10.

* cited by examiner

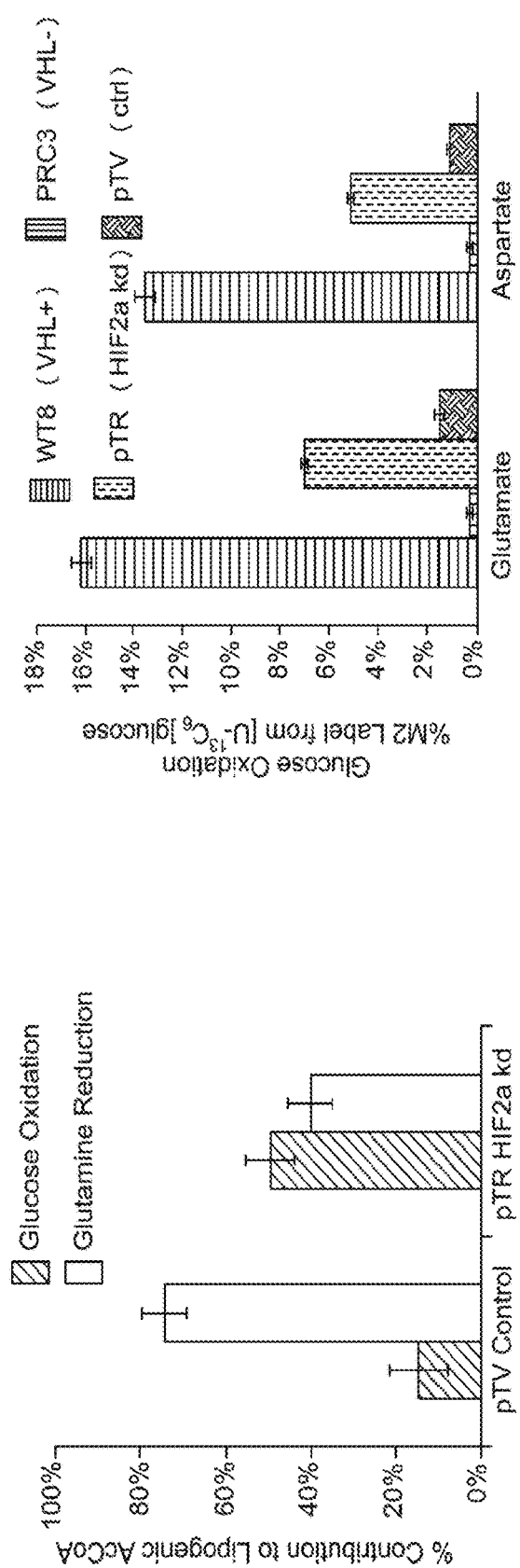
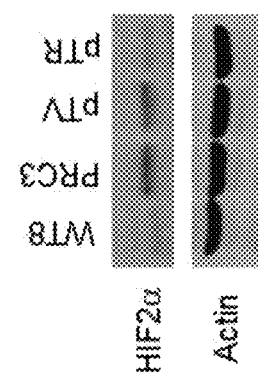
FIG. 5E, FIG. 5F, FIG. 5G

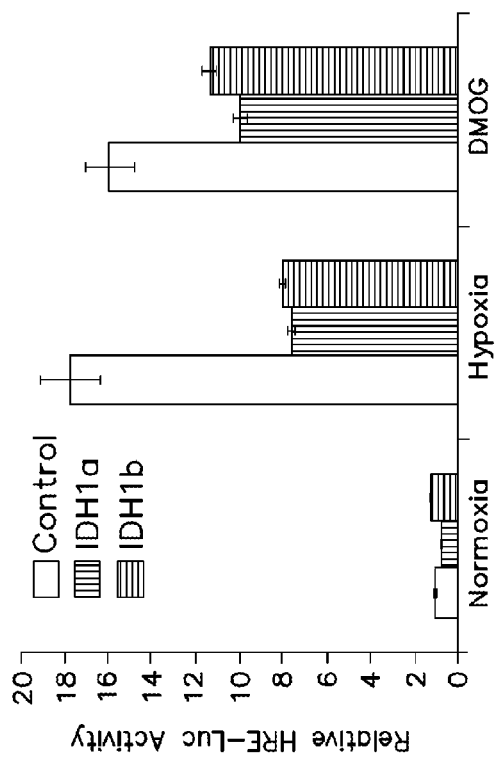
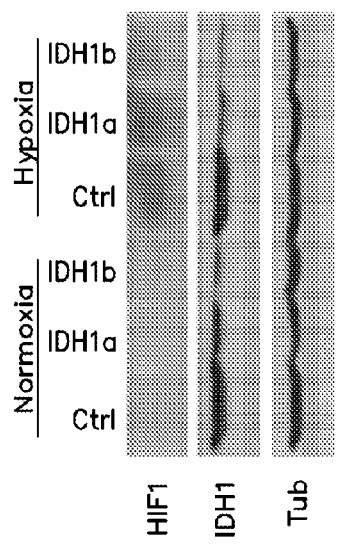
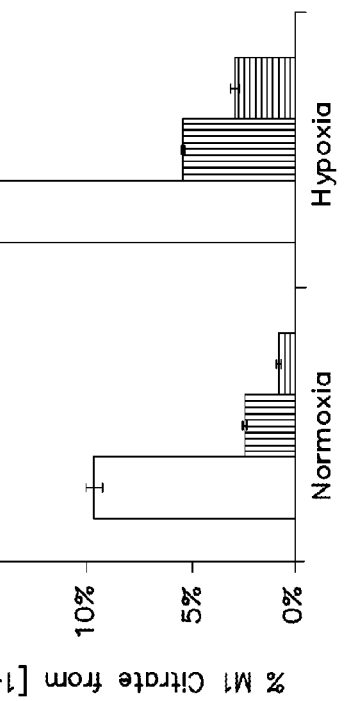
FIG. 17A
FIG. 17B
FIG. 17C
FIG. 17D

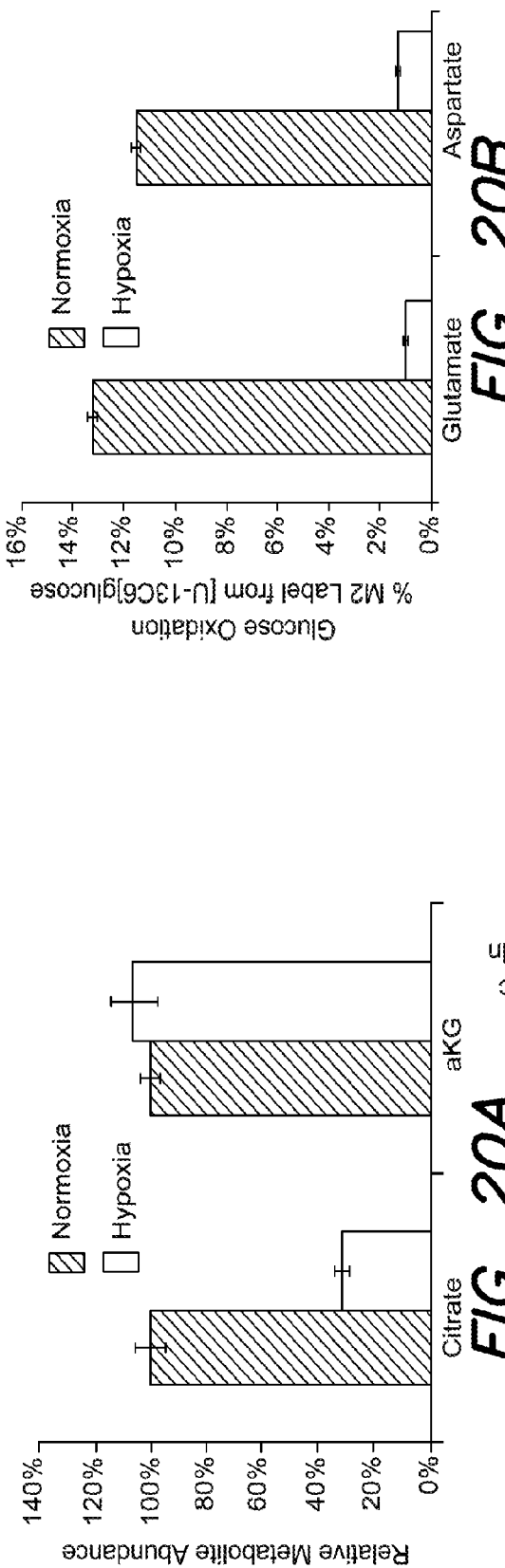
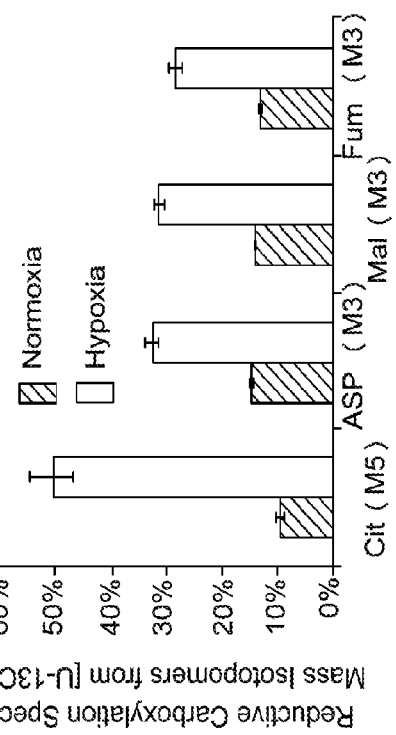
FIG. 20A
FIG. 20B
FIG. 20D

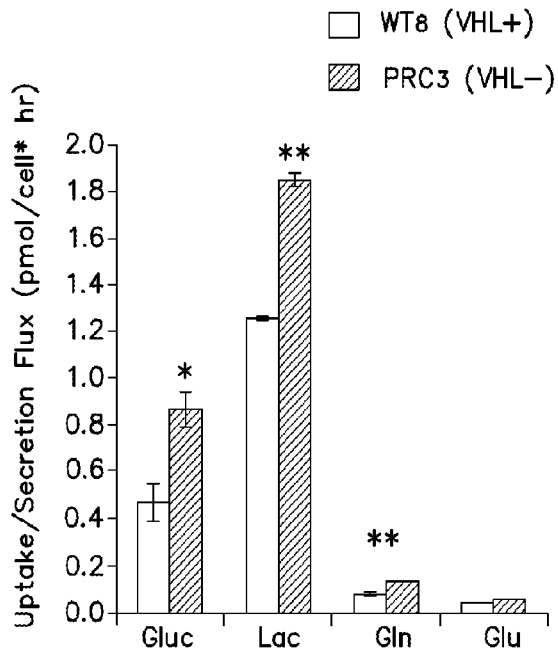
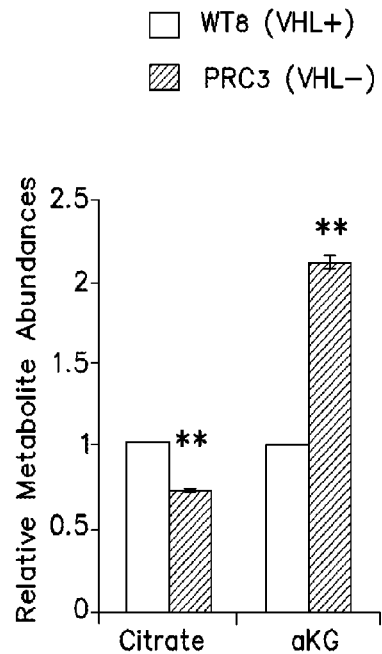
FIG. 29A
FIG. 29B
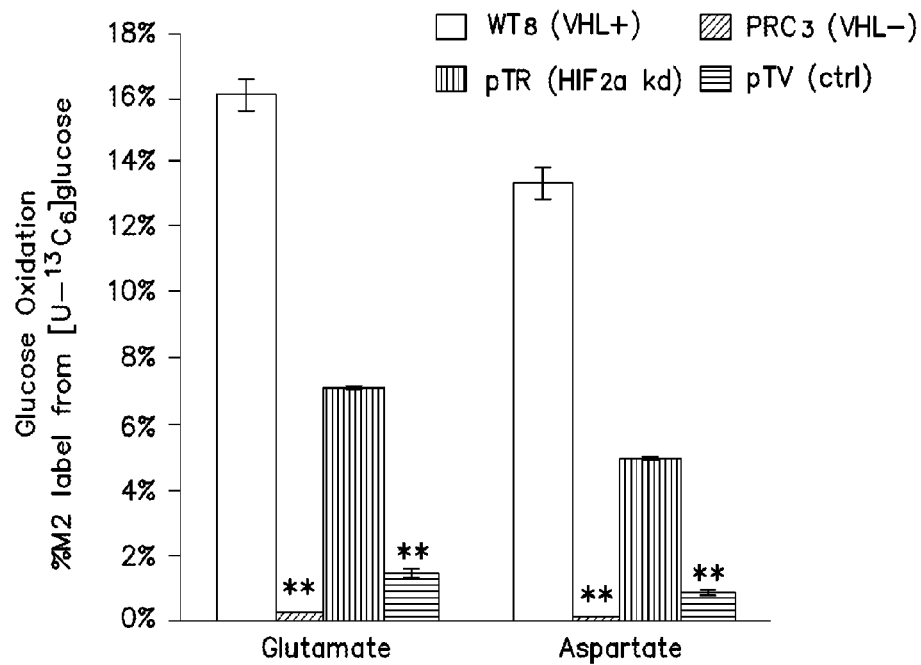
FIG. 29C

SEQUENCE LISTING

<160> NUMBER OF SEQ ID NOS: 4

<210> SEQ ID NO 1
<211> LENGTH: 57
<212> TYPE: DNA
<213> ORGANISM: Artificial Sequence
<220> FEATURE:
<223> OTHER INFORMATION: shRNA sequence

<400> SEQUENCE: 1
ccgggctgct tgcattaaag gtttactcga gtaaaccttt aatgcaagca gcttttt        57

<210> SEQ ID NO 2
<211> LENGTH: 57
<212> TYPE: DNA
<213> ORGANISM: Artificial Sequence
<220> FEATURE:
<223> OTHER INFORMATION: shRNA sequence

<400> SEQUENCE: 2
ccggcgaatc atttgggaat tgattctcga gaatcaattc ccaaatgatt cgttttt        57

<210> SEQ ID NO 3
<211> LENGTH: 57
<212> TYPE: DNA
<213> ORGANISM: Artificial Sequence
<220> FEATURE:
<223> OTHER INFORMATION: shRNA sequence

<400> SEQUENCE: 3
ccgggtggac atccagctaa agtatctcga gatactttag ctggatgtcc acttttt        57

<210> SEQ ID NO 4
<211> LENGTH: 57
<212> TYPE: DNA
<213> ORGANISM: Artificial Sequence
<220> FEATURE:
<223> OTHER INFORMATION: shRNA sequence

<400> SEQUENCE: 4
ccgggagaag tcagatggtt tatttctcga gaaataaacc atctgacttc tcttttt        57

METABOLIC GENE, ENZYME, AND FLUX TARGETS FOR CANCER THERAPY

RELATED APPLICATIONS

This application is a national stage filing under 35 U.S.C. §371 of international application PCT/US2011/043324, filed Jul. 8, 2011, which was published under PCT Article 21(2) in English, and claims the benefit under 35 U.S.C. §119(e) of U.S. Provisional Application Ser. No. 61/363,192, filed on Jul. 9, 2010, and of U.S. Provisional Application Ser. No. 61/434,094, filed on Jan. 19, 2011, the entire contents of each of which is incorporated by reference herein in its entirety.

GOVERNMENT INTEREST

This work was funded in part by the National Institutes of Health under grant numbers 6914322 and 1R01DK075850-01. The government has certain rights in this invention.

FIELD OF THE INVENTION

A novel pathway in cancer cell metabolism is identified. Targeting of any gene, protein, or enzyme that modulates activity or flux through this pathway, including, but not limited to IDH1, isocitrate dehydrogenase 2 (IDH2), aconitase 1 (ACO1), aconitase 2 (ACO2), glutaminase (GLS), glutamate dehydrogenase (GDH) and transaminase, provides an effective means of inhibiting tumor growth.

BACKGROUND OF THE INVENTION

Tumor cells transform their metabolism to proliferate aggressively and survive metabolic stresses. Acetyl coenzyme A (AcCoA) is the central biosynthetic precursor for fatty acid synthesis and protein acetylation. In the conventional view of mammalian cell metabolism, AcCoA is primarily generated from glucose-derived pyruvate through the citrate shuttle and adenosine triphosphate citrate lyase (ACL) in the cytosol. However, proliferating cells that exhibit aerobic glycolysis and those exposed to hypoxia convert glucose to lactate at near stoichiometric levels, directing glucose carbon away from the tricarboxylic acid cycle (TCA) and fatty acid synthesis. Although glutamine is consumed at levels exceeding that required for nitrogen biosynthesis, the regulation and utilization of glutamine metabolism in hypoxic cells is not well understood.

SUMMARY OF THE INVENTION

Here we show that cancer cells employ reductive metabolism of alpha-ketoglutarate ($\alpha$KG) to synthesize AcCoA for lipid synthesis in a reaction catalyzed by isocitrate dehydrogenase 1 (IDH1). This enzyme plays a central role in mediating cellular response to hypoxia. Furthermore, cells grown under hypoxia, including tumor cells in low oxygen environments, or those deficient in the von Hippel-Lindau (VHL) tumor suppressor rely almost entirely on the reductive carboxylation of glutamine-derived $\alpha$KG for lipogenesis. Our findings identify a new function of IDH1 in tumor cells and link reductive metabolism to lipid synthesis and cellular oxygen sensing. These results fundamentally alter our understanding of cellular metabolism and identify a critical role of oxygen in regulating carbon utilization in human cells.

According to one aspect of the invention methods for treating a cancer, inhibiting cell proliferation, inhibiting tumor growth, survival or vascularization, or regulating a response to hypoxia in a subject are provided. The methods include administering to a subject in need of such treatment a therapeutically effective amount of a composition comprising a compound that reduces the activity or expression of isocitrate dehydrogenase 1 (IDH1), isocitrate dehydrogenase 2 (IDH2), aconitase 1 (ACO1), aconitase 2 (ACO2), glutaminase (GLS), glutamate dehydrogenase (GDH) or transaminase to treat the cancer, inhibit the cell proliferation, inhibit the tumor growth, survival or vascularization, or regulate the response to hypoxia.

In some embodiments, the compound that reduces the activity or expression of IDH1, IDH2, ACO1, ACO2, GLS, GDH or transaminase is a small interfering RNA molecule. In other embodiments, the compound that reduces the activity or expression of IDH1, IDH2, ACO1, ACO2, GLS, GDH or transaminase is a small molecule inhibitor of IDH1, IDH2, ACO1, ACO2, GLS, GDH or transaminase, such as oxalomalate, 2-methylisocitrate, 6-diazo-5-oxo-1-norleucine or bis-2-(5-phenylacetamido-1,2,4-thiadiazol-2-yl)ethyl sulfide.

In some embodiments, the treatment inhibits further growth of the cancer or tumor or results in regression of the cancer or tumor. In some embodiments, the cancer or tumor is a carcinoma, a sarcoma or a melanoma. In some embodiments, the cancer or tumor is a pseudohypoxic cancer or tumor. In some embodiments, the pseudohypoxic cancer or tumor is a von Hippel-Lindau (VHL)-deficient renal carcinoma or comprises one or more mutations in succinate dehydrogenase and/or fumarate hydrogenase. In some embodiments, the pseudohypoxic cancer or tumor is a brain cancer or a renal cancer.

In some embodiments, the subject is a human. In some embodiments, the methods further include administering to the subject a different anti-cancer compound. In some embodiments, the response to hypoxia that is regulated is activation of hypoxia inducible factors (HIFs).

According to another aspect of the invention, methods for regulating alpha-ketoglutarate ($\alpha$KG)-dependent oxygenases in a cell are provided. The methods include contacting the cell with a compound that reduces the activity or expression of isocitrate dehydrogenase 1 (IDH1), isocitrate dehydrogenase 2 (IDH2), aconitase 1 (ACO1), aconitase 2 (ACO2), glutaminase (GLS), glutamate dehydrogenase (GDH) or transaminase in an amount effective to regulate alpha-ketoglutarate ($\alpha$KG)-dependent oxygenase activity.

In some embodiments, the compound that reduces the activity or expression of IDH1, IDH2, ACO1, ACO2, GLS, GDH or transaminase is a small interfering RNA molecule. In other embodiments, the compound that reduces the activity or expression of IDH1, IDH2, ACO1, ACO2, GLS, GDH or transaminase is a small molecule inhibitor of IDH1, IDH2, ACO1, ACO2, GLS, GDH or transaminase, such as oxalomalate, 2-methylisocitrate, 6-diazo-5-oxo-1-norleucine or bis-2-(5-phenylacetamido-1,2,4-thiadiazol-2-yl)ethyl sulfide.

In some embodiments, the alpha-ketoglutarate ($\alpha$KG)-dependent oxygenase is a prolyl hydroxylase (PHD).

In some embodiments, the cell is contacted under hypoxic conditions.

According to another aspect of the invention, pharmaceutical compositions are provided. The pharmaceutical compositions include a small interfering RNA molecule that reduces the activity or expression of isocitrate dehydrogenase 1 (IDH1), isocitrate dehydrogenase 2 (IDH2), aconitase 1 (ACO1), aconitase 2 (ACO2), glutaminase (GLS), glutamate dehydrogenase (GDH) or transaminase and a pharmaceutically acceptable carrier.

According to another aspect of the invention, pharmaceutical compositions are provided. The pharmaceutical compositions include a small molecule inhibitor of isocitrate dehydrogenase 1 (IDH1), isocitrate dehydrogenase 2 (IDH2), aconitase 1 (ACO1), aconitase 2 (ACO2), glutaminase (GLS), glutamate dehydrogenase (GDH) or transaminase and a pharmaceutically acceptable carrier. In some embodiments, the compound is oxalomalate, 2-methylisocitrate, 6-diazo-5-oxo-1-norleucine or bis-2-(5-phenylacetamido-1,2,4-thiadiazol-2-yl)ethyl sulfide.

In some embodiments, the foregoing pharmaceutical compositions further include a different anti-cancer compound.

According to another aspect of the invention, methods for identifying compounds or compositions useful as pharmacological agents for the treatment of cancer, inhibiting cell proliferation, inhibiting tumor growth, survival or vascularization, regulating a response to hypoxia and/or modulating activity of α-ketoglutarate-dependent dioxygenases are provided. The methods include contacting a cell with a compound or composition, and determining activity or flux through the reductive carboxylation pathway in the cell. Modulation of activity or flux through the reductive carboxylation pathway relative to a control amount of activity or flux through the reductive carboxylation pathway is an indication that the compound or composition is a candidate pharmacological agent is useful in the treatment of cancer, inhibiting cell proliferation, inhibiting tumor growth, survival or vascularization, regulating response to hypoxia and/or modulating activity of α-ketoglutarate-dependent dioxygenases.

In some embodiments, the methods further include determining a second amount of activity or flux through the reductive carboxylation pathway in the cell in the absence of the compound or composition, and using the second amount of activity or flux through the reductive carboxylation pathway as the control amount of activity or flux through the reductive carboxylation pathway.

In some embodiments, the activity or flux through the reductive carboxylation pathway is determined by isotope labeling and metabolite extraction. Preferably the determination of activity or flux through the reductive carboxylation pathway includes isotopomer spectral analysis.

In some embodiments, the cell is a cancer cell. In some embodiments, the cancer cell is a carcinoma cell, a sarcoma cell or a melanoma cell. In some embodiments, the cancer cell is a pseudohypoxic cancer cell. In some embodiments, the pseudohypoxic cancer cell is a von Hippel-Lindau (VHL)-deficient renal carcinoma cell or comprises one or more mutations in succinate dehydrogenase and/or fumarate hydrogenase. In some embodiments, the pseudohypoxic cancer cell is a brain cancer cell or a renal cancer cell.

In some embodiments, the compound is a small interfering RNA molecule or a plurality of such molecules. In other embodiments, the compound is a small organic molecule or a plurality of such molecules.

Other advantages, features, and uses of the invention will be apparent from the detailed description of certain non-limiting embodiments, the drawings, which are schematic and not intended to be drawn to scale, and the claims.

BRIEF DESCRIPTION OF THE DRAWINGS

FIG. 17. Knockdown of IDH1 does not increase hypoxia signaling and stabilization. A) Hypoxia response element-(HRE-) driven reporter levels in HCT116 cells expressing different IDH1-targeting shRNAs (IDH1a and IDH1b) versus scrambled control. Cells were cultured normally, under hypoxia, or in the presence of 1 mM DMOG for 18 hours before lysis. From left in each set of bars: control, IDH1a shRNA, IDH1b shRNA. Error bars indicate s.e.m. (n=3). B) HIF1α and IDH1 protein levels in HCT116 cells expressing shRNAs targeting IDH1 and cultured for 4 hours under normoxia or hypoxia. Cells in (B) were from an independent experiment with less efficient knockdown of IDH1 protein. C) HIF1α and IDH1 protein levels in 143B cells expressing shRNAs targeting IDH1 and cultured for 18 hours under normoxia or hypoxia. D) Relative flux through reductive carboxylation increases in 143B cells expressing control or IDH1-targeting shRNAs when cultured under hypoxia, as demonstrated by transfer of [1-$^{13}$C]glutamine to citrate. From left in each set of bars: control, IDH1a shRNA, IDH1b shRNA.

FIG. 29. Metabolic effects of VHL expression and HIF2α knockdown in 786-O cells. A) Cell-specific uptake and secretion of glucose/glutamine and lactate/glutamate, respectively. Metabolite levels were measured at the start and end of culture and normalized to the integral viable cell density to calculate fluxes. B) Relative metabolite abundances in extracts of PRC3 cells normalized to WT8 cells (and a norvaline internal standard). Equal numbers of cells were plated, and cells were extracted 18 hours later. From left in each set of bars in (A,B): WT8 (VHL+) (dark grey bars) and PRC3 (VHL−) (light grey bars). * denotes p<0.05 comparing WT8 to PRC3 cells.  denotes p<0.01 comparing WT8 to PRC3 cells. C) Relative level of glucose oxidation in PRC3, WT8, vector control (pTV), or HIF2α shRNA (pTR) cells, as measured by the relative abundance of M2 isotopomers in glutamate and aspartate pools in cells cultured with [U-$^{13}$C6]glucose. From left in each set of bars in (C): WT8 (VHL+), PRC3 (VHL−), pTR (HIF2a kd) and pTV (ctrl).  denotes p<0.01 comparing WT8 to PRC3 or pTV to pTR cells. Error bars indicate s.e.m. (n=3)

DETAILED DESCRIPTION OF THE INVENTION

Figure 1A:
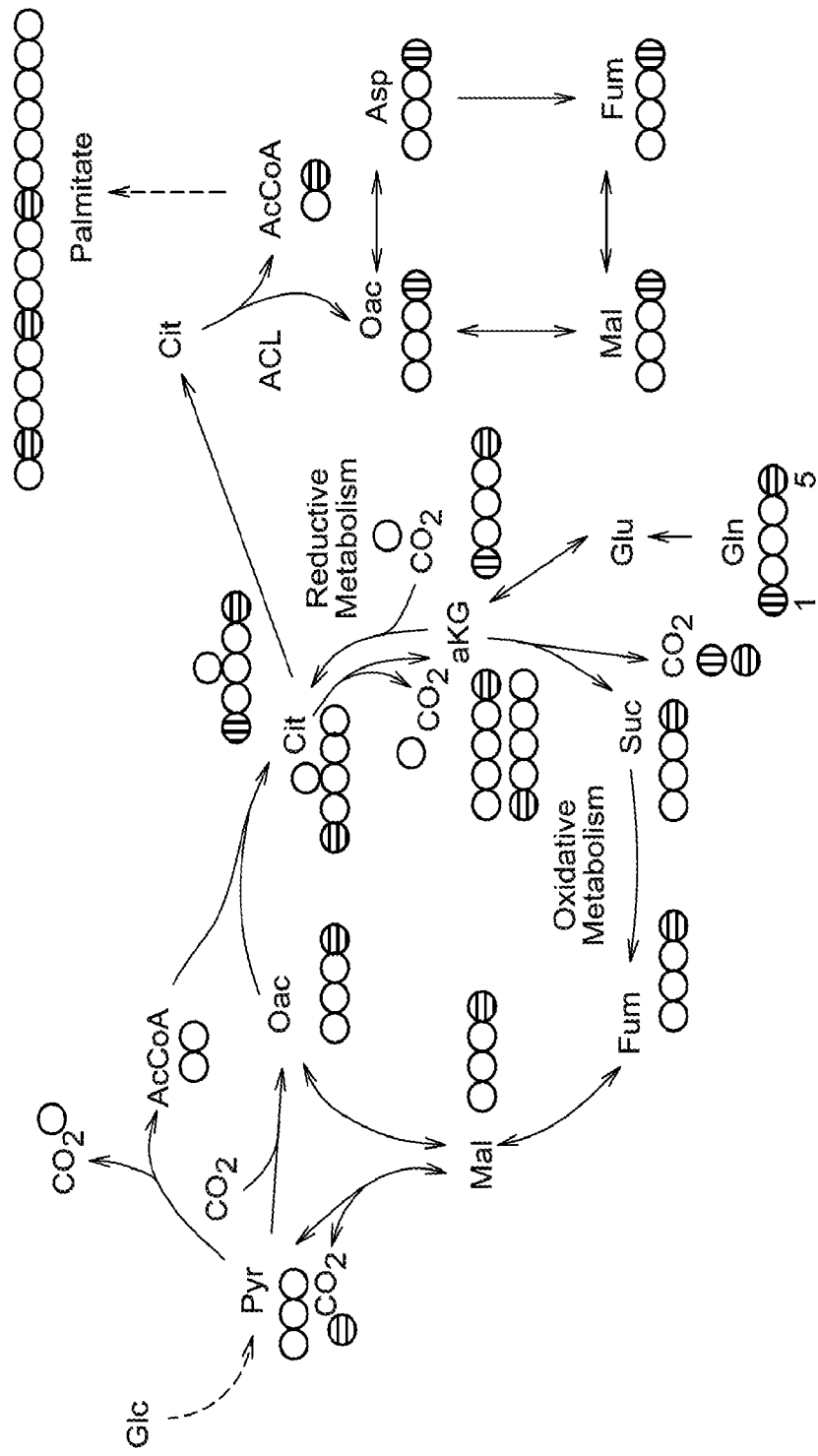
FIG. 1. Reductive carboxylation is the primary route of glutamine carbon-to-lipid flux. A) Carbon atom (represented by circles) transitions and tracers used to detect the reductive metabolism of αKG. Isotopic label from a [1-$^{13}$C]glutamine tracer (red/dark grey) is lost during oxidative metabolism by oxoglutarate dehydrogenase to succinate (Suc) but retained on citrate (Cit), oxaloacetate (Oac), aspartate (Asp), malate (Mal), and fumarate (Fum) in the reductive pathway (green arrows). The [5-$^{13}$C]glutamine tracer (blue/light grey) transfers label to AcCoA and fatty acids (e.g. palmitate) only through the reductive pathway and cannot label AcCoA through oxidative metabolism (see FIG. 9 for more detailed description). For brevity, molecular symmetry and exchange reactions are not shown; ACL enzyme/reaction is depicted in red. B) Reductive glutamine metabolism in A549 lung carcinoma cells. C) Mass isotopomer distribution (MID) demonstrating the reductive transfer of glutamine carbon to palmitate in H1299 (white bars) and A549 (grey bars) cells. Error bars indicate s.e.m. (n=3). D) Percent contribution of glutamine to lipogenic AcCoA through reductive carboxylation (blue/grey; [5-$^{13}$C]glutamine) or all pathways (white; [U-$^{13}$C$_5$]glutamine). Error bars indicate 95% confidence interval (CI) obtained from the model output. * denotes p<0.05 comparing ISA results from [5-$^{13}$C]glutamine to [U-$^{13}$C$_5$]glutamine.

The prevailing view of fatty acid synthesis in mammals involves the glycolytic conversion of glucose via the pyruvate-citrate shuttle to ultimately produce cytosolic acetyl-coenzyme A (AcCoA; FIG. 6A). AcCoA generated by adenosine triphosphate-citrate lyase (ACL) can then be used for fatty acid synthesis or protein acetylation (1-3). Proliferating cells consume high levels of glucose for energy production and biomolecular synthesis (e.g. ribose, lipids) but also metabolize glutamine at levels above that required for nitrogen metabolism (4). In the glutaminolysis pathway cells can oxidize glutamine and generate pyruvate and reduced nicotinamide adenine dinucleotide phosphate (NADPH) via malic enzyme (5). Alternatively, some metabolically active tissues can reductively carboxylate alpha-ketoglutarate (αKG) to generate citrate (6, 7). This reaction is known to be catalyzed by NADP$^+$-dependent IDH enzymes, but the specific isozyme responsible (cytosolic IDH1 or mitochondrial IDH2) is unclear (8, 9). While the reductive pathway has recently been shown to contribute significantly to AcCoA pools in the malaria parasite *Plasmodium falciparum* (10), glucose is conventionally believed to be the primary source of lipid carbon in animal cells (1, 3). As interest in the clinical targeting of tumor cell metabolism grows, a quantitative understanding of how various metabolic pathways are utilized during cell proliferation and regulated in physiologically relevant contexts is required.

Mechanisms of $O_2$ sensing are conserved throughout evolution, and hypoxia-response pathways encompassing oncogene-initiated cellular signaling have been extensively studied (11, 12). In mammalian cells hypoxic signals are mediated in part by hypoxia inducible factors (HIFs), which promote survival and vascularization of cells and tissues under low oxygen levels (13). HIFα subunits are hydroxylated in the presence of oxygen and subsequently targeted for degradation by the von Hippel-Lindau (VHL) E3 ubiquitin ligase (14, 15). HIF transduction can drive the metabolic phenotype of embryonic cells and tumors through transcription of genes such as phosphoglycerate kinase 1 (PGK1), lactate dehydrogenase A (LDHA), and pyruvate dehydrogenase kinase 1 (PDK1), directing carbon away from oxidative metabolism (16-18). However, glucose is not the sole carbon source metabolized by mammalian cells, and little is known about the interplay between hypoxia, the tricarboxylic acid (TCA) cycle, and reductive metabolism of glutamine. Conventional measurements of gene expression, enzyme activity and metabolite concentrations are insufficient to elucidate the metabolic dimensions of such signals. This information can be obtained only by the measurement of the corresponding fluxes, or rates of substrate conversion per cell per unit time, obtainable via labeling with stable isotopic tracers and Metabolic Flux Analysis (MFA) (19, 20).

Flux is the ultimate metric of individual enzyme and pathway function in vivo, the composite outcome of gene expression, protein synthesis, post-translational modifications (e.g. phosphorylation, acetylation) that may affect enzyme kinetics and/or stability, and metabolite level kinetics and regulation. Elaborate methods have been developed for flux determination in mammalian cells using stable isotopic tracers (21-23). The fundamental premise of these methods is that reaction rates and pathway topology determine the distribution of isotopic label among pathway metabolites. Additionally, metabolites and their mass isotopomers (i.e., compounds containing one or more labeled atoms) are subject to material balances under the assumption of metabolite steady state. Fluxes can then be determined such as to maximize the agreement between measured and predicted metabolite label distribution. State-of-the-art methods strive for largely overdetermined systems (containing more measurements than degrees of freedom) and generate flux confidence intervals along with absolute flux estimates (23-25). These techniques provide information on the dynamics of metabolic reactions, which cannot be ascertained from metabolite abundances. In practical terms, identification of the most active fluxes may enable discovery of new or more effective drug targets (e.g. enzymes) to mitigate tumor growth. Here we have applied isotopic tracer labeling and MFA to characterize the function of IDH1 in human cells, identifying a critical role for IDH1-mediated reductive metabolism in lipogenesis during hypoxic cell growth.

Here we identify a novel pathway in cancer cell metabolism, reductive carboxylation catalyzed by isocitrate dehydrogenase 1 (IDH1), which contributes to the tumor phenotype. This pathway modulates the activity of α-ketoglutarate (αKG or 2-oxoglutarate)-dependent dioxygenases, which regulate various cellular functions, including the response to hypoxia (low oxygen). Activation of hypoxia inducible factors (HIFs) promotes tumor growth, survival, and vascularization and is associated with poor prognosis in cancer patients, making this an attractive target for cancer therapy. Additionally, under the more physiologically relevant conditions of hypoxia, tumors utilize this metabolic pathway as the primary source of carbon for fatty acid synthesis. Therefore, targeting of any gene, protein, or enzyme that modulates activity or flux through the reductive carboxylation pathway, including, but not limited to IDH1, isocitrate dehydrogenase 2 (IDH2), aconitase 1 (ACO1), aconitase 2 (ACO2), glutaminase (GLS), glutamate dehydrogenase (GDH) and transaminase, will provide an effective means of inhibiting tumor growth in patients.

The current view of IDH1 function in tumor cells is to operate in the "forward" direction (analogous to flux in the Krebs cycle), converting isocitrate to aKG and regenerating the cofactor NADPH, which is required for biosynthetic reactions (FIG. 1). A quote from a recent article (Ward et al., Cancer Cell, 2010) discussing this enzyme highlights this perception:

IDH1 is one of only three cytosolic enzymes that contribute to the NADPH production required for nucleotide and lipid biosynthesis during cell growth (DeBerardinis et al., 2007). In addition, IDH1 contributes to the maintenance of cytosolic redox state (Yan et al., 2009). Therefore, there are several reasons why IDH1 might be important for cell proliferation.

Furthermore, the authors go on to assert that the mitochondrial enzyme IDH2 catalyzes flux through the reductive (reverse) pathway. Others have recently published data suggesting that IDH1 is a tumor suppressor, and loss of activity can lead to activation of the HIF oncogene (FIG. 1). Our findings demonstrate that the opposite is true, and, in fact, IDH1 actually consumes NADPH by catalyzing the reverse reaction and is required for cells to efficiently activate HIFs.

Using state-of-the-art analytical and computational methods we demonstrate that IDH1 carries out the reductive reaction to consume αKG in the cytosol. Metabolic flux in this "reverse" direction occurs in tumor cell lines of various tissue origins, including lung, colon, and breast carcinoma. We demonstrate this finding by culturing cells with specifically-labeled isotopic tracers (e.g. [1-$^{13}$C]glutamine) and observing differential labeling in metabolites using gas chromatography/mass spectrometry (GC/MS). By comparing cells expressing short hairpin RNAs (shRNAs) targeting cytosolic IDH1, mitochondrial IDH2, or control shRNAs we demonstrate that knockdown of IDH1 expression alone decreases the reductive carboxylation (reverse) flux (FIG. 2).

We extend these results to demonstrate regulation of aKG-dependent dioxygenases by IDH1-mediated reductive flux. The most well-studied function of this family of enzymes is the prolyl hydroxylase (PHD)-mediated oxygen sensing pathway, which acts to stabilize HIFs in conditions of hypoxia. Tumor cells with low expression of IDH1 and decreased reductive αKG metabolism have a compromised ability to transactivate HIF targets during hypoxic culture, which is due to increased activity of PHDs.

Finally, using several uniquely labeled [$^{13}$C]glutamine tracers, we establish that increases in reductive flux play a critical role in the cellular response to hypoxia. Tumor cells cultured in a low O2 environment significantly increase reductive metabolism through IDH1. In addition, carbon utilization of hypoxic cells is dramatically reorganized, as flux from glutamine through the reductive pathway (as opposed to glucose in normoxic cells) becomes the primary source of carbon for lipid synthesis (FIG. 3).

Based on the above findings, the invention includes in certain embodiments targeting of any gene, enzyme, or protein that regulates flux along the reductive carboxylation pathway via drug, RNA interference, or any other methods. Modulation of this pathway provides a means of inhibiting tumor growth and survival. Although not wishing to be limited to any particular mechanism, we describe two distinct mechanisms of activity. The first involves mitigation of hypoxic signaling and deregulation of any other pathway controlled by aKG-dependent dioxygenases (e.g. histone demethylation). The second targets the primary source of carbon for lipid biosynthesis in hypoxic cells: reductive carboxylation of αKG in the cytosol. The invention also includes in certain embodiments identification (and use) of compounds that target the above reductive carboxylation pathway and have beneficial action against tumor growth, vascularization and survival.

Compounds of the Invention

Compounds of the invention are those molecules that are useful in methods of the invention. Such molecules can be modulators of the activity or expression of a gene or gene product that modulates activity or flux through the reductive carboxylation pathway, preferably isocitrate dehydrogenase 1 (IDH1), isocitrate dehydrogenase 2 (IDH2), aconitase 1 (ACO1), aconitase 2 (ACO2), glutaminase (GLS), glutamate dehydrogenase (GDH) and transaminase, more preferably IDH1.

In some embodiments, molecules that inhibit expression of IDH1, IDH2, ACO1, ACO2, GLS, GDH or transaminase are short double stranded (ds) nucleic acid molecules, such as dsRNA molecules, which may operate via RNA interference (RNAi).

Although the dsRNA contains a sequence which corresponds to the target region of the (target) gene (e.g., IDH1, IDH2 or ACO1) it is not absolutely essential for the whole of the dsRNA to correspond to the sequence of the target region. For example, the dsRNA may contain short non-target regions flanking the target-specific sequence, provided that such sequences do not affect performance of the dsRNA in RNA inhibition to a material extent.

The expression "target region" or "target nucleotide sequence" of the (target) gene may be any suitable region or nucleotide sequence of the gene. The target region should comprise at least 17, at least 18 or at least 19 consecutive nucleotides of the (target) gene, more preferably at least 20 or at least 21 nucleotide and still more preferably at least 22, 23 or 24 nucleotides of the (target) gene.

The dsRNA may contain one or more substitute bases in order to optimize performance in RNAi. It will be apparent to the skilled person how to vary each of the bases of the dsRNA in turn and test the activity of the resulting siRNAs (e.g. in a suitable in vitro test system) in order to optimize the performance of a given dsRNA.

The dsRNA may further contain DNA bases, non-natural bases or non-natural backbone linkages or modifications of the sugar-phosphate backbone, for example, to enhance stability during storage or enhance resistance to degradation by nucleases.

It has also recently been suggested that synthetic RNA duplexes consisting of either 27-mer blunt or short hairpin (sh) RNAs with 29 bp stems and 2-nt 3' overhangs are more potent inducers of RNA interference than conventional 21-mer siRNAs. Thus, molecules based upon the targets identified above and being either 27-mer blunt or short hairpin (sh) RNAs with 29-bp stems and 2-nt 3' overhangs are also included within the scope of the invention.

The double-stranded RNA may be fully or partially double-stranded. Partially double-stranded RNAs may include short single-stranded overhangs at one or both ends of the double-stranded portion, provided that the RNA is still capable of being taken up by the cell and directing RNAi. The double-stranded RNA may also contain internal non-complementary regions.

Thus, the invention also features the use of small nucleic acid molecules, including antisense nucleic acids and short interfering nucleic acid (siNA), the latter include, for example: microRNA (miRNA), short interfering RNA (siRNA), double-stranded RNA (dsRNA), and short hairpin RNA (shRNA) molecules to knockdown expression of proteins such as IDH1, IDH2, ACO1, ACO2, GLS, GDH or transaminase. An siNA of the invention can be unmodified or chemically-modified. An siNA of the instant invention can be chemically synthesized, expressed from a vector or enzymatically synthesized. The instant invention also features various chemically-modified synthetic short interfering nucleic acid (siNA) molecules capable of modulating gene expression or activity in cells by RNA interference (RNAi). The use of chemically-modified siNA improves various properties of native siNA molecules through, for example, increased resistance to nuclease degradation in vivo and/or through improved cellular uptake. Furthermore, siNA having multiple chemical modifications may retain its RNAi activity. The siNA molecules of the instant invention provide useful reagents and methods for a variety of therapeutic applications. In some embodiments the IDH1, IDH2, ACO1, ACO2, GLS, GDH or transaminase expression inhibitors are used for treating cancer or modulating various enzymes including alpha-ketoglutarate-dependent oxygenases such as prolyl hydroxylases (PHDs), and/or pathways and processes of cells such as hypoxic responses.

Chemically synthesizing nucleic acid molecules with modifications (base, sugar and/or phosphate) that prevent their degradation by serum ribonucleases can increase their potency (see e.g., Eckstein et al., International Publication No. WO 92/07065; Perrault et al, 1990 Nature 344, 565; Pieken et al., 1991, Science 253, 314; Usman and Cedergren, 1992, Trends in Biochem. Sci. 17, 334; Usman et al., International Publication No. WO 93/15187; and Rossi et al., International Publication No. WO 91/03162; Sproat, U.S. Pat. No. 5,334,711; and Burgin et al., supra; all of these describe various chemical modifications that can be made to the base, phosphate and/or sugar moieties of the nucleic acid molecules herein). Modifications which enhance their efficacy in cells, and removal of bases from nucleic acid molecules to shorten oligonucleotide synthesis times and reduce chemical requirements are desired. There are several examples in the art describing sugar, base and phosphate modifications that can be introduced into nucleic acid molecules with significant enhancement in their nuclease stability and efficacy. For example, oligonucleotides are modified to enhance stability and/or enhance biological activity by modification with nuclease resistant groups, for example, 2' amino, 2'-C-allyl, 2'-fluoro, 2'-O-methyl, 2'-H, nucleotide base modifications (for a review see Usman and Cedergren, 1992, TIBS. 17, 34; Usman et al., 1994, Nucleic Acids Symp. Ser. 31, 163; Burgin et al., 1996, Biochemistry, 35, 14090). Sugar modification of nucleic acid molecules have been extensively described in the art (see Eckstein et al., International Publication PCT No. WO 92/07065; Perrault et al. Nature, 1990, 344, 565 568; Pieken et al. Science, 1991, 253, 314317; Usman and Cedergren, Trends in Biochem. Sci., 1992, 17, 334 339; Usman et al. International Publication PCT No. WO 93/15187; Sproat, U.S. Pat. No. 5,334, 711 and Beigelman et al., 1995, J. Biol. Chem., 270, 25702; Beigelman et al., International PCT publication No. WO 97/26270; Beigelman et al., U.S. Pat. No. 5,716,824; Usman et al., molecule comprises one or more chemical modifications. All of these publications are hereby incorporated by reference herein for these specific teachings.

In one embodiment, one of the strands of the double-stranded siNA molecule comprises a nucleotide sequence that is complementary to a nucleotide sequence of a target RNA or a portion thereof, and the second strand of the double-stranded siNA molecule comprises a nucleotide sequence identical to the nucleotide sequence or a portion thereof of the targeted RNA. In another embodiment, one of the strands of the double-stranded siNA molecule comprises a nucleotide sequence that is substantially complementary to a nucleotide sequence of a target RNA or a portion thereof, and the second strand of the double-stranded siNA molecule comprises a nucleotide sequence substantially similar to the nucleotide sequence or a portion thereof of the target RNA. In another embodiment, each strand of the siNA molecule comprises about 19 to about 23 nucleotides, and each strand comprises at least about 19 nucleotides that are complementary to the nucleotides of the other strand.

In some embodiments an siNA is an shRNA, shRNA-mir, or microRNA molecule encoded by and expressed from a genomically integrated transgene or a plasmid-based expression vector. Thus, in some embodiments a molecule capable of inhibiting mRNA expression, or microRNA activity, is a transgene or plasmid-based expression vector that encodes a small-interfering nucleic acid. Such transgenes and expression vectors can employ either polymerase II or polymerase III promoters to drive expression of these shRNAs and result in functional siRNAs in cells. The former polymerase permits the use of classic protein expression strategies, including inducible and tissue-specific expression systems. In some embodiments, transgenes and expression vectors are controlled by tissue specific promoters. In other embodiments transgenes and expression vectors are controlled by inducible promoters, such as tetracycline inducible expression systems.

In another embodiment, a small interfering nucleic acid of the invention is expressed in mammalian cells using a mammalian expression vector. The recombinant mammalian expression vector may be capable of directing expression of the nucleic acid preferentially in a particular cell type (e.g., tissue-specific regulatory elements are used to express the nucleic acid). Tissue specific regulatory elements are known in the art. Non-limiting examples of suitable tissue-specific promoters include the myosin heavy chain promoter, albumin promoter, lymphoid-specific promoters, neuron specific promoters, pancreas specific promoters, and mammary gland specific promoters. Developmentally-regulated promoters are also encompassed, for example the murine hox promoters and the alpha-fetoprotein promoter.

The terms "knockdown of gene expression", "inhibition of gene expression" and the like are used interchangeably and refer to a measurable or observable reduction in gene expression or a complete abolition of detectable gene expression, at the level of protein product and/or mRNA product from the (target) gene. Knockdown or inhibition of gene expression is "specific" when knockdown or inhibition of the (target) gene occurs without manifested effects on other genes of the targeted cell or organism.

The term "knockdown of gene expression" implies reduced expression of one or more genes of an organism due to the action of a dsRNA such as a short DNA or RNA oligonucleotide with a sequence complementary to a gene or its mRNA transcripts. During a gene knockdown event, the binding of this dsRNA to the gene or its transcripts causes decreased expression through blocking of transcription.

Depending on the nature of the affected gene, knockdown or inhibition of gene expression in cells can be confirmed by phenotypic analysis of a cell or by measurement of mRNA or protein expression using molecular techniques such as RNA solution hybridization, nuclease protection, Northern hybridization, reverse transcription polymerase chain reaction, gene expression monitoring with a microarray, antibody binding, enzyme-linked immunosorbent assay (ELISA), Western blotting, radioimmunoassay (RIA), other immunoassays, or fluorescence-activated cell analysis (FACS).

In other embodiments, molecules that inhibit activity or expression of IDH1, IDH2, ACO1, ACO2, GLS, GDH or transaminase are small organic molecules, such as oxalomalate (alpha-hydroxy-beta-oxalosuccinic acid; Yoo et al., J Biol Chem. 2008; 283:20621), 2-methylisocitrate (Yoo et al., J Biol Chem. 2008; 283:20621), DA-11004 (Shin et al. Arch Pharm Res. 2004 January; 27(1):48-52), D-threo-alpha-methylisocitrate (2S,3R)-3-hydroxy-1,2,3-butanetricarboxylate) (Beach et al. J Biol Chem. 1977 Apr. 25; 252(8):2702-9), DL-1,2,3-Tricarboxycyclopentene-1 (Gawron et al. Arch Biochem Biophys. 1971 December; 147(2): 772-780), mitogen-activated protein kinase (MAPK) inhibitors PD98059 and U0126 (Liu et al. Exp Biol Med (Maywood). 2006 May; 231(5):599-610), Janus tyrosine kinase 2 (Jak2) inhibitor AG490 (Liu et al. Exp Biol Med (Maywood). 2006 May; 231(5):599-610), 6-diazo-5-oxo-1-norleucine (DON), bis-2-(5-phenylacetamido-1,2,4-thiadiazol-2-yl)ethyl sulfide (BPTES), and aminooxyacetate. Such molecules can also serve as starting points for structure-activity relationship identification using standard methodologies known in the art.

Treating a Cancer in a Subject

In one aspect, the invention provides methods for treating a cancer in a subject by administering to a subject in need of such treatment a therapeutically effective amount of a composition that targets a nucleic acid molecule or polypeptide molecule that regulates flux along the reductive carboxylation pathway to treat the cancer in the subject. In some embodiments, the nucleic acid molecule or polypeptide molecule is isocitrate dehydrogenase 1 (IDH1), isocitrate dehydrogenase 2 (IDH2), aconitase 1 (ACO1) and aconitase 2 (ACO2), glutaminase (GLS), glutamate dehydrogenase (GDH) or transaminase.

As used herein, "treating a cancer" includes, but is not limited to, preventing the development of a cancer, reducing the symptoms of cancer, inhibiting the growth of an established cancer, preventing metastasis and/or invasion of an existing cancer, promoting or inducing regression of the cancer, inhibiting or suppressing the proliferation of cancerous cells, reducing angiogenesis or vascularization, or increasing the amount of apoptotic cancer cells. In some embodiments, the compounds of the invention are administered to a subject at risk of developing a cancer for the purpose of reducing the risk of developing the cancer.

The treatments described herein can be combined with conventional cancer treatments. Conventional treatment for cancer may include, but is not limited to: surgical intervention, chemotherapy, radiotherapy, and adjuvant systemic therapies. The pharmaceutical compositions of the invention may be administered alone, in combination with each other, and/or in combination with other anti-cancer drug therapies and/or treatments. These therapies and/or treatments may include, but are not limited to: surgical intervention, chemotherapy, radiotherapy, and adjuvant systemic therapies. Such additional therapies and/or treatments are described in greater detail elsewhere herein.

In some embodiments, the compounds of the invention can be used to treat cancers that are resistant to treatment by standard chemotherapies and anti-cancer compounds.

In some embodiments, treatment with the compounds of the invention results in a statistically significant suppression of the growth of cancer cells but does not result in a statistically significant suppression of the growth of non-cancer cells. The terms "non-cancer cells", "non-tumor cells", "healthy cells" and "normal cells", are used interchangeably herein, and refer to cells that are not undergoing the uncontrolled growth that characterizes cancer cells.

In some embodiments, the non-cancer cells grow at a rate that is similar to the growth rate of the cancer cells. A statistically significant suppression in the growth of treated cells is defined as greater than 5%, 10%, 20%, 30%, 40%, 50%, 60%, 70%, 80%, or 90% suppression of growth in comparison with untreated cells. A "growth at a rate similar to" is defined as a difference in growth rates between cell lines that is less than 1%, 5%, 10%, 20%, 30%, 40%, 50%, 60%, 70%, 80%, or 90%.

Cancer

In one aspect, the invention provides methods for the treatment of cancer. "Cancer" as used herein refers to an uncontrolled growth of cells which interferes with the normal functioning of the bodily organs and systems. Cancers which migrate from their original location and seed vital organs can eventually lead to the death of the subject through the functional deterioration of the affected organs. Carcinomas are malignant cancers that arise from epithelial cells and include adenocarcinoma and squamous cell carcinoma. Sarcomas are cancer of the connective or supportive tissue and include osteosarcoma, chondrosarcoma and gastrointestinal stromal tumor. Hematopoietic cancers, such as leukemia, are able to outcompete the normal hematopoietic compartments in a subject, thereby leading to hematopoietic failure (in the form of anemia, thrombocytopenia and neutropenia) ultimately causing death. A person of ordinary skill in the art can classify a cancer as a sarcoma, carcinoma or hematopoietic cancer.

Cancer, as used herein, includes the following types of cancer, breast cancer, biliary tract cancer; bladder cancer; brain cancer including glioblastomas and medulloblastomas; cervical cancer; choriocarcinoma; colon cancer; endometrial cancer; esophageal cancer; gastric cancer; hematological neoplasms including acute lymphocytic and myelogenous leukemia; T-cell acute lymphoblastic leukemia/lymphoma; hairy cell leukemia; chromic myelogenous leukemia, multiple myeloma; AIDS-associated leukemias and adult T-cell leukemia lymphoma; intraepithelial neoplasms including Bowen's disease and Paget's disease; liver cancer; lung cancer; lymphomas including Hodgkin's disease and lymphocytic lymphomas; neuroblastomas; oral cancer including squamous cell carcinoma; ovarian cancer including those arising from epithelial cells, stromal cells, germ cells and mesenchymal cells; pancreatic cancer; prostate cancer; rectal cancer; sarcomas including leiomyosarcoma, rhabdomyosarcoma, liposarcoma, fibrosarcoma, and osteosarcoma; skin cancer including melanoma, Kaposi's sarcoma, basocellular cancer, and squamous cell cancer; testicular cancer including germinal tumors such as seminoma, non-seminoma (teratomas, choriocarcinomas), stromal tumors, and germ cell tumors; thyroid cancer including thyroid adenocarcinoma and medullar carcinoma; and renal cancer including adenocarcinoma and Wilms tumor. Other cancers will be known to one of ordinary skill in the art.

In some embodiments, the cancer is not a brain cancer such as a glioma or glioblastoma, or a leukemia such as acute myeloid leukemia. In some embodiments, the cancer is not a cancer that expresses or contains a mutated IDH1 gene. Such cancers can be identified using standard methods (e.g., see Toedt et al., Int J Cancer. 2010 May 12 (epub) PMID: 20473936; Marcucci et al. J Clin Oncol. 2010 May 10; 28(14):2348-55. Epub 2010 Apr. 5.)

In some embodiments, the cancer or tumor is a pseudohypoxic cancer or tumor. The pseudohypoxic cancer or tumor can be a Von Hippel-Landau (VHL)-deficient renal carcinoma or can include one or more mutations in succinate dehydrogenase and/or fumarate hydrogenase. In some embodiments, the pseudohypoxic cancer or tumor is a brain cancer or a renal cancer, or a cancer or tumor as described in Bayley et al. Curr Opin Genet Dev. 2010 June; 20(3): 324-9.

Inhibiting Cell Proliferation

The compounds of the invention also can be used to inhibit cell proliferation. In one aspect, the invention provides methods for inhibiting cell proliferation by contacting the cell with a therapeutically effective amount of a composition comprising one or more compounds useful in methods of the invention. Inhibiting cell proliferation can be achieved through a variety of mechanisms, as described herein, which are all embraced by the invention. For instance, cell proliferation can be inhibited by reducing the amount or composition of nutrients available to a cell. In some embodiments, cells that have a higher potential to proliferate (e.g., cancer cells) are more strongly inhibited when compared to cells that have a lower potential to proliferate. In some embodiments, inhibiting cell proliferation according to the methods of the invention will result in the treatment of cancer in a subject.

Subject

In one aspect, the invention provides methods for the treatment of cancer in a subject. A "subject", as used herein, is a human or vertebrate mammal including, but not limited to, mouse, rat, dog, cat, horse, cow, pig, sheep, goat, or non-human primate. In some embodiments, the subject is otherwise free of symptoms treatable by compounds useful in the methods of the invention as described herein.

A "subject in need of treatment", as used herein, means a subject that is identified as being in need of treatment. For instance, a subject in need of cancer treatment is a subject identified as having cancer or being at risk for developing cancer. A subject may be diagnosed as being in need of treatment by a healthcare professional and/or by performing one or more diagnostic assays. For instance, a subject in need of cancer treatment may be a subject diagnosed with cancer or being at risk of cancer by a healthcare professional. Diagnostic assays to evaluate if a subject has a cancer or is at risk for developing cancer are available in the routine art.

Therapeutically Effective Amount

In some embodiments, the compounds useful in methods of the invention can be used in therapeutically effective amounts. The term "therapeutically effective amount" or "effective amount", which can be used interchangeably, refers to the amount necessary or sufficient to realize a desired therapeutic effect, e.g., shrinkage of a tumor, or inhibition or suppression of cell proliferation. Combined with the teachings provided herein, by choosing among the various active compounds and weighing factors such as potency, relative bioavailability, subject body weight, severity of adverse side-effects and preferred mode of administration, an effective prophylactic or therapeutic treatment regimen can be planned which does not cause substantial toxicity and yet is effective to treat the particular subject.

The effective amount for any particular application can vary depending on such factors as the disease or condition being treated, the particular compound being administered, the size of the subject, or the severity of the disease or condition. One of ordinary skill in the art can empirically determine the effective amount of a particular compound useful in methods of the invention and/or other therapeutic agent using routine experimentation. It is preferred generally that a maximum dose be used, that is, the highest safe dose according to some medical judgment. Multiple doses per day may be contemplated to achieve appropriate systemic levels of compounds. Appropriate system levels can be determined by, for example, measurement of the patient's peak or sustained plasma level of the drug.

In some embodiments, a therapeutically effective amount is less than 50 mg/kg, such as less than 45 mg/kg, less than 40 mg/kg, less than 35 mg/kg, less than 30 mg/kg, less than 25 mg/kg, less than 20 mg/kg or less than 15 mg/kg. In some embodiments, a therapeutically effective amount is less than 10 mg/kg, such as less than 9 mg/kg, less than 8 mg/kg, less than 7 mg/kg, less than 6 mg/kg, less than 5 mg/kg, less than 4 mg/kg, less than 3 mg/kg or less than 2 mg/kg. In some embodiments, a therapeutically effective amount is less than 1.5 mg/kg, such as less than 1.4 mg/kg, less than 1.3 mg/kg, less than 1.2 mg/kg, less than 1.1 mg/kg, less than 1 mg/kg, less than 0.9 mg/kg, less than 0.8 mg/kg, less than 0.7 mg/kg, less than 0.6 mg/kg, less than 0.5 mg/kg, less than 0.4 mg/kg, less than 0.3 mg/kg, less than 0.2 mg/kg or less than 0.1 mg/kg.

In some embodiments, a therapeutically effective amount of a particular compound is less than the LD50 of that particular compound, as determined by testing that particular compound in a model organism, such as mouse, rat or dog, or other disease model. In some embodiments, a therapeutically effective amount of a particular compound is less than 50%, less than 40%, less than 30%, less than 25%, less than 20%, less than 15%, less than 10%, less than 9%, less than 8%, less than 7%, less than 6%, less than 5%, less than 4%, less than 3% or less than 2% of the LD50 of that particular compound in a model organism. In some embodiments, a therapeutically effective amount of a particular compound is less than 1%, less than 0.9%, less than 0.8%, less than 0.7%, less than 0.6%, less than 0.5%, less than 0.4%, less than 0.3%, less than 0.2% or less than 0.1% of the LD50 of that particular compound in a model organism.

In some embodiments, the therapeutically effective amount is administered in one dose. In some embodiments, the therapeutically effective amount is administered in multiple doses. Dosage may be adjusted appropriately to achieve desired compound levels, local or systemic, depending upon the mode of administration. For example, it is expected that intravenous administration would require a lower dose than oral delivery to result in the same therapeutically effective amount. In the event that the response in a subject is insufficient at such doses, even higher doses (or effective higher doses by a different, more localized delivery route) may be employed to the extent that subject tolerance permits. Multiple doses per day are contemplated to achieve appropriate systemic levels of compounds.

Anti-Cancer Compounds

In some embodiments, compound(s) useful in methods of the invention can be administered combined with other therapeutic agents. The compound and other therapeutic agent may be administered simultaneously or sequentially. When the other therapeutic agents are administered simultaneously they can be administered in the same or separate formulations, but are administered at the same time. The other therapeutic agents are administered sequentially with one another and with the compound, when the administration of the other therapeutic agents and the compound is temporally separated. The separation in time between the administration of these compounds may be a matter of minutes or it may be longer.

In some embodiments, the other therapeutic agent is an anti-cancer compound. As used herein, an "anti-cancer compound" refers to an agent which is administered to a subject for the purpose of treating a cancer. Anti-cancer compounds include, but are not limited to anti-proliferative compounds, anti-neoplastic compounds, anti-cancer supplementary potentiating agents and radioactive agents. One of ordinary skill in the art is familiar with a variety of anti-cancer agents, or can find those agents in the routine art, which are used in the medical arts to treat cancer.

Anti-cancer agents include, but are not limited to, the following sub-classes of compounds: Antineoplastic agents such as: Acivicin; Aclarubicin; Acodazole Hydrochloride; Acronine; Adozelesin; Adriamycin; Aldesleukin; Altretamine; Ambomycin; Ametantrone Acetate; Aminoglutethimide; Amsacrine; Anastrozole; Anthramycin; Asparaginase; Asperlin; Azacitidine; Azetepa; Azotomycin; Batimastat; Buniodepa; Bicalutamide; Bisantrene Hydrochloride; Bisnafide Dimesylate; Bizelesin; Bleomycin Sulfate; Brequinar Sodium; Bropirimine; Busulfan; Cactinomycin; Calusterone; Caracemide; Carbetimer; Carboplatin; Carmustine; Carubicin Hydrochloride; Carzelesin; Cedefingol; Chlorombucil; Cirolemycin; Cisplatin; Cladribine; Crisnatol Mesylate; Cyclophosphamide; Cytarabine; Dacarbazine; DACA (N-[2-(Dimethyl-amino)ethyl]acridine-4-carboxamide); Dactinomycin; Daunorubicin Hydrochloride; Daunomycin; Decitabine; Dexormaplatin; Dezaguanine; Dezaguanine Ifesylate; Diaziquone; Docetaxel; Doxorubicin; Doxorubicin Hydrochloride; Droloxifene; Droloxifene Citrate; Dromostanolone Propionate; Duazomycin; Edatrexate; Eflornithine Hydrochloride; Elsamitrucin; Enloplatin; Enpromate; Epipropidine; Epirubicin Hydrochloride; Erbulozole; Esorubicin Hydrochloride; Estramustine; Estramustine Phosphate Sodium; Etanidazole; Ethiodized Oil I 131; Etoposide; Etoposide Phosphate; Etoprine; Fadrozole Hydrochloride; Fazarabine; Fenretinide; Floxuridine; Fludarabine Phosphate; Fluorouracil; 5-FdUMP; Fluorocitabine; Fosquidone; Fostriecin Sodium; Gemcitabine; Gemcitabine Hydrochloride; Gold Au 198; Hydroxyurea; Idarubicin Hydrochloride; Ifosfamide; Ilmofosine; Interferon Alfa-2a; Interferon Alfa-2b; Interferon Alfa-n1; Interferon Alfa-n3; Interferon Beta-1a; Interferon Gamma-1b; Iproplatin; Irinotecan Hydrochloride; Lanreotide Acetate; Letrozole; Leuprolide Acetate; Liarozole Hydrochloride; Lometrexol Sodium; Lomustine; Losoxantrone Hydrochloride; Masoprocol; Maytansine; Mechlorethamine Hydrochloride; Megestrol Acetate; Melengestrol Acetate; Melphalan; Menogaril; Mercaptopurine; Methotrexate; Methotrexate Sodium; Metoprine; Meturedepa; Mitindomide; Mitocarcin; Mitocromin; Mitogillin; Mitomalcin; Mitomycin, Mitosper; Mitotane; Mitoxantrone Hydrochloride; Mycophenolic Acid; Nocodazole; Nogalamycin; Ormaplatin; Oxisuran; Paclitaxel Pegaspargase; Peliomycin; Pentamustine; Peplomycin Sulfate; Perfosfamide; Pipobroman; Piposulfan; Piroxantrone Hydrochloride; Plicamycin; Plomestane; Porfimer Sodium; Porfiromycin; Prednimustine; Procarbazine Hydrochloride; Puromycin; Puromycin Hydrochloride; Pyrazofurin; Riboprine; Rogletimide; Safingol; Safingol Hydrochloride; Semustine; Simtrazene; Sparfosate Sodium; Sparsomycin; Spirogermanium Hydrochloride; Spiromustine; Spiroplatin; Streptonigrin; Streptozocin; Strontium Chloride Sr 89; Sulofenur; Talisomycin; Taxane; Taxoid; Tecogalan Sodium; Tegafur; Teloxantrone Hydrochloride; Temoporfin; Teniposide; Teroxirone; Testolactone; Thiamiprine; Thioguanine; Thiotepa; Thymitaq; Tiazofurin; Tirapazamine; Tomudex; TOP-53; Topotecan Hydrochloride; Toremifene Citrate; Trestolone Acetate; Triciribine Phosphate; Trimetrexate; Trimetrexate Glucuronate; Triptorelin; Tubulozole Hydrochloride; Uracil Mustard;

Uredepa; Vapreotide; Verteporfin; Vinblastine; Vinblastine Sulfate; Vincristine; Vincristine Sulfate, Vindesine; Vindesine Sulfate; Vinepidine Sulfate; Vinglycinate Sulfate; Vinleurosine Sulfate; Vinorelbine Tartrate; Vinrosidine Sulfate; Vinzolidine Sulfate; Vorozole; Zeniplatin; Zinostatin; Zorubicin Hydrochloride; 2-Chlorodeoxyadenosine; 2'-Deoxyformycin; 9-aminocamptothecin; raltitrexed; N-propargyl-5,8-dideazafolic acid, 2-chloro-2'-arabino-fluoro-2'-deoxyadenosine; 2-chloro-2'-deoxyadenosine; anisomycin; trichostatin A; hPRL-G129R; CEP-751; linomide; Piritrexim Isethionate; Sitogluside; Tamsulosin Hydrochloride and Pentomone.

Anti-neoplastic compounds include, but are not limited to 20-epi-1,25 dihydroxyvitamin D3; 5-ethynyluracil; abiraterone; aclarubicin; acylfulvene; adecypenol; adozelesin; aldesleukin; ALL-TK antagonists; altretamine; ambamustine; amidox; amifostine; aminolevulinic acid; amrubicin; amsacrine; anagrelide; anastrozole; andrographolide; angiogenesis inhibitors; antagonist D; antagonist G; antarelix; anti-dorsalizing morphogenetic protein-1; antiandrogen, prostatic carcinoma; antiestrogen; antineoplaston; antisense oligonucleotides; aphidicolin glycinate; apoptosis gene modulators; apoptosis regulators; apurinic acid; ara-CDP-DL-PTBA; arginine deaminase; asulacrine; atamestane; atrimustine; axinastatin 1; axinastatin 2; axinastatin 3; azasetron; azatoxin; azatyrosine; baccatin III derivatives; balanol; batimastat; BCR/ABL antagonists; benzochlorins; benzoylstaurosporine; beta lactam derivatives; beta-alethine; betaclamycin B; betulinic acid; bFGF inhibitor; bicalutamide; bisantrene; bisaziridinylspermine; bisnafide; bistratene A; bizelesin; breflate; bropirimine; budotitane; buthionine sulfoximine; calcipotriol; calphostin C; camptothecin derivatives (e.g., 10-hydroxy-camptothecin); canarypox IL-2; capecitabine; carboxamide-amino-triazole; carboxyamidotriazole; CaRest M3; CARN 700; cartilage derived inhibitor; carzelesin; casein kinase inhibitors (ICOS); castanospermine; cecropin B; cetrorelix; chlorins; chloroquinoxaline sulfonamide; cicaprost; cis-porphyrin; cladribine; clomifene analogues; clotrimazole; collismycin A; collismycin 13; combretastatin A4; combretastatin analogue; conagenin; crambescidin 816; crisnatol; cryptophycin 8; cryptophycin A derivatives; curacin A; cyclopentanthraquinones; cycloplatam; cypemycin; cytarabine ocfosfate; cytolytic factor; cytostatin; dacliximab; decitabine; dehydrodidemnin 10 deslorelin; dexifosfamide; dexrazoxane; dexverapamil; diaziquone; didemnin B; didox; diethylnorspermine; dihydro-5-azacytidine; dihydrotaxol, 9-; dioxamycin; diphenyl spiromustine; discodermolide; docosanol; dolasetron; doxifluridine; droloxifene; dronabinol; duocarmycin SA; ebselen; ecomustine; edelfosine; edrecolomab; eflornithine; elemene; emitefur; epirubicin; epothilones (A, R=H; B, R=Me); epithilones; epristeride; estramustine analogue; estrogen agonists; estrogen antagonists; etanidazole; etoposide; etoposide 4'-phosphate (etopofos); exemestane; fadrozole; fazarabine; fenretinide; filgrastim; finasteride; flavopiridol; flezelastine; fluasterone; fludarabine; fluorodaunorunicin hydrochloride; forfenimex; formestane; fostriecin; fotemustine; gadolinium texaphyrin; gallium nitrate; galocitabine; ganirelix; gelatinase inhibitors; gemcitabine; glutathione inhibitors; hepsulfam; heregulin; hexamethylene bisacetamide; hypericin; ibandronic acid; idarubicin; idoxifene; idramantone; ilmofosine; ilomastat; imidazoacridones; imiquimod; immunostimulant peptides; insulin-like growth factor-1 receptor inhibitor; interferon agonists; interferons; interleukins; iobenguane; iododoxorubicin; ipomeanol, 4-; irinotecan; iroplact; irsogladine; isobengazole; isohomohalicondrin B; itasetron; jasplakinolide; kahalalide F; lamellarin-N triacetate; lanreotide; leinamycin; lenograstim; lentinan sulfate; leptolstatin; letrozole; leukemia inhibiting factor; leukocyte alpha interferon; leuprolide+estrogen+progesterone; leuprorelin; levamisole; liarozole; linear polyamine analogue; lipophilic disaccharide peptide; lipophilic platinum compounds; lissoclinamide 7; lobaplatin; lombricine; lometrexol; lonidamine; losoxantrone; lovastatin; loxoribine; lurtotecan; lutetium texaphyrin; lysofylline; lytic peptides; maitansine; mannostatin A; marimastat; masoprocol; maspin; matrilysin inhibitors; matrix metalloproteinase inhibitors; menogaril; merbarone; meterelin; methioninase; metoclopramide; MIF inhibitor; mifepristone; miltefosine; mirimostim; mismatched double stranded RNA; mithracin; mitoguazone; mitolactol; mitomycin analogues; mitonafide; mitotoxin fibroblast growth factor-saporin; mitoxantrone; mofarotene; molgramostim; monoclonal antibody, human chorionic gonadotrophin; monophosphoryl lipid A+myobacterium cell wall sk; mopidamol; multiple drug resistance gene inhibitor, multiple tumor suppressor 1-based therapy; mustard anticancer agent; mycaperoxide B; mycobacterial cell wall extract; myriaporone; N-acetyldinaline; N-substituted benzamides; nafarelin; nagrestip; naloxone+pentazocine; napavin; naphterpin; nartograstim; nedaplatin; nemorubicin; neridronic acid; neutral endopeptidase; nilutamide; nisamycin; nitric oxide modulators; nitroxide antioxidant; nitrullyn; O6-benzylguanine; octreotide; okicenone; oligonucleotides; onapristone; ondansetron; oracin; oral cytokine inducer; ormaplatin; osaterone; oxaliplatin; oxaunomycin; paclitaxel analogues; paclitaxel derivatives; palauamine; palmitoylrhizoxin; pamidronic acid; panaxytriol; panomifene; parabactin; pazelliptine; pegaspargase; peldesine; pentosan polysulfate sodium; pentostatin; pentrozole; perflubron; perfosfamide; perillyl alcohol; phenazinomycin; phenylacetate; phosphatase inhibitors; picibanil; pilocarpine hydrochloride; pirarubicin; piritrexim; placetin A; placetin B; plasminogen activator inhibitor; platinum complex; platinum compounds; platinum-triamine complex; podophyllotoxin; porfimer sodium; porfiromycin; propyl bis-acridone; prostaglandin J2; proteasome inhibitors; protein A-based immune modulator; protein kinase C inhibitor; protein kinase C inhibitors, microalgal; protein tyrosine phosphatase inhibitors; purine nucleoside phosphorylase inhibitors; purpurins; pyrazoloacridine; pyridoxylated hemoglobin polyoxyethylene conjugate; raf antagonists; raltitrexed; ramosetron; ras farnesyl protein transferase inhibitors; ras inhibitors; ras-GAP inhibitor; retelliptine demethylated; rhenium Re 186 etidronate; rhizoxin; ribozymes; RII retinamide; rogletimide; rohitukine; romurtide; roquinimex; rubiginone B1; ruboxyl; safingol; saintopin; SarCNU; sarcophytol A; Sargramostim; Sdi 1 mimetics; semustine; senescence derived inhibitor 1; sense oligonucleotides; signal transduction inhibitors; signal transduction modulators; single chain antigen binding protein; sizofiran; sobuzoxane; sodium borocaptate; sodium phenylacetate; solverol; somatomedin binding protein; sonermin; sparfosic acid; spicamycin D; spiromustine; splenopentin; spongistatin 1; squalamine; stem cell inhibitor; stem-cell division inhibitors; stipiamide; stromelysin inhibitors; sulfinosine; superactive vasoactive intestinal peptide antagonist; suradista; suramin; swainsonine; synthetic glycosaminoglycans; tallimustine; tamoxifen methiodide; tauromustine; tazarotene; tecogalan sodium; tegafur; tellurapyrylium; telomerase inhibitors; temoporfin; temozolomide; teniposide; tetrachlorodecaoxide; tetrazomine; thaliblastine; thalidomide; thiocoraline; thrombopoietin; thrombopoietin mimetic; thymalfasin; thymopoietin receptor agonist; thymotrinan; thyroid stimulating hormone; tin ethyl etiopurpurin; tirapazamine; titanocene dichloride; topotecan; topsentin; toremifene; totipotent stem cell factor; translation inhibitors; tretinoin; triacetyluridine; triciribine; trimetrexate; triptorelin; tropisetron; turosteride; tyrosine kinase inhibitors; tyrphostins; UBC inhibitors; ubenimex urogenital sinus-derived growth inhibitory factor; urokinase receptor antagonists; vapreotide; variolin B; vector system, erythrocyte gene therapy; velaresol; veramine; verdins; verteporfin; vinorelbine; vinxaltine; vitaxin; vorozole; zanoterone; zeniplatin; zilascorb; zinostatin stimalamer.

Anti-cancer supplementary potentiating agents include, but are not limited to, Tricyclic anti-depressant drugs (e.g., imipramine, desipramine, amitryptyline, clomipramine, trimipramine, doxepin, nortriptyline, protriptyline, amoxapine and maprotiline); non-tricyclic anti-depressant drugs (e.g., sertraline, trazodone and citalopram); $Ca^{2+}$ antagonists (e.g., verapamil, nifedipine, nitrendipine and caroverine); Calmodulin inhibitor (e.g. prenylamine, trifluoroperazine and clomipramine); Amphotericin B; Triparanol analogues (e.g. tamoxifen); antiarrhythmic drugs (e.g., quinidine); antihypertensive drugs (e.g. reserpine); Thiol depleters (e.g., buthionine and sulfoximine) and Multiple Drug Resistance reducing agents such as Cremaphor EL. The compounds of the invention also can be administered with cytokines such as granulocyte colony stimulating factor.

Radioactive agents include but are not limited to Fibrinogen I 125; Fludeoxyglucose F18; Fluorodopa F 18; Insulin I 125; Insulin I 131; Iobenguane I 123; Iodipamide Sodium I 131; Iodoantipyrine I 131; Iodocholesterol I 131; Iodohippurate Sodium I 123; Iodohippurate Sodium I 125; Iodohippurate Sodium I 131; Iodopyracet I 125; Iodopyracet I 131; Iofetamine Hydrochloride I 123; Iomethin I 125; Iomethin I 131; Iothalamate Sodium I 125; Iothalamate Sodium I 131; Iotyrosine I 131; Liothyronine I 125; Liothyronine I 131; Merisoprol Acetate Hg 197; Merisoprol Acetate-Hg 203; Merisoprol Hg 197; Selenomethionine Se 75; Technetium Tc 99m Atimony Trisulfide Colloid; Technetium Tc 99m Bicisate; Technetium Tc 99m Disofenin; Technetium Tc 99m Etidronate; Technetium Tc 99m Exametazime; Technetium Tc 99m Furifosmin; Technetium Tc 99m Gluceptate; Technetium 99m Lidofenin; Technetium Tc 99 mm Mebrofenin; Technetium Tc 99m Medronate; Technetium Tc 99m Medronate Disodium; Technetium Tc 99m Mertiatide; Technetium Tc 99m Oxidronate; Technetium Tc 99m Pentetate; Technetium Ic 99m Pentetate Calcium Trisodium; Technetium Tc 99m Sestamibi; Technetium Tc 99m Siboroxime; Technetium Tc 99m Succimer; Technetium Tc 99m Sulfur Colloid; Technetium Tc 99m Teboroxime; Technetium Tc 99m Tetrofosmin; Technetium Tc 99m Tiatide; Thyroxine I 125: Thyroxine I 131; Tolpovidone I 131; Triolein I 125; Triolein I 131.

In some embodiments, the compounds of the invention are administered in conjunction with an anti-cancer therapy. Anti-cancer therapies include the administration of anti-cancer compounds, radiation and surgical procedure.

Screening Methods and Compounds

The invention provides various methods for identifying compounds or compositions that are useful as pharmacological agents for the treatment of cancer, inhibition of cell proliferation, modulating the activity of α-ketoglutarate-dependent dioxygenases, regulating the response to hypoxia, and/or modulating activity or flux through the reductive carboxylation pathway.

Similar assays as described herein can be performed using a variety of cells and cell lines, including cancer cells and cell lines. Based on the use of the assays described herein for metabolite analysis including flux analysis using e.g. isotope labeling and isotopomer spectral analysis, and gene expression knockdown analysis, a variety of molecules (test compounds) can be screened to identify compounds that are useful in the various methods described herein, including cancer treatment, inhibition of cell proliferation, etc.

Appropriate negative controls typically are performed in parallel with the assays of the test compounds or compositions, such as not contacting the cells with the test compound or composition or other component of the assay. The control assays in which an added component of the assay is omitted can be performed by substituting for the component the vehicle used for adding the component to the assay.

Typically, a plurality of assay mixtures are run in parallel with different compound or composition concentrations to obtain a different response to the various concentrations. Typically, one of these concentrations serves as a negative control, i.e., at zero concentration of agent or at a concentration of agent below the limits of assay detection.

Assays can be and preferably are conducted in parallel, such as by testing compounds on cells grown in multiwell plates such as 96-well or 384-well plates. In such assays, at a suitable time after addition of the assay components, the plate is moved, if necessary, so that assay wells are positioned for measurement of signal or for addition of additional components. Because a change in the signal may begin shortly after addition of test compounds, it is desirable to align the assay well with the signal detector as quickly as possible, with times of about two seconds or less being desirable. In preferred embodiments of the invention, where the apparatus is configured for detection through the bottom of the well(s) and compounds are added from above the well(s), readings may be taken substantially continuously, since the plate does not need to be moved for addition of reagent. The well and detector device should remain aligned for a predetermined period of time suitable to measure and record the change in signal.

The apparatus of the present invention is programmable to begin the steps of an assay sequence in a predetermined first well (or rows or columns of wells) and proceed sequentially down the columns and across the rows of the plate in a predetermined route through well number n. It is preferred that the data from replicate wells treated with the same compound are collected and recorded (e.g., stored in the memory of a computer) for calculation of signal.

To accomplish rapid compound addition and rapid reading of the response, the detector can be modified by fitting an automatic pipetter and developing a software program to accomplish precise computer control over both the detector and the automatic pipetter. By integrating the combination of a detection device and the automatic pipetter and using a microcomputer to control the commands to the detector and automatic pipetter, the delay time between reagent addition and detector reading can be significantly reduced. Moreover, both greater reproducibility and higher signal-to-noise ratios can be achieved as compared to manual addition of reagent because the computer repeats the process precisely time after time. Moreover, this arrangement permits a plurality of assays to be conducted concurrently without operator intervention. Thus, with automatic delivery of reagent followed by multiple signal measurements, reliability of the assays as well as the number of assays that can be performed per day are advantageously increased.

Candidate (test) compounds and compositions can be derived from, for example, combinatorial peptide libraries, small molecule libraries, or natural product libraries, including libraries based on the structure(s) of known inhibitors as described elsewhere herein. Candidate compounds and compositions encompass numerous chemical classes, although typically they are organic compounds. Preferably, the candidate pharmacological agents are small organic compounds, i.e., those having a molecular weight of more than 50 yet less than about 2500. Candidate compounds and compositions comprise functional chemical groups necessary for structural interactions with polypeptides (e.g., enzyme active sites), and typically include at least an amine, carbonyl, hydroxyl or carboxyl group, preferably at least two of the functional chemical groups and more preferably at least three of the functional chemical groups. The candidate agents can comprise cyclic carbon or heterocyclic structure and/or aromatic or polyaromatic structures substituted with one or more of the above-identified functional groups. Candidate agents also can be biomolecules such as peptides, saccharides, fatty acids, sterols, isoprenoids, nucleic acids, purines, pyrimidines, derivatives or structural analogs of the above, or combinations thereof and the like. Where the agent is a nucleic acid, the agent typically is a DNA or RNA molecule, although modified nucleic acids having non-natural bonds or subunits are also contemplated.

Candidate agents are obtained from a wide variety of sources including libraries of synthetic or natural compounds. For example, numerous methods are available and known to one of ordinary skill in the art for random and directed synthesis of a wide variety of organic compounds and biomolecules, including expression of randomized oligonucleotides, random or non-random peptide libraries, synthetic organic combinatorial libraries, phage display libraries of random peptides, and the like. Alternatively, libraries of natural compounds in the form of bacterial, fungal, plant and animal extracts are available or readily produced. Additionally, natural and synthetically produced libraries and compounds can be readily be modified through conventional chemical, physical, and biochemical means. Further, known pharmacological agents may be subjected to directed or random chemical modifications such as acylation, alkylation, esterification, amidification, etc. to produce structural analogs of the agents.

Pharmaceutical Compositions and Routes of Administration

The compounds of the invention typically are administered as pharmaceutical compositions, which may routinely contain pharmaceutically acceptable concentrations of salt, buffering agents, preservatives, compatible carriers, adjuvants, and optionally other therapeutic ingredients. The nature of the pharmaceutical carrier and other components of the pharmaceutical composition will depend on the mode of administration.

The pharmaceuticals composition of the present invention may be administered by any means and route known to the skilled artisan in carrying out the treatment methods described herein. Preferred routes of administration include but are not limited to oral, parenteral, intratumoral, intramuscular, intranasal, intracranial, sublingual, intratracheal, inhalation, ocular, vaginal, and rectal.

The skilled person will know how to formulate the compounds of the invention in accordance with the solubility by selection of appropriate carriers, solubilizers, etc.

For oral administration, compounds useful in methods of the invention can be formulated readily by combining the compounds with pharmaceutically acceptable carriers well known in the art. Such carriers enable the compounds of the invention to be formulated as tablets, pills, dragees, capsules, liquids, gels, syrups, slurries, suspensions and the like, for oral ingestion by a subject to be treated. Pharmaceutical preparations for oral use can be obtained as solid excipient, optionally grinding a resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carboxymethylcellulose, and/or polyvinylpyrrolidone (PVP). If desired, disintegrating agents may be added, such as the cross-linked polyvinyl pyrrolidone, agar, or alginic acid or a salt thereof such as sodium alginate. Optionally the oral formulations may also be formulated in saline or buffers, e.g., EDTA for neutralizing internal acid conditions, or may be administered without any carriers.

For the compounds of the invention, the location of release may be the stomach, the small intestine (the duodenum, the jejunum, or the ileum), or the large intestine. One skilled in the art has available formulations which will not dissolve in the stomach, yet will release the material in the duodenum or elsewhere in the intestine. Preferably, the release will avoid the deleterious effects of the stomach environment, either by protection the compound or by release of the biologically active compound beyond the stomach environment, such as in the intestine. To ensure full gastric resistance a coating impermeable to at least pH 5.0 is desired. Examples of the more common inert ingredients that are used as enteric coatings are cellulose acetate trimellitate (CAT), hydroxypropylmethylcellulose phthalate (HPMCP), HPMCP 50, HPMCP 55, polyvinyl acetate phthalate (PVAP), Eudragit L30D, Aquateric, cellulose acetate phthalate (CAP), Eudragit L, Eudragit S, and Shellac. These coatings may be used as mixed films. A coating or mixture of coatings can also be used on tablets, which are not intended for protection against the stomach. This can include sugar coatings, or coatings which make the tablet easier to swallow. Capsules may consist of a hard shell (such as gelatin) for delivery of dry therapeutic powder; for liquid forms, a soft gelatin shell may be used. The shell material of cachets could be thick starch or other edible paper. For pills, lozenges, molded tablets or tablet triturates, moist massing techniques can be used.

The compounds of the invention can be included in the formulation as fine multi-particulates in the form of granules or pellets of particle size about 1 mm. The formulation of the material for capsule administration could also be as a powder, lightly compressed plugs or even as tablets. The pharmaceutical composition could be prepared by compression. Colorants and flavoring agents may all be included. For example, the compounds of the invention may be formulated (such as by liposome or microsphere encapsulation) and then further contained within an edible product, such as a refrigerated beverage containing colorants and flavoring agents. One may dilute or increase the volume of the pharmaceutical composition with an inert material. These diluents could include carbohydrates, especially mannitol, a-lactose, anhydrous lactose, cellulose, sucrose, modified dextrans and starch. Certain inorganic salts may be also be used as fillers including calcium triphosphate, magnesium carbonate and sodium chloride. Some commercially available diluents are Fast-Flo, Emdex, STA-Rx 1500, Emcompress and Avicell.

Disintegrants may be included in the formulation of the pharmaceutical composition into a solid dosage form. Materials used as disintegrates include but are not limited to starch, including the commercial disintegrant based on starch, Explotab. Sodium starch glycolate, Amberlite, sodium carboxymethylcellulose, ultramylopectin, sodium alginate, gelatin, orange peel, acid carboxymethyl cellulose, natural sponge and bentonite may all be used. Another form of the disintegrants are the insoluble cationic exchange resins. Powdered gums may be used as disintegrants and as binders and these can include powdered gums such as agar, Karaya or tragacanth. Alginic acid and its sodium salt are also useful as disintegrants. Binders may be used to hold the therapeutic agent together to form a hard tablet and include materials from natural products such as acacia, tragacanth, starch and gelatin. Others include methyl cellulose (MC), ethyl cellulose (EC) and carboxymethyl cellulose (CMC). Polyvinyl pyrrolidone (PVP) and hydroxypropylmethyl cellulose (HPMC) could both be used in alcoholic solutions to granulate the therapeutic. An anti-frictional agent may be included in the formulation of the therapeutic to prevent sticking during the formulation process. Lubricants may be used as a layer between the therapeutic and the die wall, and these can include but are not limited to; stearic acid including its magnesium and calcium salts, polytetrafluoroethylene (PTFE), liquid paraffin, vegetable oils and waxes. Soluble lubricants may also be used such as sodium lauryl sulfate, magnesium lauryl sulfate, polyethylene glycol of various molecular weights, Carbowax 4000 and 6000. Glidants that might improve the flow properties of the drug during formulation and to aid rearrangement during compression might be added. The glidants may include starch, talc, pyrogenic silica and hydrated silicoaluminate.

To aid dissolution of the compounds of the invention into the aqueous environment a surfactant might be added as a wetting agent. Surfactants may include anionic detergents such as sodium lauryl sulfate, dioctyl sodium sulfosuccinate and dioctyl sodium sulfonate. Cationic detergents might be used and could include benzalkonium chloride or benzethomium chloride. The list of potential non-ionic detergents that could be included in the formulation as surfactants are lauromacrogol 400, polyoxyl 40 stearate, polyoxyethylene hydrogenated castor oil 10, 50 and 60, glycerol monostearate, polysorbate 40, 60, 65 and 80, sucrose fatty acid ester, methyl cellulose and carboxymethyl cellulose. These surfactants could be present in the formulation of the compounds of the invention or derivative either alone or as a mixture in different ratios.

Pharmaceutical preparations which can be used orally include push-fit capsules made of gelatin, as well as soft, sealed capsules made of gelatin and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added. Microspheres formulated for oral administration may also be used. Such microspheres have been well defined in the art. All formulations for oral administration should be in dosages suitable for such administration.

For buccal administration, the compositions may take the form of tablets or lozenges formulated in conventional manner.

For administration by inhalation, the compounds of the invention may be conveniently delivered in the form of an aerosol spray presentation from pressurized packs or a nebulizer, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of e.g. gelatin for use in an inhaler or insufflator may be formulated containing a powder mix of the compound and a suitable powder base such as lactose or starch.

Also contemplated herein is pulmonary delivery of the compounds of the invention. The compounds of the invention may delivered to the lungs of a mammal while inhaling and traverses across the lung epithelial lining to the blood stream. Other reports of inhaled molecules include Adjei et al., 1990, Pharmaceutical Research, 7:565-569; Adjei et al., 1990, International Journal of Pharmaceutics, 63:135-144 (leuprolide acetate); Braquet et al., 1989, Journal of Cardiovascular Pharmacology, 13(suppl. 5):143-146 (endothelin-1); Hubbard et al., 1989, Annals of Internal Medicine, Vol. III, pp. 206-212 (a1-antitrypsin); Smith et al., 1989, J. Clin. Invest. 84:1145-1146 (a-1-proteinase); Oswein et al., 1990, "Aerosolization of Proteins", Proceedings of Symposium on Respiratory Drug Delivery II, Keystone, Colo., March, (recombinant human growth hormone); Debs et al., 1988, J. Immunol. 140:3482-3488 (interferon-g and tumor necrosis factor alpha) and Platz et al., U.S. Pat. No. 5,284,656 (granulocyte colony stimulating factor). A method and composition for pulmonary delivery of drugs for systemic effect is described in U.S. Pat. No. 5,451,569, issued Sep. 19, 1995 to Wong et al.

Contemplated for use in the practice of this invention are a wide range of mechanical devices designed for pulmonary delivery of therapeutic products, including but not limited to nebulizers, metered dose inhalers, and powder inhalers, all of which are familiar to those skilled in the art. Some specific examples of commercially available devices suitable for the practice of this invention are the Ultravent nebulizer, manufactured by Mallinckrodt, Inc., St. Louis, Mo.; the Acorn II nebulizer, manufactured by Marquest Medical Products, Englewood, Colo.; the Ventolin metered dose inhaler, manufactured by Glaxo Inc., Research Triangle Park, N.C.; and the Spinhaler powder inhaler, manufactured by Fisons Corp., Bedford, Mass. All such devices require the use of formulations suitable for the dispensing the compounds useful in methods of the invention. Typically, each formulation is specific to the type of device employed and may involve the use of an appropriate propellant material, in addition to the usual diluents, adjuvants and/or carriers useful in therapy. Also, the use of liposomes, microcapsules or microspheres, inclusion complexes, or other types of carriers is contemplated. Chemically modified compounds of the invention may also be prepared in different formulations depending on the type of chemical modification or the type of device employed. Formulations suitable for use with a nebulizer, either jet or ultrasonic, will typically comprise the compounds of the invention dissolved in water at a concentration of about 0.1 to 25 mg of biologically active compound. The formulation may also include a buffer and a simple sugar. The nebulizer formulation may also contain a surfactant, to reduce or prevent surface induced aggregation caused by atomization of the solution in forming the aerosol.

Formulations for use with a metered-dose inhaler device will generally comprise a finely divided powder containing the compounds of the invention suspended in a propellant with the aid of a surfactant. The propellant may be any conventional material employed for this purpose, such as a chlorofluorocarbon, a hydrochlorofluorocarbon, a hydrofluorocarbon, or a hydrocarbon, including trichlorofluoromethane, dichlorodifluoromethane, dichlorotetrafluoroethanol, and 1,1,1,2-tetrafluoroethane, or combinations thereof. Suitable surfactants include sorbitan trioleate and soya lecithin. Oleic acid may also be useful as a surfactant. Formulations for dispensing from a powder inhaler device will comprise a finely divided dry powder containing the compounds of the invention and may also include a bulking agent, such as lactose, sorbitol, sucrose, or mannitol in amounts which facilitate dispersal of the powder from the device, e.g., 50 to 90% by weight of the formulation. Compounds useful in methods of the invention should most advantageously be prepared in particulate form with an average particle size of less than 10 mm (or microns), most preferably 0.5 to 5 mm, for most effective delivery to the distal lung.

Nasal delivery of a pharmaceutical composition of the present invention is also contemplated. Nasal delivery allows the passage of a pharmaceutical composition of the present invention to the blood stream directly after administering the therapeutic product to the nose, without the necessity for deposition of the product in the lung. Formulations for nasal delivery include those with dextran or cyclodextran. For nasal administration, a useful device is a small, hard bottle to which a metered dose sprayer is attached. In one embodiment, the metered dose is delivered by drawing the pharmaceutical composition of the present invention solution into a chamber of defined volume, which chamber has an aperture dimensioned to aerosolize and aerosol formulation by forming a spray when a liquid in the chamber is compressed. The chamber is compressed to administer the pharmaceutical composition of the present invention. In a specific embodiment, the chamber is a piston arrangement. Such devices are commercially available. Alternatively, a plastic squeeze bottle with an aperture or opening dimensioned to aerosolize an aerosol formulation by forming a spray when squeezed is used. The opening is usually found in the top of the bottle, and the top is generally tapered to partially fit in the nasal passages for efficient administration of the aerosol formulation. Preferably, the nasal inhaler will provide a metered amount of the aerosol formulation, for administration of a measured dose of the drug.

Compounds useful in methods of the invention, when it is desirable to deliver them systemically, may be formulated for parenteral administration by injection, e.g., by bolus injection or continuous infusion. Formulations for injection may be presented in unit dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents. Pharmaceutical formulations for parenteral administration include aqueous solutions of the active compounds in water-soluble form. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran. Optionally, the suspension may also contain suitable stabilizers or agents which increase the solubility of the compounds to allow for the preparation of highly concentrated solutions.

The compounds may also be formulated in rectal or vaginal compositions such as suppositories or retention enemas, e.g., containing conventional suppository bases such as cocoa butter or other glycerides. In addition to the formulations described previously, the compounds may also be formulated as a depot preparation. Such long acting formulations may be formulated with suitable polymeric or hydrophobic materials (for example as an emulsion in an acceptable oil) or ion exchange resins, or as sparingly soluble derivatives, for example, as a sparingly soluble salt.

The pharmaceutical compositions also may comprise suitable solid or gel phase carriers or excipients. Examples of such carriers or excipients include but are not limited to calcium carbonate, calcium phosphate, various sugars, starches, cellulose derivatives, gelatin, and polymers such as polyethylene glycols.

Suitable liquid or solid pharmaceutical preparation forms are, for example, aqueous or saline solutions for inhalation, microencapsulated, encochleated, coated onto microscopic gold particles, contained in liposomes, nebulized, aerosols, pellets for implantation into the skin, or dried onto a sharp object to be scratched into the skin. The pharmaceutical compositions also include granules, powders, tablets, coated tablets, (micro)capsules, suppositories, syrups, emulsions, suspensions, creams, drops or preparations with protracted release of active compounds, in whose preparation excipients and additives and/or auxiliaries such as disintegrants, binders, coating agents, swelling agents, lubricants, flavorings, sweeteners or solubilizers are customarily used as described above. The pharmaceutical compositions are suitable for use in a variety of drug delivery systems. For a brief review of methods for drug delivery, see Langer, 1990, Science 249, 1527-1533, which is incorporated herein by reference.

The compounds useful in methods of the invention, and optionally other therapeutics, including other anti-cancer compounds may be administered per se (neat) or in the form of a pharmaceutically acceptable salt. When used in medicine the salts should be pharmaceutically acceptable, but non-pharmaceutically acceptable salts may conveniently be used to prepare pharmaceutically acceptable salts thereof. Such salts include, but are not limited to, those prepared from the following acids: hydrochloric, hydrobromic, sulphuric, nitric, phosphoric, maleic, acetic, salicylic, p-toluene sulphonic, tartaric, citric, methane sulphonic, formic, malonic, succinic, naphthalene-2-sulphonic, and benzene sulphonic. Also, such salts can be prepared as alkaline metal or alkaline earth salts, such as sodium, potassium or calcium salts of the carboxylic acid group.

Suitable buffering agents include: acetic acid and a salt (1-2% w/v); citric acid and a salt (1-3% w/v); boric acid and a salt (0.5-2.5% w/v); and phosphoric acid and a salt (0.8-2% w/v). Suitable preservatives include benzalkonium chloride (0.003-0.03% w/v); chlorobutanol (0.3-0.9% w/v); parabens (0.01-0.25% w/v) and thimerosal (0.004-0.02% w/v).

The pharmaceutical compositions of the invention contain an effective amount of one or more compounds useful in methods of the invention and optionally additional therapeutic agents included in a pharmaceutically-acceptable carrier. The term pharmaceutically-acceptable carrier means one or more compatible solid or liquid filler, diluents or encapsulating substances which are suitable for administration to a human or other vertebrate animal. The term carrier denotes an organic or inorganic ingredient, natural or synthetic, with which the active ingredient is combined to facilitate the application. The components of the pharmaceutical compositions also are capable of being commingled with the compounds of the present invention, and with each other, in a manner such that there is no interaction which would substantially impair the desired pharmaceutical efficiency.

The compounds of the invention may be provided in particles. Particles as used herein means nano or microparticles (or in some instances larger) which can consist in whole or in part of the compounds of the invention or the other therapeutic agent(s) as described herein. The particles may contain the therapeutic agent(s) in a core surrounded by a coating, including, but not limited to, an enteric coating. The therapeutic agent(s) also may be dispersed throughout the particles. The therapeutic agent(s) also may be adsorbed into the particles. The particles may be of any order release kinetics, including zero order release, first order release, second order release, delayed release, sustained release, immediate release, and any combination thereof, etc. The particle may include, in addition to the therapeutic agent(s), any of those materials routinely used in the art of pharmacy and medicine, including, but not limited to, erodible, non-erodible, biodegradable, or nonbiodegradable material or combinations thereof. The particles may be microcapsules which contain the compounds of the invention in a solution or in a semi-solid state. The particles may be of virtually any shape.

Both non-biodegradable and biodegradable polymeric materials can be used in the manufacture of particles for delivering the therapeutic agent(s). Such polymers may be natural or synthetic polymers. The polymer is selected based on the period of time over which release is desired. Bioadhesive polymers of particular interest include bioerodible hydrogels described by Sawhney et. al., 1993, Macromolecules 26, 581-587, the teachings of which are incorporated herein. These include polyhyaluronic acids, casein, gelatin, glutin, polyanhydrides, polyacrylic acid, alginate, chitosan, poly(methyl methacrylates), poly(ethyl methacrylates), poly(butylmethacrylate), poly(isobutyl methacrylate), poly(hexylmethacrylate), poly(isodecyl methacrylate), poly(lauryl methacrylate), poly(phenyl methacrylate), poly(methyl acrylate), poly(isopropyl acrylate), poly(isobutyl acrylate), and poly(octadecyl acrylate).

The compounds useful in methods of the invention may be contained in controlled release systems. The term "controlled release" is intended to refer to any compound of the invention-containing formulation in which the manner and profile of compound release from the formulation are controlled. This refers to immediate as well as non-immediate release formulations, with non-immediate release formulations including but not limited to sustained release and delayed release formulations. The term "sustained release" (also referred to as "extended release") is used in its conventional sense to refer to a drug formulation that provides for gradual release of a compound over an extended period of time, and that preferably, although not necessarily, results in substantially constant blood levels of a drug over an extended time period. The term "delayed release" is used in its conventional sense to refer to a drug formulation in which there is a time delay between administration of the formulation and the release of the compound there from. "Delayed release" may or may not involve gradual release of a compound over an extended period of time, and thus may or may not be "sustained release." Use of a long-term sustained release implant may be particularly suitable for treatment of chronic conditions. "Long-term" release, as used herein, means that the implant is constructed and arranged to deliver therapeutic levels of the active ingredient for at least 7 days, and preferably 30-60 days. Long-term sustained release implants are well-known to those of ordinary skill in the art and include some of the release systems described above.

Kits

In one aspect the invention provides kits comprising a pharmaceutical composition comprising a therapeutically effective amount of one or more compounds useful in methods of the invention and instructions for administration of the pharmaceutical composition. In some aspects of the invention, the kit can include a pharmaceutical preparation vial, a pharmaceutical preparation diluent vial, and the compound(s) useful in methods of the invention. The diluent vial contains a diluent such as physiological saline for diluting what could be a concentrated solution or lyophilized powder of the compound(s) useful in methods of the invention. In some embodiments, the instructions include instructions for mixing a particular amount of the diluent with a particular amount of the concentrated pharmaceutical preparation, whereby a final formulation for injection or infusion is prepared. In some embodiments, the instructions include instructions for use in a syringe or other administration device. In some embodiments, the instructions include instructions for treating a patient with an effective amount of the compounds useful in methods of the invention. It also will be understood that the containers containing the preparations, whether the container is a bottle, a vial with a septum, an ampoule with a septum, an infusion bag, and the like, can contain indicia such as conventional markings which change color when the preparation has been autoclaved or otherwise sterilized.

The present invention is further illustrated by the following Examples, which in no way should be construed as further limiting. The entire contents of all of the references (including literature references, issued patents, published patent applications, and co-pending patent applications) cited throughout this application are hereby expressly incorporated by reference, in particular for the teaching that is referenced hereinabove.

EXAMPLES

Methods

Cell Culture, Isotopic Labeling, and Hypoxia. All cell lines were cultured in Dulbecco's Modified Eagle Medium (DMEM; Mediatech) containing 10% fetal bovine serum (FBS; Invitrogen) and 100 U/ml penicillin/streptomycin (P/S; Mediatech) unless otherwise mentioned. Cell lines were obtained from ATCC unless otherwise noted. The VC3 glioma cell line was provided by Tim Lautenschlaeger (Ohio State University), MDA-MB-231 and HCT116 cell lines were provided by Ferdinando Chiaradonna (University of Milano-Bicocca), MRC5 cells were provided by Stephen Lippard (MIT), SN12C, ACHN, and 786-O cells were provided by Kevin Courtney and Lew Cantley (Harvard Medical School), and MCF10A cells were provided by Joan Brugge (Harvard Medical School), and Huh7 cells were provided by Mike Hemann (MIT). MCF10A cells were cultured in custom DMEM/F12 (Hyclone) containing 5% horse serum, 20 ng/ml EGF, 10 μg/ml insulin, 100 ng/ml cholera toxin, 0.5 mg/ml hydrocortisone, 100 U/ml penicillin/streptomycin, and labeled/unlabeled glucose and glutamine at 18 mM and 2.5 mM, respectively. PRC3, WT8, pTV, and pTR cell lines were subcloned from the 786-O cell line as previously described (42, 43). For isotopic labeling experiments, cells were cultured in 6 well plates in glucose- and glutamine-free DMEM (Sigma) containing 10% dialyzed FBS (Invitrogen), 100 U/ml P/S, naturally labeled glucose or glutamine, and the appropriate tracer, including [U-$^{13}C_5$]glutamine (Isotec), [5-$^{13}C$]glutamine (C/D/N Isotopes), [1-$^{13}C$]glutamine, [U-$^{13}C_6$]glucose, [1,2-$^{13}C_2$]glucose (all from Cambridge Isotope Labs). Steady state labeling of organic and amino acids was accomplished by culturing subconfluent cells in tracer medium for 24 hours. Labeling of fatty acids for Isotopomer Spectral Analysis (USA) was conducted over 3-5 days of culture in an excess of tracer medium (3-4 ml/well in a 6 well plate) to prevent nutrient depletion. Hypoxic culture was conducted by feeding a custom mixture of 1% $O_2$, 5% $CO_2$, and 94% $N_2$ to a standard incubator controlled at 5% $CO_2$. HEPES (Mediatech) was added to the culture medium at 20 mM to maintain pH between normoxic and hypoxic cultures. The internal gas content was monitored using Fyrite gas analyzers (Bacharach) for $CO_2$ and $O_2$. $O_2$ levels were confirmed at 1.5-2% during hypoxic culture.

Stable cell cultures with decreased IDH1 and IDH2 expression were generated via lentiviral-mediated shRNA expression. pLKO.1 lentiviral vectors targeting IDH1 with shRNA sequences of CCGGGCTGCTTGCAT-TAAAGGTTTACTCGAGTAAACCTTTAATGCAAGCA-GCTTT TT (IDH1a; TRCN0000027298; SEQ ID NO:1) and CCGGCGAATCATTTGGGAATTGATTCTCGAGAAT-CAATTCCCAAATGATTCGTTT TT (IDH1b; TRCN0000027289; SEQ ID NO:2), IDH2 with shRNA sequence CCGGGTGGACATCCAGCTAAAGTATCTC-GAGATACTTTAGCTGGATGTCCACTTT TT (TRCN0000027225; SEQ ID NO:3). For controls, either non-targeting control shRNA (SHC002; Sigma) or pLKO.1 scrambled control vector (44)(Addgene) were used. pLKO.1 vector targeting ARNT with shRNA sequence CCGGGA-GAAGTCAGATGGTTTATTTCTCGAGAAATAAAC-CATCTGACTTCTCTTT TT (TRCN0000003819; SEQ ID NO:4) was obtained from Open Biosystems.

HEK293T cells were co-transfected with pLKO.1 vectors and packaging plasmids to produce lentivirus. Filtered supernatants were used for infection, and cells were selected with puromycin (2 µg/ml) for at least two passages before initiating tracer and flux experiments.

Metabolite Extraction and Gas Chromatography/Mass Spectrometry (GC/MS) Analysis. At the conclusion of culture, cells were rinsed with 1 ml ice cold PBS and quenched with 0.4 ml ice cold methanol. An equal volume of water was added, and cells were collected in tubes by scraping with a pipette. One volume of ice cold chloroform was added to each tube, and the extracts were vortexed at 4° C. for 30 minutes. Samples were centrifuged at 14,000 g for 5 minutes at room temperature. For analysis of polar metabolites, the aqueous phase was transferred to a new tube for evaporation under airflow. For ISA experiments, the nonpolar fraction was collected and evaporated under airflow. In some ISA experiments, cells were trypsinized, counted, and pelleted prior to lipid extraction as described above.

Dried polar metabolites were dissolved in 20 µl of 2% methoxyamine hydrochloride in pyridine (Pierce) and held at 37° C. for 1.5 hours. After dissolution and reaction, tert-butyldimethylsilyl (TBDMS) derivatization was initiated by adding 30 µl N-methyl-N-(tert-butyldimethylsilyl) trifluoroacetamide (MBTSTFA)+1% tert-butyldimethylchlorosilane (TBDMCS; Pierce) and incubating at 55° C. for 1 hour. Fatty acid methyl esters (FAMEs) were generated by dissolving and reacting dried chloroform fractions in 50-100 µl of Methyl-8 reagent (Pierce) and incubating at 60° C. for 1 hour. GC/MS analysis was performed using an Agilent 6890 GC equipped with a 30 m DB-35MS capillary column connected to an Agilent 5975B MS operating under electron impact (EI) ionization at 70 eV. One µl of sample was injected in splitless mode at 270° C., using helium as the carrier gas at a flow rate of 1 ml $min^{-1}$. For measurement of organic and amino acids, the GC oven temperature was held at 100° C. for 3 min and increased to 300° C. at 3.5° $min^{-1}$. For analysis of FAMEs, the GC temperature was held at 100° C. for 5 minutes after injection, increased to 200° C. at 15° $min^{-1}$, then to 250° C. at 5° $min^{-1}$, and finally to 300° C. at 15° $min^{-1}$. The MS source and quadrupole were held at 230° C. and 150° C., respectively, and the detector was run in scanning mode, recording ion abundance in the range of 100-605 m/z. Mass isotopomer distributions (MIDs) were determined by integrating the appropriate ion fragments listed in Table 1. When required, MIDs were corrected for natural isotope abundance using in house algorithms adapted from Fernandez et al. (45).

Figure 24A:
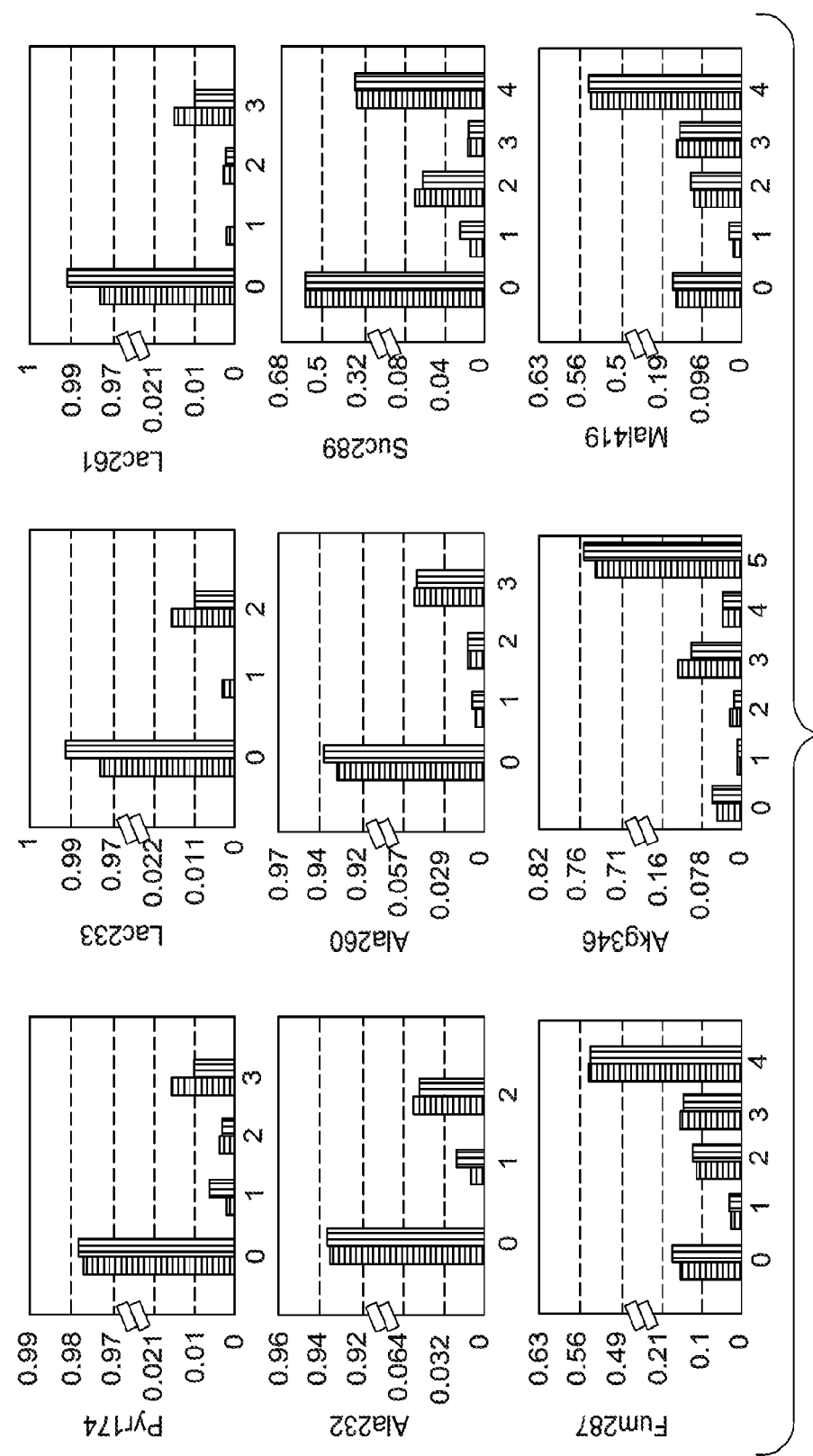
FIG. 24. Simulated and measured MIDs from MFA in A549 cells expressing non-targeting control shRNAs. Simulated values were obtained using Metran and the model fit listed in Table 3. Cells were cultured as described in Methods using [U-$^{13}$C5]glutamine and metabolite labeling was quantified via GC/MS. MIDs are corrected for natural abundance. From left in each set of bars: normoxia (blue/light grey bars) and hypoxia (red/dark grey bars).
Figure 24B:
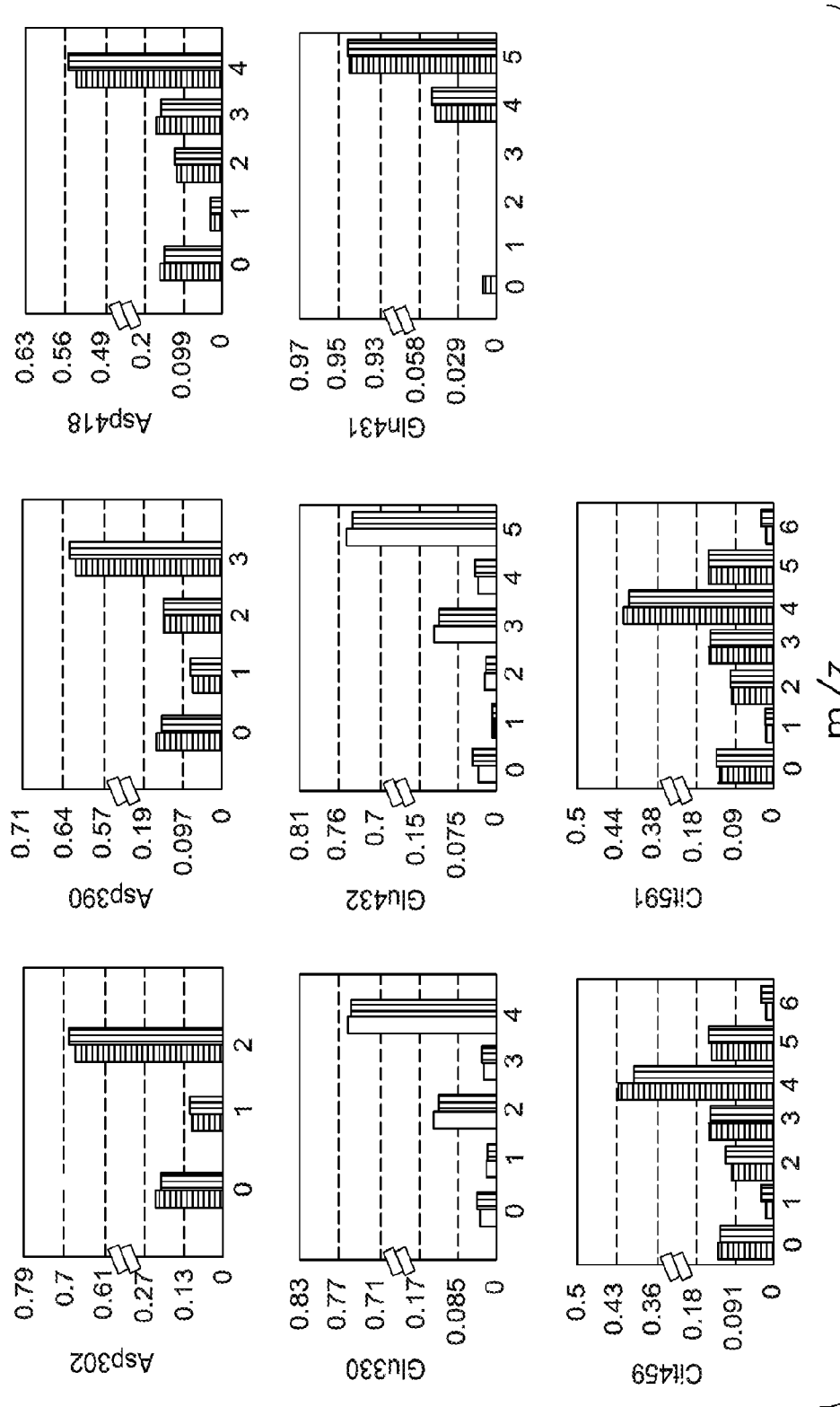
Figure 25A:
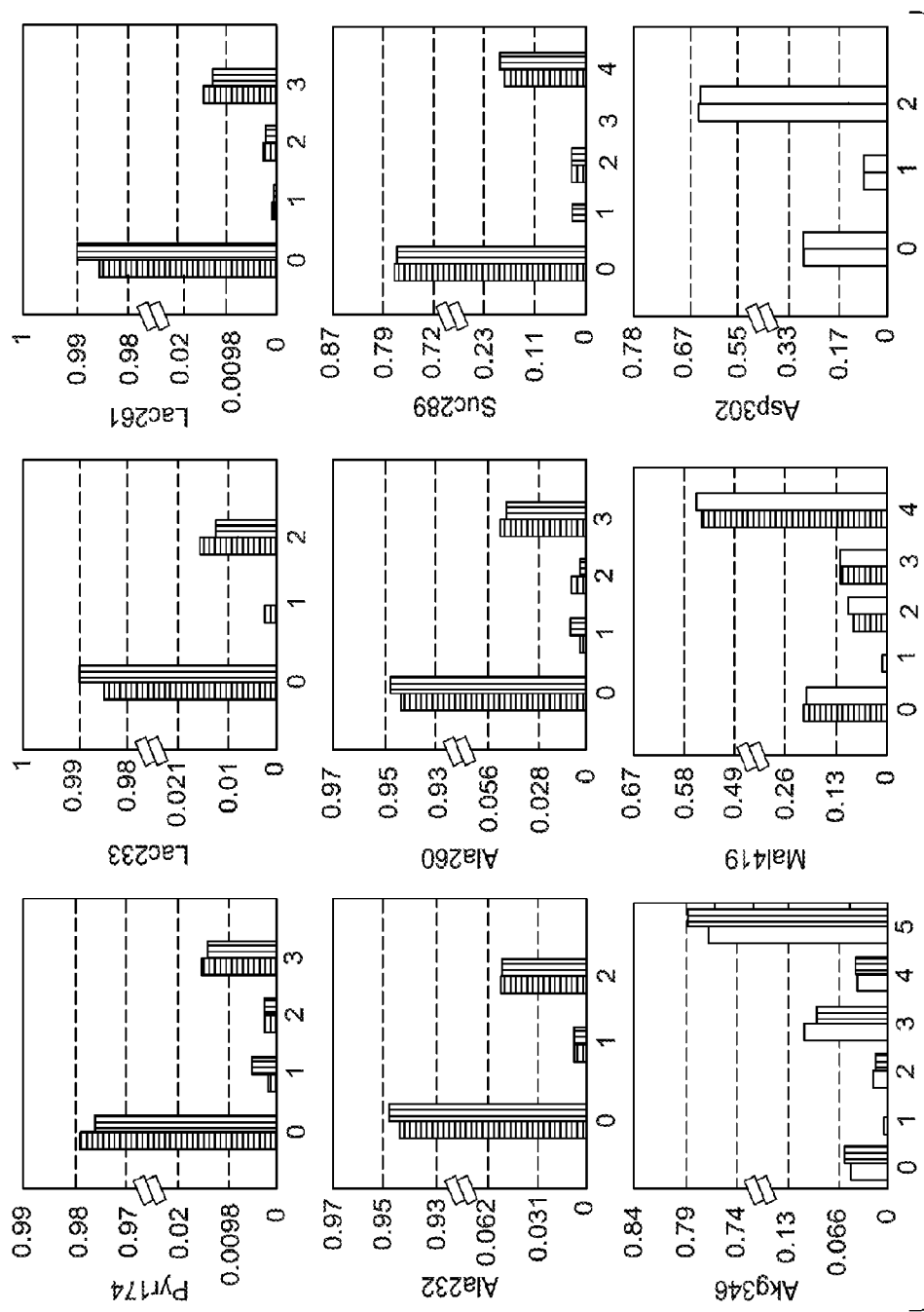
FIG. 25. Simulated and measured MIDs from MFA in A549 cells expressing IDH1a shRNAs. Simulated values were obtained using Metran and the model fit listed in Table 4. Cells were cultured as described in Methods using [U-$^{13}$C5]glutamine and metabolite labeling was quantified via GC/MS. MIDs are corrected for natural abundance. From left in each set of bars: normoxia (blue/light grey bars) and hypoxia (red/dark grey bars).
Figure 25B:
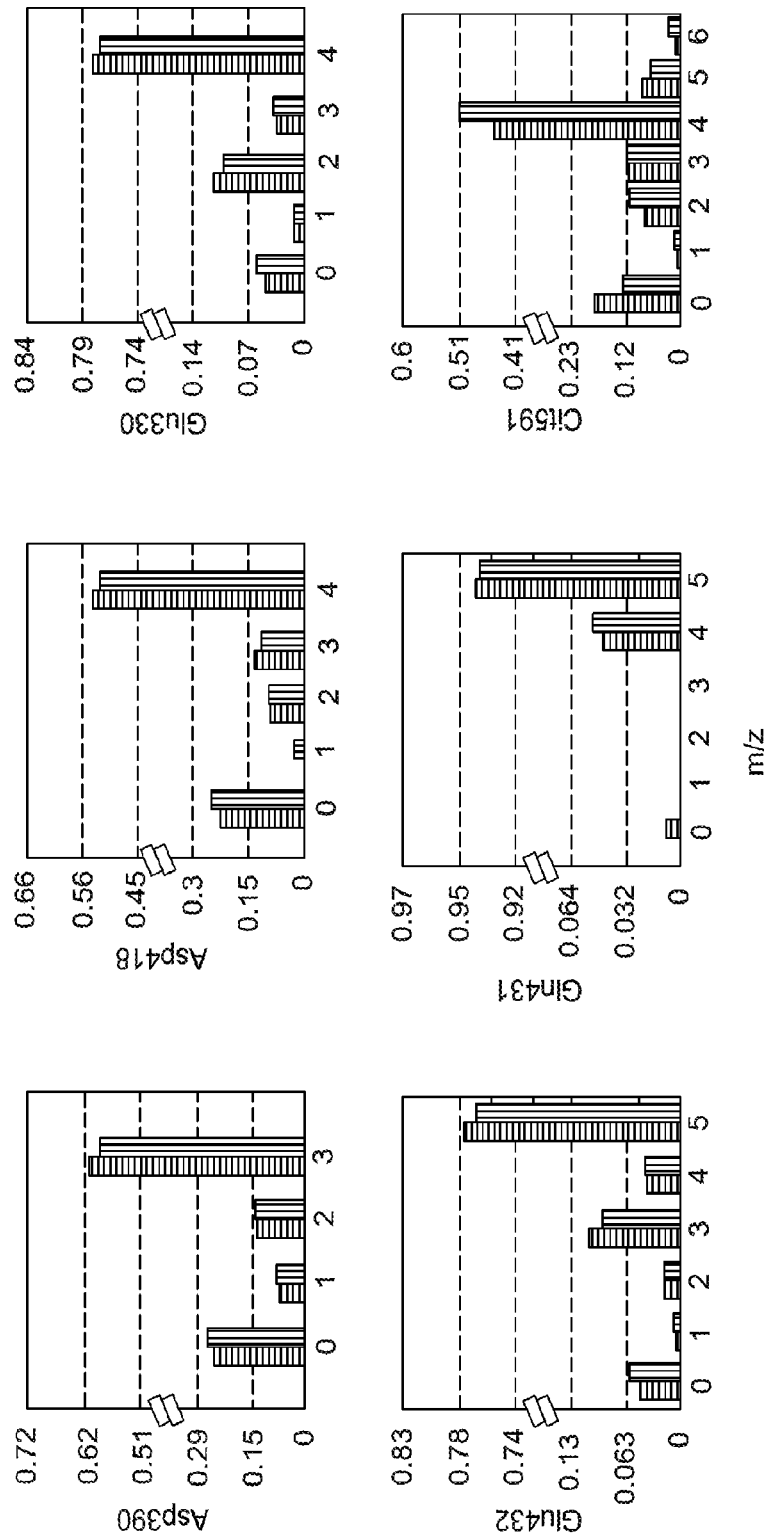
Figure 26A:
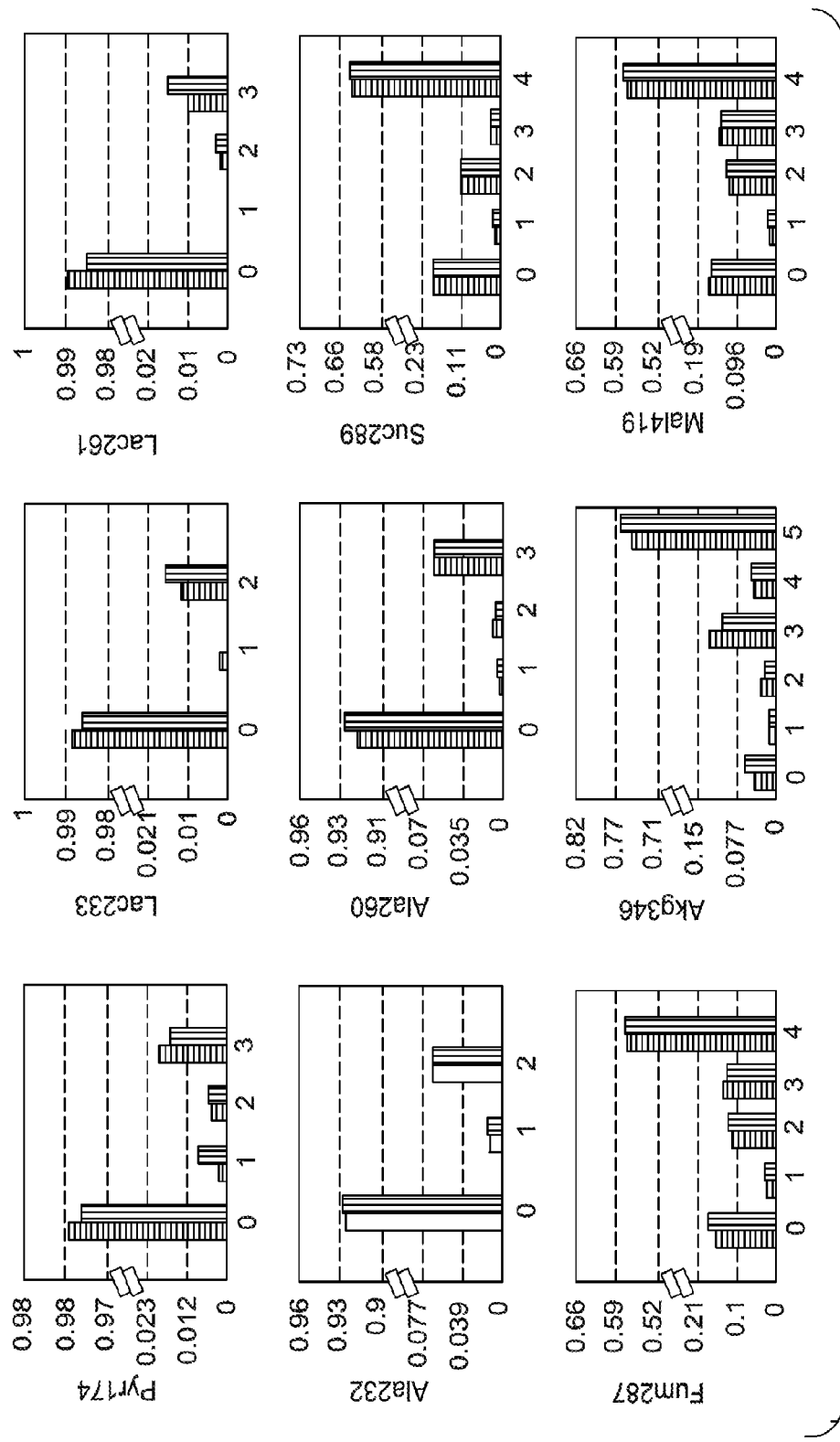
FIG. 26. Simulated and measured MIDs from MFA in A549 cells expressing IDH1b shRNAs. Simulated values were obtained using Metran and the model fit listed in Table 5. Cells were cultured as described in Methods using [U-$^{13}$C5]glutamine and metabolite labeling was quantified via GC/MS. MIDs are corrected for natural abundance. From left in each set of bars: normoxia (blue/light grey bars) and hypoxia (red/dark grey bars).
Figure 26B:
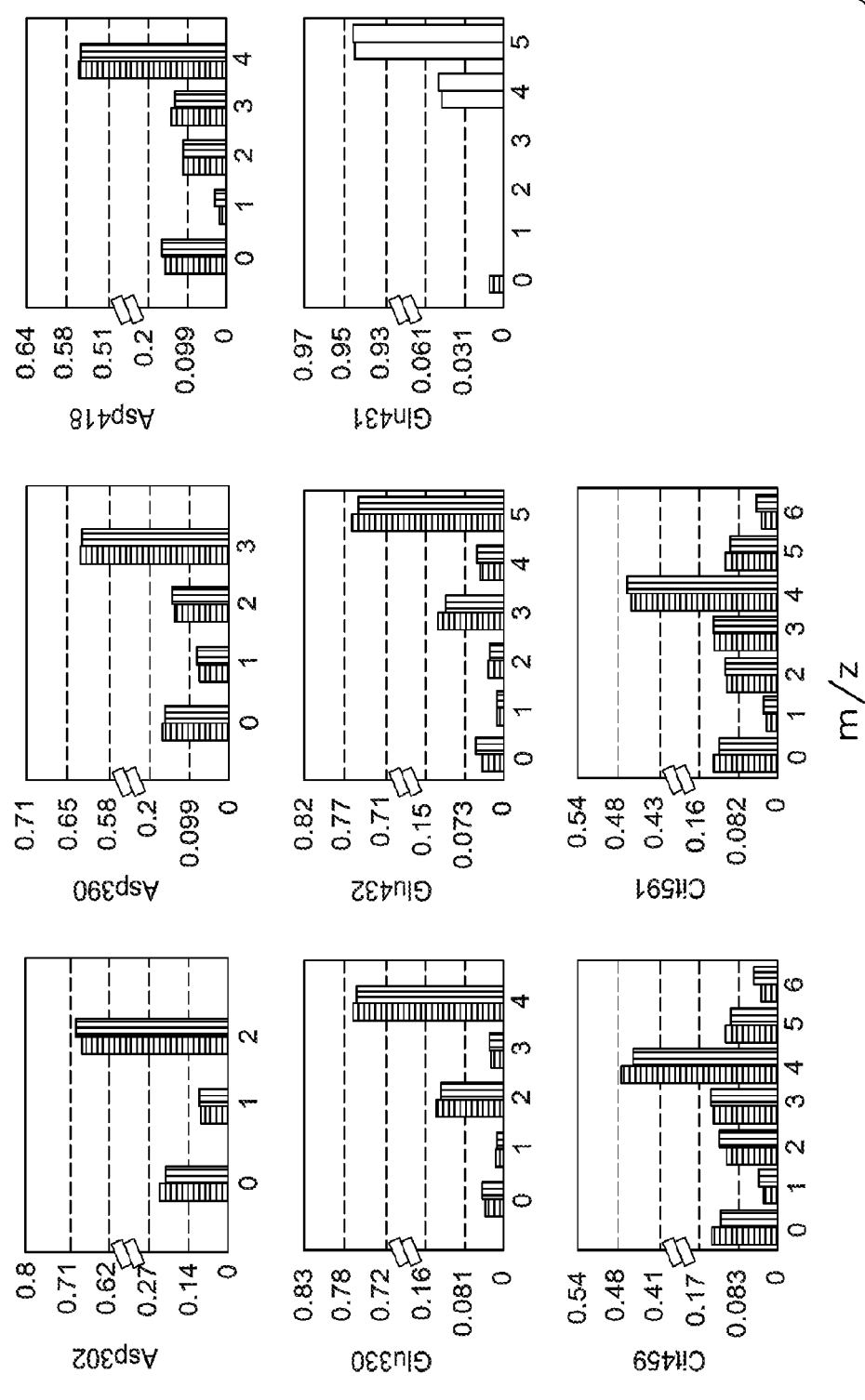

ISA and Metabolic Flux Analysis. Computational estimation of fluxes or % enrichment in the AcCoA pool and their associated 95% confidence intervals were accomplished using the elementary metabolite unit- (EMU-) based software Metran, executed within Matlab (Mathworks) as previously described (24, 46-48). Briefly, fluxes were determined iteratively by simulating MS measurements from a given flux vector and comparing to MID measurements (three biological replicates). Upon obtaining an acceptable fit, confidence intervals were determined for each flux using parameter continuation. Assumptions, network (including atom transitions), raw data, and model fits are presented as supplemental data (see Tables 3-5 and FIGS. 24-26). ISA was performed in a similar manner using the simple network described in FIG. 7 and Table 6 to determine the tracer enrichment in lipogenic AcCoA (D value) and percentage of newly synthesized lipids and de novo lipogenesis, g(t) (7, 30). Uncorrected MIDs, fitted parameters, and confidence intervals used for ISA are listed as supplemental data (see Tables 3-5).

For calculation of absolute flux of tracers to palmitate in biomass, the quantity of newly synthesized palmitate was determined by multiplying the fractional newly synthesized palmitate value (g(t) value from ISA) by the total cellular palmitate. Palmitate was quantitated by GC/MS using a triheptadecanoin internal standard. Flux of a given tracer to palmitate was calculated by multiplying the tracer contribution (D value from ISA) by the amount of newly synthesized palmitate and dividing by the integral viable cell density over the course of the experiment.

Metabolic Flux Analysis (MFA): Description and Assumptions

MFA was conducted using the elementary-metabolite unit (EMU-) based software package Metran as previously described (24, 26, 47, 48). Flux estimations and confidence intervals are subject to the following assumptions:

1. Cellular metabolism and isotopic labeling are at steady state. Cells were selected in the presence of puromycin for at least 2 passages and labeled for 24 hours with [U-$^{13}C_5$] glutamine. Labeling of glycolytic and TCA cycle intermediates has been demonstrated to be constant after such time (23, 25).

2. Dissolved $CO_2$ exchanges freely with gaseous $CO_2$ such that unlabeled $CO_2$ is available for use in carboxylation reactions.

3. Fatty acid oxidation and protein turnover are negligible relative to glucose and glutamine consumption.

4. Two separate compartments of pyruvate are assumed to exist, with cytosolic pyruvate (primarily glucose derived) used to generate lactate and mitochondrial pyruvate (derived from TCA cycle metabolites) used for alanine synthesis. These compartments are exchangeable and required to fit the differential labeling observed in lactate and alanine. The former being primarily glucose derived, and the latter containing more label from glutamine.

5. Fumarate and succinate are symmetric metabolites, and a dilution pool of unlabeled succinate is assumed to exist. Isotopic enrichment of succinate pools from tracers is often observed to be decreased in tracer studies. Such effects have been hypothesized to be caused by intracellular compartmentalization (51). This pool is modeled by inclusion of a dilution flux and does not participate in central carbon metabolism. Measured succinate is comprised of both pools (metabolically active and dilution compartment).

6. The pentose phosphate pathway (PPP) is included in the network. The percentage of glycolytic flux that proceeds through the oxidative PPP branch was determined via the M1/M2 ratio of lactate in control or IDH1 knockdown A549 cells cultured with [1,2-$^{13}C_2$]glucose (52). No significant change was observed between control and knockdown cells.

7. Amino acid and fatty acid fluxes to biomass were determined by quantifying per cell metabolites of A549 protein hydrolysates (aspartate, glutamate, alanine) or chloroform extracts (palmitate, oleate, stearate). These values were multiplied by the observed growth rate, μ, to obtain fluxes.

Isotopic labeling was quantified in the metabolite ion fragments listed in Table 1. In the case of redundant fragment measurements, mass isotopomer distributions (MIDs) were highly reproducible (i.e. within 1-2%). The formulas listed herein (see also Fernandez et al. (45)) were used to correct for natural isotope abundance.

Metabolite Analysis of Spent Medium. Glucose, lactate, glutamine, and glutamate concentrations were measured in fresh and spent medium samples using a Yellow Springs Instruments (YSI) 7100. Cell number was determined using a hemocytometer. Extracellular flux measurements were calculated by assuming exponential growth over the culture period to determine integral viable cell density.

Purification of Recombinant IDH1. His-tagged IDH1 in pET41a was transformed into E. Coli (BL21 plysS DE3) and cells were grown with kanamycin selection to an $OD_{600}$ of 0.6. The cells were then moved to 18° C. and induced with 1 mM IPTG for 16-18 hours, pelleted and subjected to freeze/thaw prior to resuspension in 60 ml lysis buffer (20 mM Tris, pH 7.4, 0.1% Triton X-100, 500 mM NaCl, 5 mM β-mercaptoethanol, 10% glycerol, supplemented with protease inhibitors). Cells were lysed by sonication and protein bound to Ni-NTA agarose. The beads were batch washed 3-4× with wash buffer (20 mM Tris, pH 7.4, 500 mM NaCl, 5 mM β-mercaptoethanol, 10% glycerol), then eluted from a column in 1 mL fractions with elution buffer (20 mM Tris, pH 7.4, 500 mM NaCl, 5 mM β-mercaptoethanol, 500 mM imidazole, 10% glycerol). The first and second fractions containing the majority of the protein were dialyzed into 50 mM Tris pH 7.5, 200 mM NaCl, 5 mM β-mercaptoethanol, 2 mM $MnCl_2$, 10% glycerol and the recombinant enzyme was stored at −80° C.

Recombinant IDH1 Enzyme Assays. All reactions were performed in reaction buffer (100 mM Tris pH 7.5, 1.3 mM $MnCl_2$, 200 uM NADPH and 2 mM α-ketoglutarate) which was equilibrated overnight at 0%, 5%, or 10% $CO_2$ as indicated. 100 ul of reaction buffer for each $CO_2$ condition was added to 10 μg rIDH1 and activity was measured by following NADPH fluorescence (excitation at 340 nm, emission at 460 nm).

NADP+ and NADPH Quantification Assay. NADP+ and NADPH values were determined using the Fluoro NADP/NADPH detection kit according to manufacturer's instructions (Cell Technology Inc.) and were expressed as the ratio of NADPH to NADP+ levels. Concentrations were determined in proliferating, subconfluent cultures via fluorescence measurements (excitation at 550 nm, emission at 595 nm) using a standard curve.

Luciferase Assays. Subconfluent cells in 6 well plates were co-transfected with 1 μg of a firefly luciferase vector and 50 ng Renilla luciferase vector (pRL-TK; Promega) using Fugene 6 reagent. The ODD-Luciferase and Luciferase vectors were obtained from Addgene and based off of the pcDNA3.1 vector (49). Hypoxia responsive element-luciferase (HRE-Luc) vectors were used as described (50). Approximately 24 hours after transfection, medium was changed and cells were placed under normoxia, hypoxia, or treated with 1 mM dimethyloxalylglycine (DMOG). After 18 hours of treatment, cells were lysed and luciferase activity was determined using the Dual Luciferase Reporter Assay system (Promega) according to the manufacturer's instructions.

SDS-PAGE and Western Blotting. Cells were rinsed with ice cold PBS and lysed using RIPA buffer. Proteins were separated by SDS-PAGE and transferred to a nitrocellulose membrane. After blocking, membranes were probed with goat anti-IDH1 polyclonal antibody (Santa Cruz Biotechnology, sc49996), mouse anti-HIF1α monoclonal antibody (BD Biosciences, 610959), rabbit anti-HIF2α polyclonal antibody (Novus Biologicals, NB100-122), mouse anti-ARNT1 monoclonal antibody (BD Biosciences, 611079), mouse anti-β-actin mouse monoclonal antibody (Novus Biologicals, ab8226), mouse anti-tubulin monoclonal antibody (Sigma), or rabbit anti-tubulin antibody (Sigma). Protein was detected using horseradish peroxidase-conjugated secondary antibodies and chemiluminescence.

Abbreviations:

Acetyl coenzyme A, AcCoA; α-ketoglutarate, aKG; alanine, Ala; aspartate, Asp; citrate, Cit; fumarate, Fum; glutamine, Gln; glutamate, Glu; malate, Mal; oxaloacetate, Oac; lactate, Lac; pyruvate, Pyr, succinate, Suc; palmitate, Palm; glucose, Glc; glucose-6-phosphate, G6P, fructose-6-phosphate, F6P, dihydroxyacetone phosphate, DHAP; glyceraldehyde phosphate, GAP; 3-phosphoglycerate, 3PG; pentose-5-phosphate, P5P; erythrose-4-phosphate, E4P; sedoheptulose-7-phosphate, S7P.

Example 1

Figure 1B:
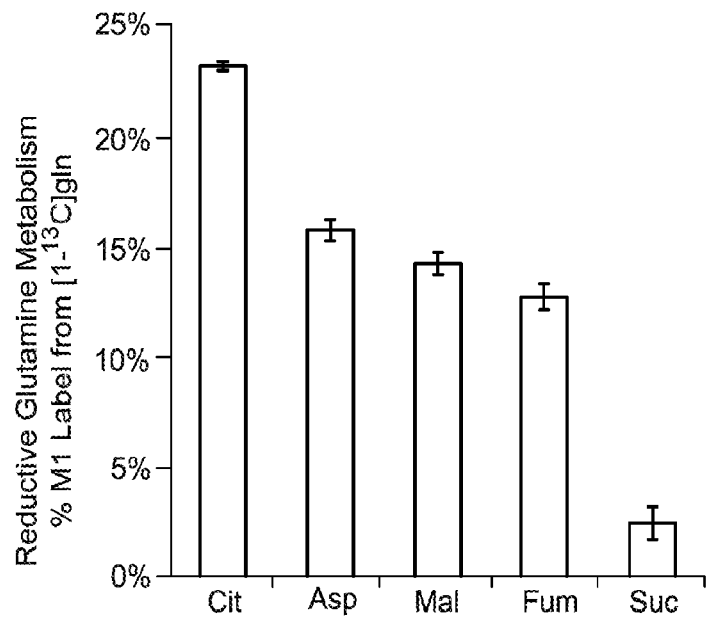
Figure 7:
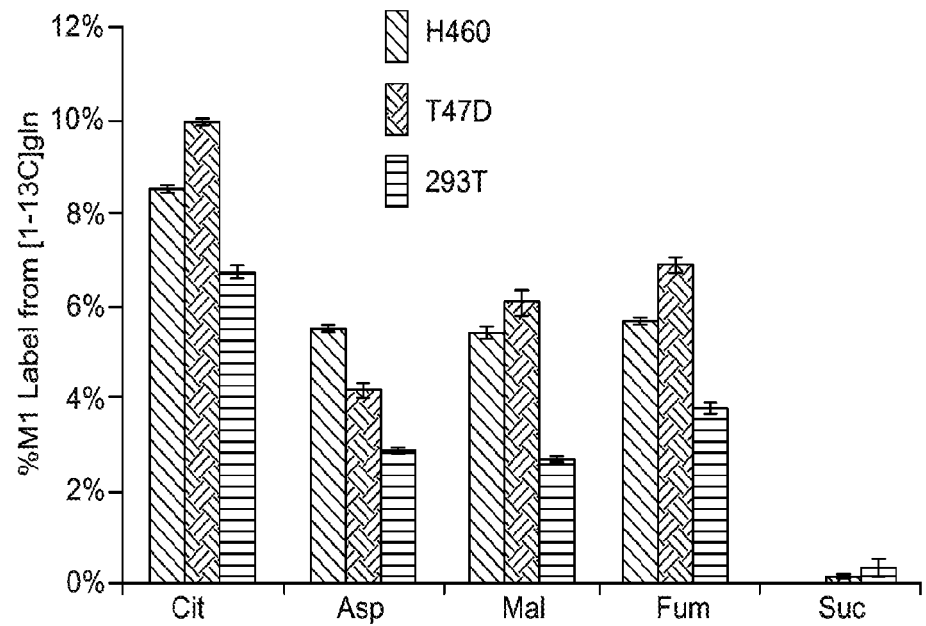
FIG. 7. Evidence for reductive carboxylation in tumor cell lines using [1-$^{13}$C]glutamine tracer. Percentage of M1 label in metabolite pools detected using GC/MS in H460 lung carcinoma, T47D breast cancer, and human embryonic kidney 293T cells cultured for 24 hours in the presence of [1-$^{13}$C]glutamine. From left in each set of bars: H460, T47D, 293T.

Reductive Carboxylation of αKG to Isocitrate is the Preferred Pathway of Glutamine-to-Lipid Flux Recent results from MFA conducted in lung carcinoma cells, glioblastoma cells, and quiescent fibroblasts indicate a high degree of reversibility for the IDH reaction in tumor cells (26-28). To determine whether this reaction is used for biosynthesis (i.e., supplies carbon to AcCoA and metabolites downstream of ACL) we cultured tumor cell lines of various origins with [1-$^{13}$C]glutamine (labeled on the first carbon only) and quantified the isotopic label present in metabolite pools along this pathway using gas chromatography/mass spectrometry (GC/MS). Here M0, M1, M2 mass isotopomers correspond to ion fragments containing zero, one, or two $^{13}$C atoms from the tracer, respectively. In proliferating cells, glutamine is converted to glutamate during nucleotide synthesis or by glutaminase, and the resulting glutamate is metabolized by glutamate dehydrogenase or transaminase reactions to generate αKG. Isotopic label on the first carbon of αKG is lost as $CO_2$ during oxidative metabolism to succinate but retained during reductive carboxylation. Therefore, any M1 label detected on TCA cycle metabolites derived from [1-$^{13}$C]glutamine provides a clear readout of reductive pathway activity (FIG. 1A; red carbon atoms). All cell lines tested with this tracer retained significant label from [1-$^{13}$C]glutamine in citrate as well as metabolite pools downstream of the essentially irreversible ACL reaction, indicating this reductive flux contributes to the cytosolic AcCoA pool (FIGS. 1B and 7). Additional evidence for activity along this pathway was ascertained in lung carcinoma, glioblastoma, and melanoma cell lines with uniformly $^{13}$C labeled ([U-$^{13}$C$_5$]) glutamine (FIG. 8), which provides an independent means of tracing flux through branched TCA metabolism (10). These results provide evidence that proliferating cells utilize reductive αKG metabolism for biosynthesis.

Figure 1C:
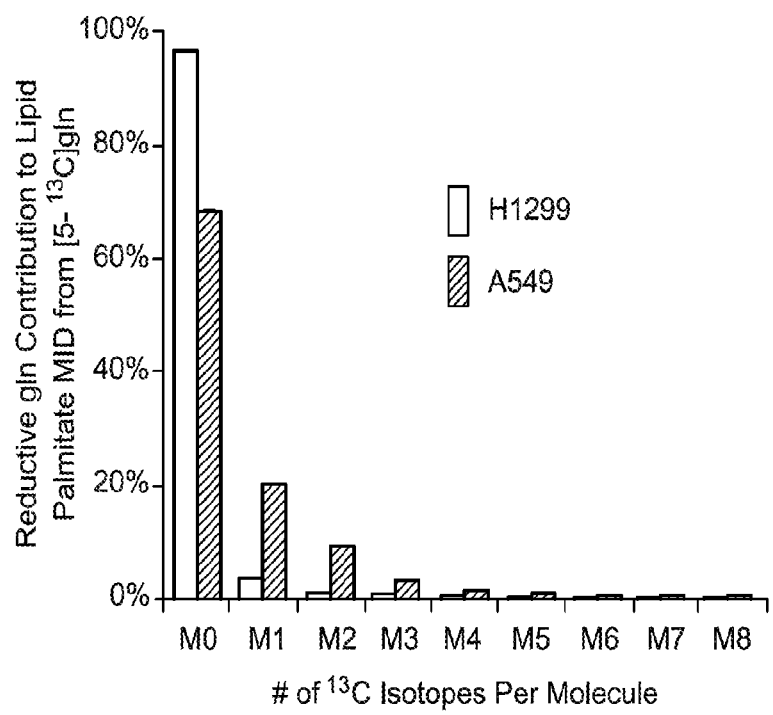
Figure 1D:
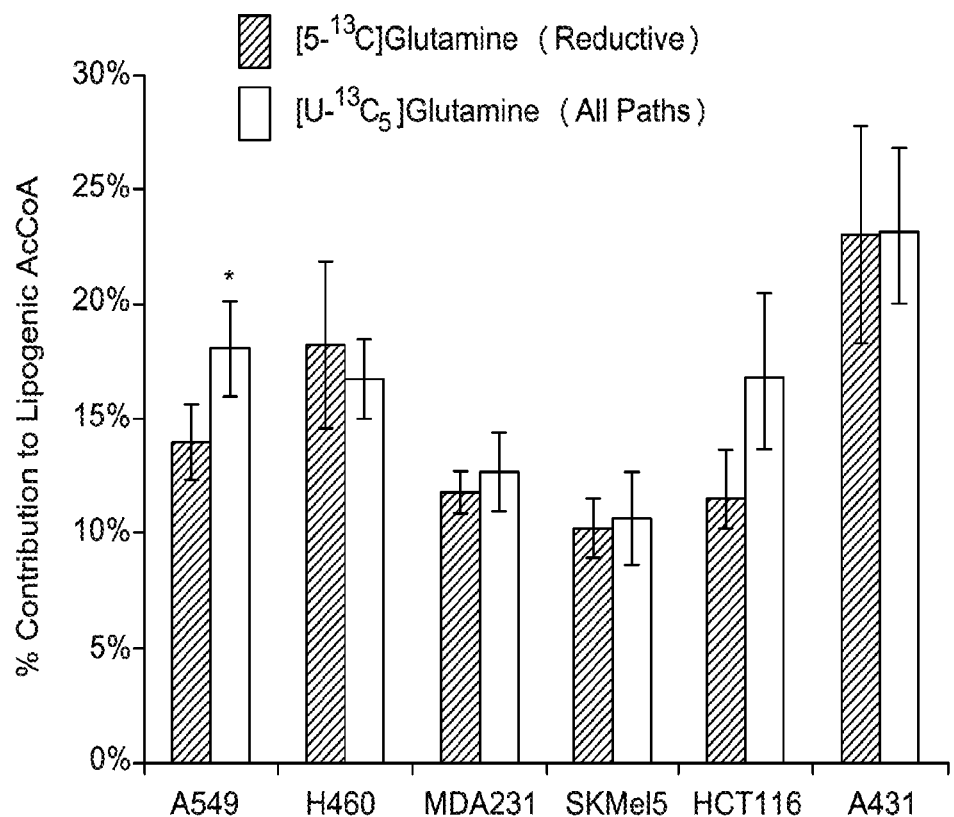
Figure 9A:
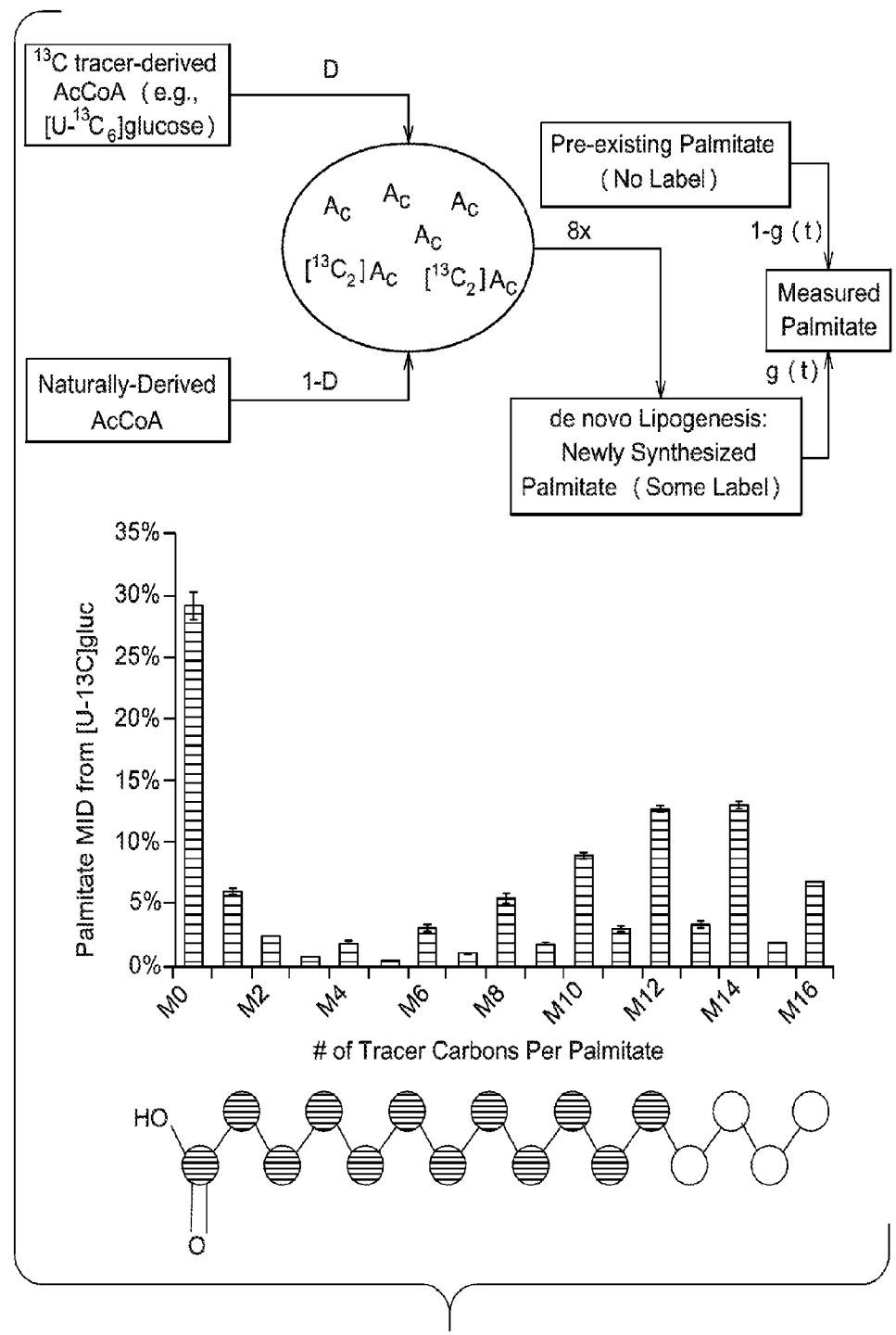
FIG. 9. Overview of Isotopomer Spectral Analysis (USA). A) ISA applied to fatty acid synthesis provides an estimate of the relative enrichment in the lipogenic AcCoA pool (red) from a given tracer (e.g. [U-$^{13}$C$_6$]glucose, [U-$^{13}$C$_5$]glutamine, or [5-$^{13}$C]glutamine). Cells are grown in the presence of tracer to generate labeled fatty acids, and the mass isotopomer distribution (MID) for palmitate is measured via GC/MS. MIDs represent the relative abundance of all mass isotopomers for a given metabolite pool and sum to 100%. The measured pool is comprised of pre-existing palmitate with no label and newly synthesized fatty acids, which may have more than one $^{13}$C label per molecule (depending on the level of enrichment in the precursor pool). The D parameter indicates the level of isotope enrichment in the AcCoA pool, and the g(t) parameter indicates the percentage of fatty acids that are newly synthesized, which depends on cell growth and time. These parameters are estimated for a given tracer and MID, and the 95% confidence interval is determined via parameter continuation/sensitivity analysis. B) Carbon atom transition map highlighting oxidative metabolism of [5-$^{13}$C]glutamine, which specifically labels fatty acids through the reductive carboxylation pathway (FIG. 1). [5-$^{13}$C]glutamine generates [1-13C] and [4-13C] succinate and fumarate through symmetry, and each labeled carbon is subsequently lost as CO2 in either glutaminolysis (malic enzyme or pyruvate dehydrogenase) or TCA cycle metabolism (IDH or oxoglutarate dehydrogenase).
Figure 9B:
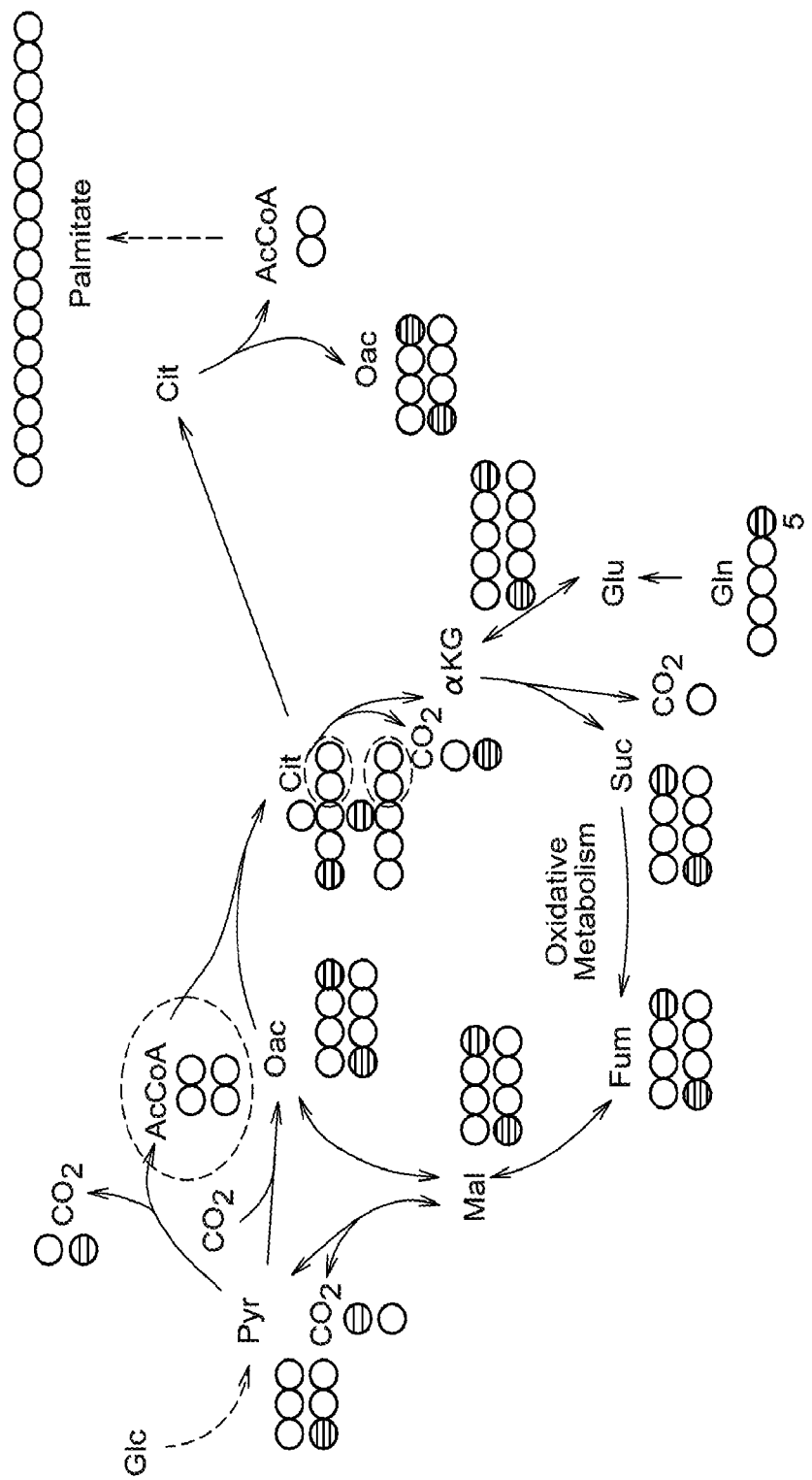
Figure 10A:
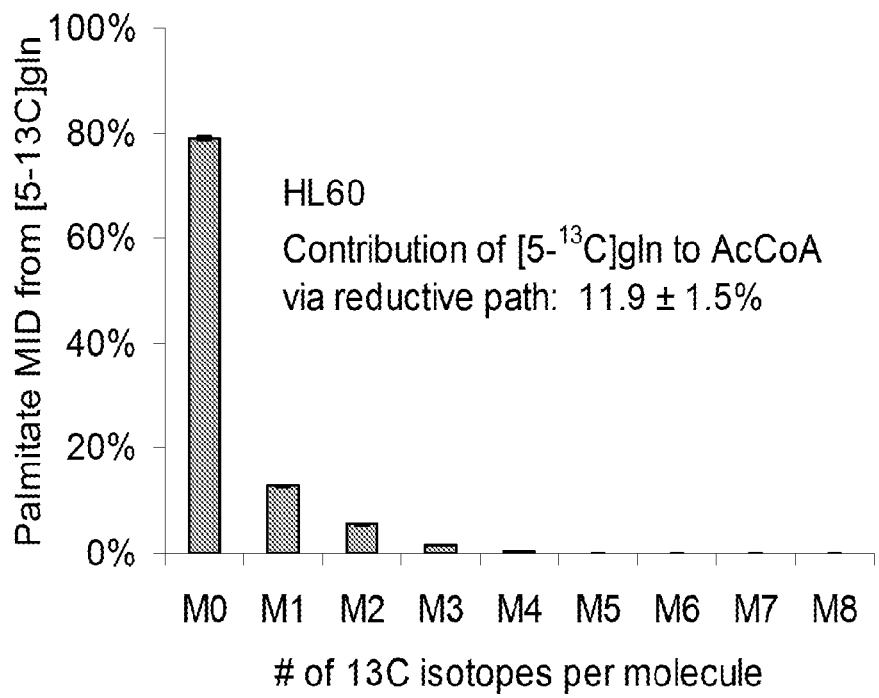
FIG. 10. Evidence for use of reductive carboxylation for lipogenesis in other cell lines and culture medium. A,B) MID data of palmitate labeling from [5-$^{13}$C]glutamine in HL60 acute myeloid leukemia cells (A) and human embryonic kidney 293T cells (B). Percent contribution of the glutamine through reductive carboxylation to lipogenic AcCoA determined by ISA (95% confidence interval from model). C) Comparison of ISA data in H460 cells cultured in DMEM or RPMI 1640 medium with [U-$^{13}$C$_5$]glutamine. Note that basal RPMI medium contains unlabeled glutamate, which causes dilution of the [U-$^{13}$C$_5$]glutamine tracer upstream of reductive carboxylation. DMEM data obtained from FIG. 1D. D) MID data of palmitate from H460 cells used for ISA modeling in (C), corrected for natural isotope abundance.
Figure 10B:
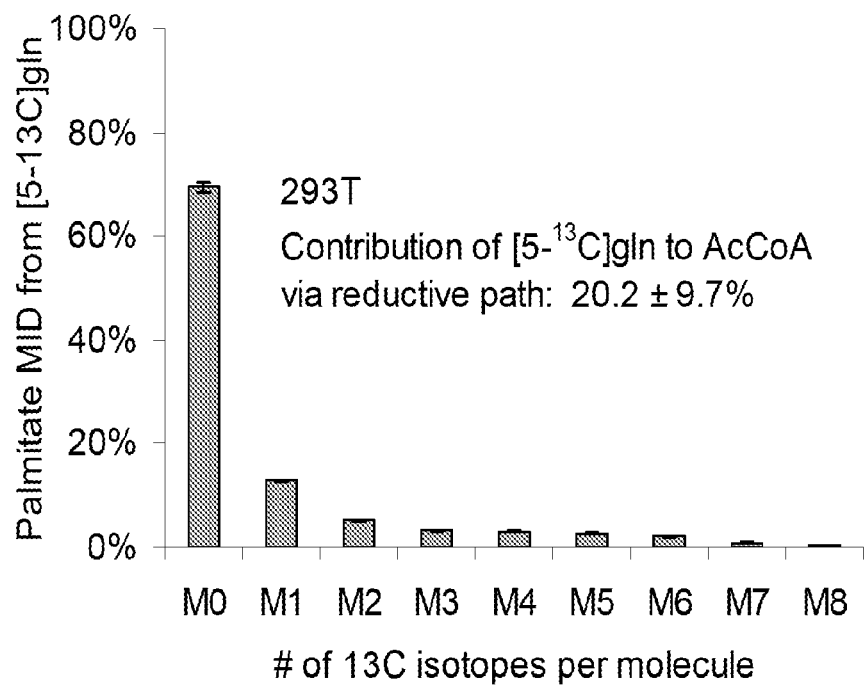
Figure 10C:
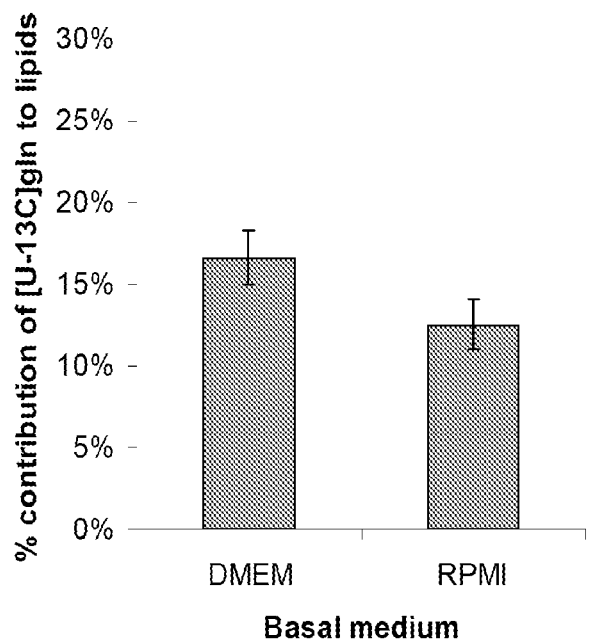
Figure 10D:
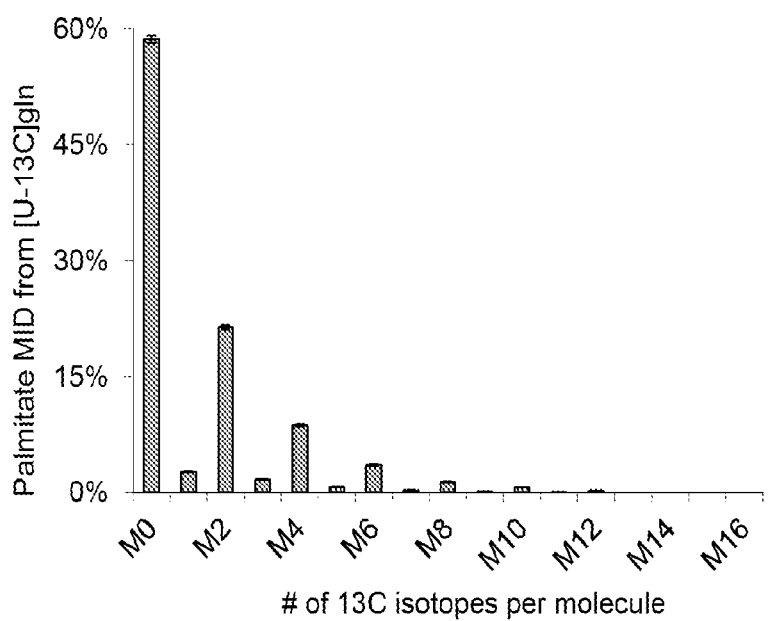

To quantify the specific contribution of reductive carboxylation to fatty acid synthesis we cultured cells in the presence of glutamine tracers for several days, long enough to ensure adequate enrichment of isotopes in lipid pools. After extraction of lipids and transesterification of fatty acids, we determined the labeling pattern of palmitate by GC/MS and employed Isotopomer Spectral Analysis (ISA) to determine the relative flux of glutamine to lipids through various pathways. In contrast to the use of radioactive tracers, ISA and related methods (29, 30) employ stable isotopes and MS to quantify de novo lipogenesis (a function of time and cell growth) and, more importantly, the enrichment of isotopes in the biosynthetic precursor pool (i.e., AcCoA; FIG. 9). Therefore, by employing specifically labeled tracers we quantified the contribution of a given pathway or flux to fatty acid synthesis. By using a [5-$^{13}$C] glutamine tracer we specifically estimated the contribution of glutamine carbon to lipogenesis that proceeds through reductive carboxylation, as isotopic label on carbon five is retained through this pathway but lost as $CO_2$ in subsequent turns of the TCA cycle (FIG. 1A, blue carbon atoms; see FIG. 9 for atom transitions during oxidative metabolism). Any label detected in fatty acid pools from the [5-$^{13}$C] glutamine tracer provides quantitative evidence of reductive pathway activity. Virtually all cell lines cultured with this tracer generated labeled fatty acids, metabolizing glutamine through reductive carboxylation to supply 10-25% of their lipogenic AcCoA (FIGS. 1C; 1D, blue bars; 10). In fact, only the H1299 lung carcinoma cell line exhibited low activity of this pathway under standard culture conditions (FIG. 1C).

Figure 8B:
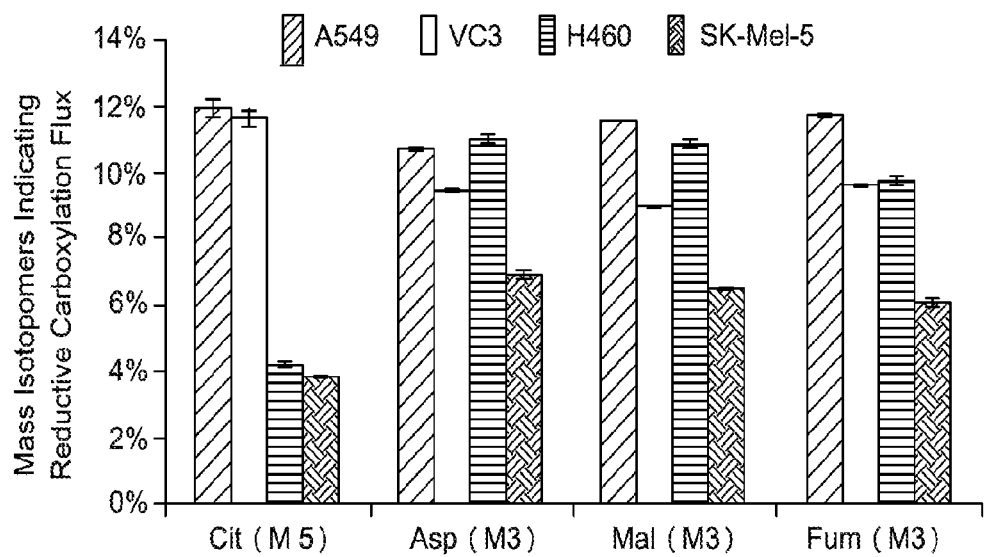
FIG. 8. Evidence for reductive carboxylation in tumor cell lines using [U-$^{13}$C$_5$]glutamine tracer. A) Carbon atom transition map depicting labeling patterns of metabolites derived from [U-$^{13}$C$_5$]glutamine during oxidative and reductive metabolism. Mass isotopomers generated by reductive carboxylation include M5 citrate, M3 aspartate, M3 malate, and M3 fumarate; any mass isotopomers labeled therein provide evidence of reductive pathway activity. Labeling patterns arising from compound symmetry and some unlabeled intermediates are omitted for simplification. When two patterns are listed for a given metabolite, the lower pattern depicts that generated in the second turn of the TCA cycle. B) Cells were cultured for 24 hours in the presence of [U-$^{13}$C$_5$] glutamine before metabolite extraction and GC/MS analysis. Relative abundance of reductive carboxylation-specific mass isotopomers are depicted as measured in (from left in each set of bars) A549 lung carcinoma, VC3 glioblastoma, H460 lung carcinoma, and SK-MeI-5 melanoma cell lines. Error bars indicate s.e.m. (n=3).
Figure 8A:
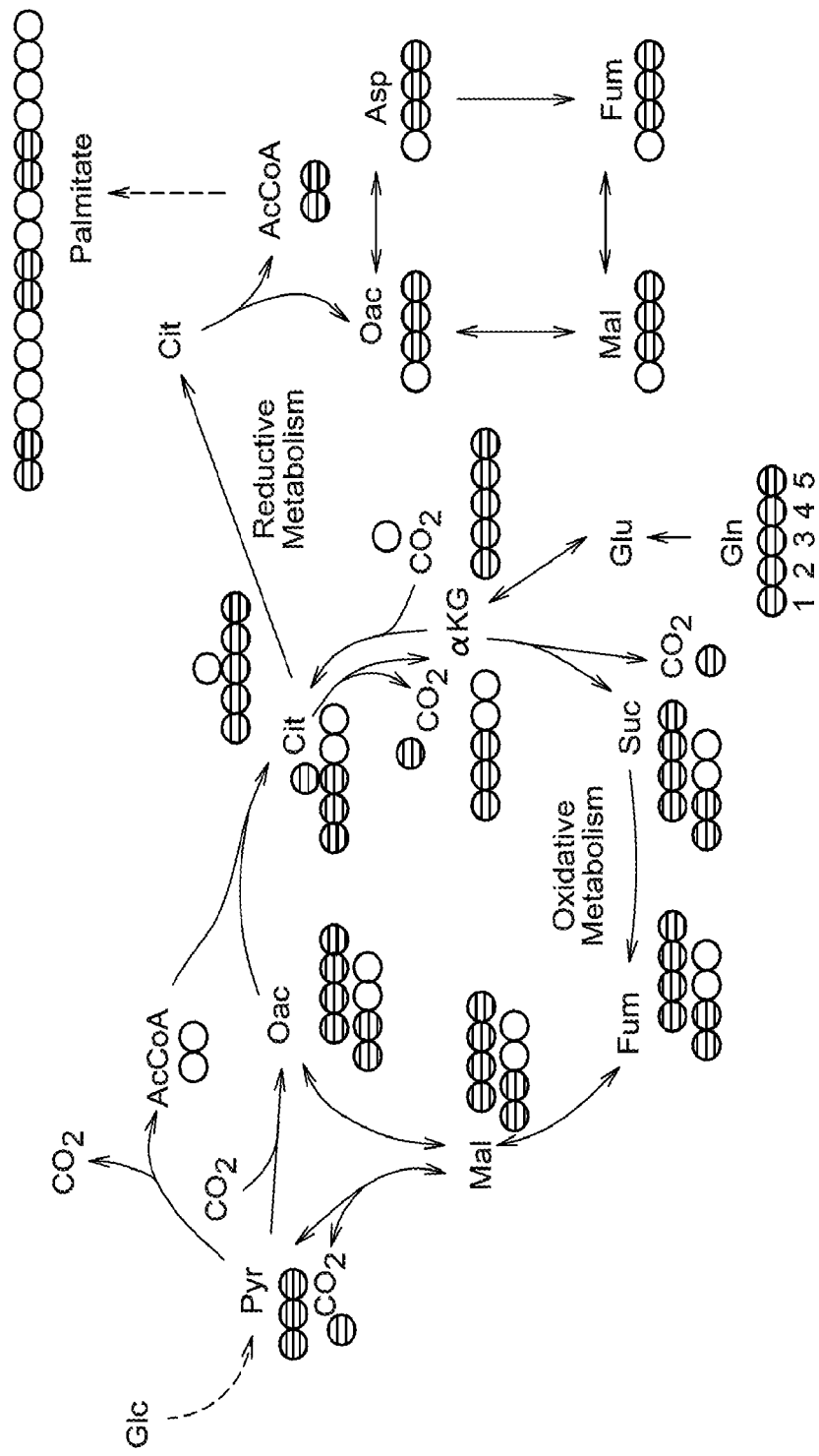
Figure 11:
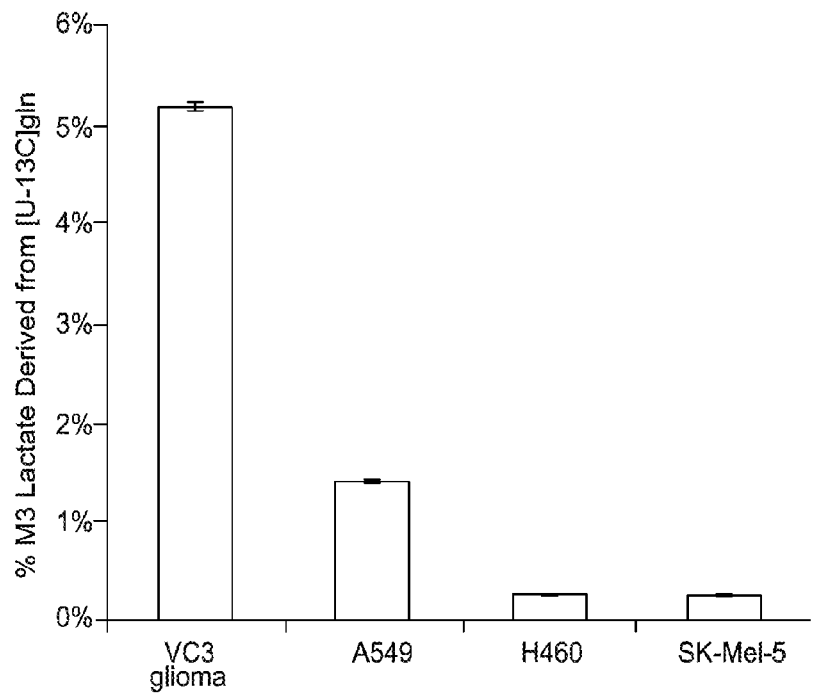
FIG. 11. Cells derived from glioblastoma tumors exhibit elevated glutaminolysis compared to other cell types. Comparison of the relative abundance of M3 lactate mass isotopomers derived from [U-$^{13}$C$_5$]glutamine in glioblastoma (VC3), lung carcinoma (A549 and H460), and melanoma (SK-Mel-5) cell lines. Error bars indicate s.e.m. (n=3).

Next we directly compared the contribution of glutamine to fatty acids via the reductive flux as a fraction of the total, the latter determined by using [U-$^{13}$C$_5$]glutamine, which can transfer isotopic label to AcCoA through glutaminolysis in addition to reductive carboxylation (FIG. 8). Any increase detected when using [U-$^{13}$C$_5$]glutamine compared to [5-$^{13}$C]glutamine indicates flux through the glutaminolytic pathway. In all cell lines except A549, there was no significant difference in AcCoA enrichment between the two tracers (FIG. 1D; 95% confidence intervals from ISA fit shown). These results demonstrate that reductive carboxylation is the primary route through which glutamine, glutamate, and αKG carbon are converted to lipids in cultured cells. Similar results obtained using the above glutamine tracers in a range of cell lines with different culture media, including H460, MDA-MB-231, T47D, SK-Mel-5, HCT116, A431, HL60, 293T, and VC3 cells, highlight the general use of this pathway (FIGS. 1D, 7, 8, 10). The glutaminolysis pathway can also be characterized by quantifying the contribution of glutamine carbon to lactate. Consistent with previous reports (4, 5), glutamine-derived $^{13}$C label was also detected in lactate, and the amount of $^{13}$C-labeled lactate produced was highest in glioblastoma-derived cells compared to other cell lines cultured with [U-$^{13}$C$_5$]glutamine (FIG. 11).

Example 2

Cytosolic IDH1 is the Primary Mediator of Reductive Carboxylation Flux

Figure 2A:
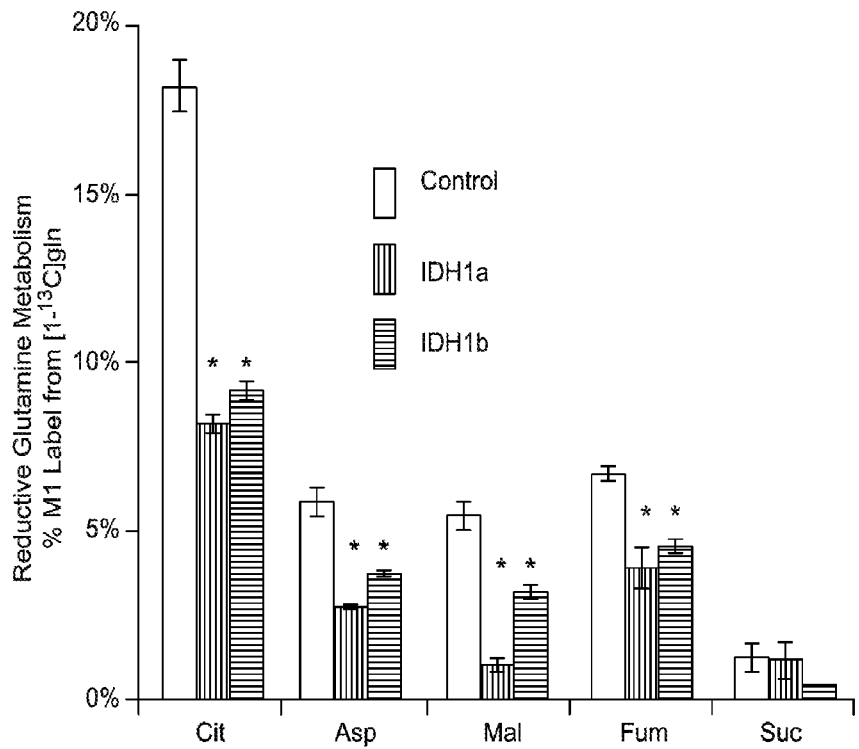
FIG. 2. IDH1 is the primary mediator of reductive carboxylation. A) Reductive glutamine metabolism in A549 cells expressing IDH1-specific shRNAs (IDH1a and IDH1b). B) IDH1 protein levels and citrate MIDs in IDH1 knockdown cells cultured with [U-$^{13}$C$_5$]glutamine (atom transitions are described in FIG. 8). C) IDH flux estimates from $^{13}$C MFA model (error bars indicate 95% CI). D) NADPH consumption by recombinant IDH1 at 0%, 5%, and 10% CO$_2$. E) Cell growth of A549 cells expressing IDH1-shRNAs. F) Relative growth rates of cell lines stably expressing control or IDH1-targeting shRNAs. G,H) Luciferase activity of A549-IDH1-shRNA cells transiently expressing ODD-Luc (G) or HRE-Luc (H) vectors and cultured under normoxia, hypoxia (1% O$_2$), or with 1 mM DMOG for 18 hours. White bars and black line indicate control, red/dark grey bars/line indicate IDH1a, and blue/light grey bars/line indicate IDH1b shRNAs. Error bars indicate s.e.m. (n=3) for all panels but (C). * denotes p<0.05 relative to control.
Figure 2B:
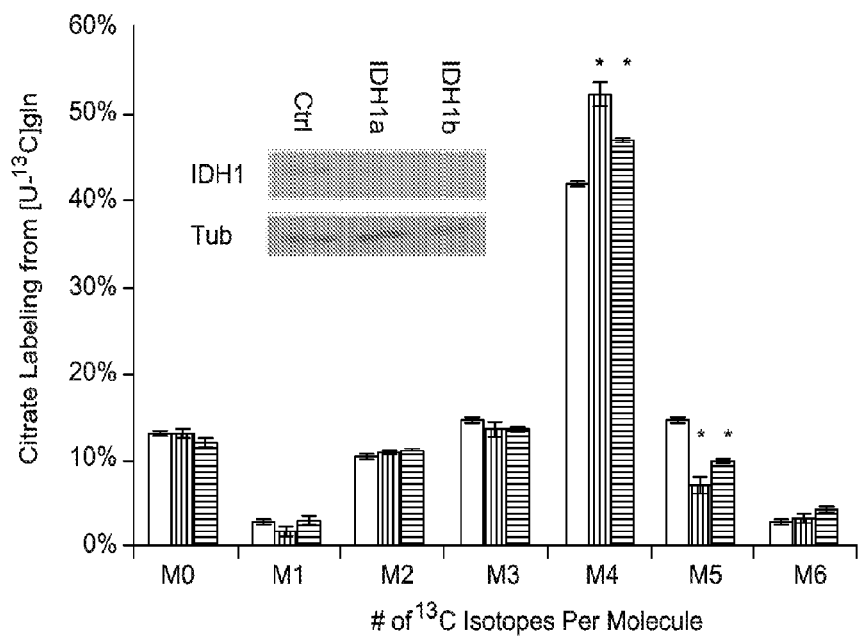
Figure 2C:
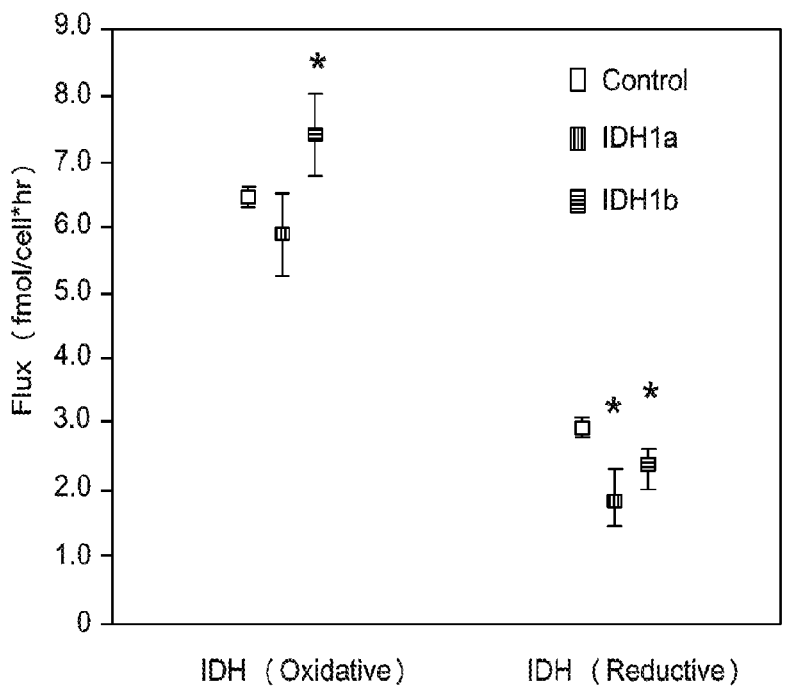
Figure 12:
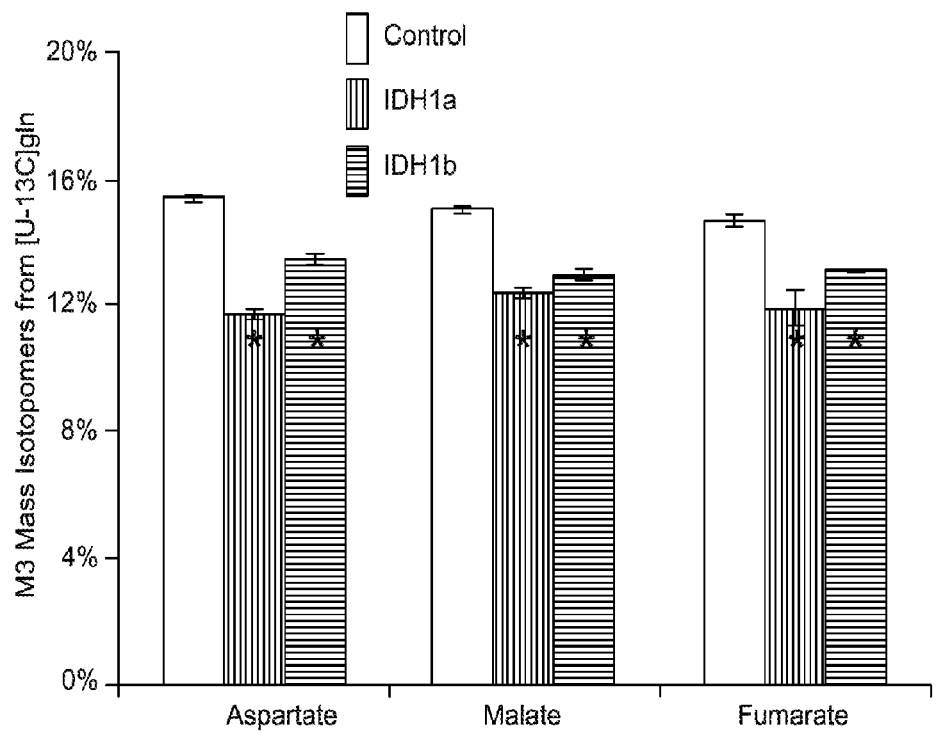
FIG. 12. M3 mass isotopomers derived from [U-$^{13}$C$_5$] glutamine in A549 cells expressing control or IDH1-targeting shRNAs indicate a decrease in reductive carboxylation upon knockdown of IDH1 mRNA. From left in each set of bars: control, IDH1a shRNA, IDH1b shRNA. Error bars indicate s.e.m. (n=3). Trends were observed in at least 3 independent knockdown experiments.

Mammalian cells express three IDH enzymes encoded by separate genes: IDH1 (cytosolic, NADP$^+$-dependent), IDH2 (mitochondrial, NADP$^+$-dependent), and IDH3 (mitochondrial, NADP$^+$-dependent). Only the NADP$^+$-dependent isozymes are known to catalyze the reductive reaction and consume αKG; however, the specific enzyme responsible for this flux is not definitively known (8, 9). As compartmentalized measurements of metabolite pools and labeling therein cannot yet be reliably obtained, we employed RNA interference to selectively knock down expression of IDH1 and IDH2 in A549 cells. Using the labeling patterns resulting from [1-$^{13}$C]glutamine as a readout, we measured a significant and robust decrease in reductive carboxylation when IDH1 mRNA was targeted using shRNA (FIG. 2A). These changes in M1 label were consistent across the expected metabolite pools and reproduced with two separate shRNA hairpins. Additional confirmation was obtained using [U-$^{13}$C$_5$]glutamine, as we detected a decrease in M5 mass isotopomers of citrate when IDH1 levels were knocked down (FIG. 2B). Importantly, we observed a concomitant increase in M4 mass isotopomers, indicating that cells expressing shRNAs targeting IDH1 exhibit elevated oxidation of glutamine-derived αKG (i.e., "forward" flux through the TCA cycle; FIG. 2B). Similar trends were obtained for the M3 mass isotopomers of aspartate, malate, and fumarate in the same extracts (FIG. 12). Finally, we employed $^{13}$C MFA to quantify intracellular fluxes using [U-$^{13}$C$_5$]glutamine as a tracer. Results suggested that reductive IDH flux significantly decreased when targeting IDH1 mRNA, and this change was the primary alteration observed in the network (FIG. 2C; see Tables 1-5 for complete results and description of MFA model and assumptions).

Figure 2D:
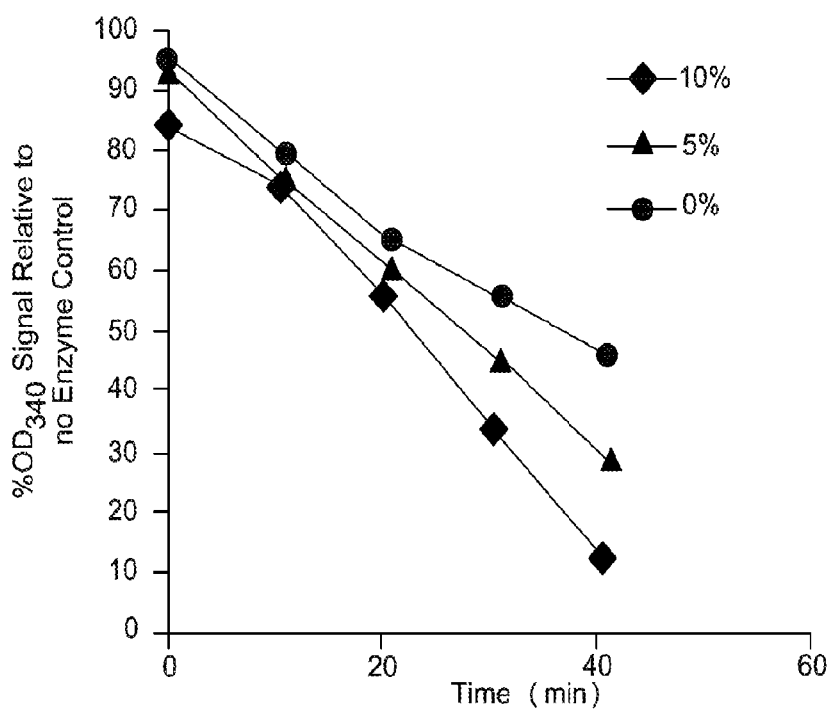
Figure 2E:
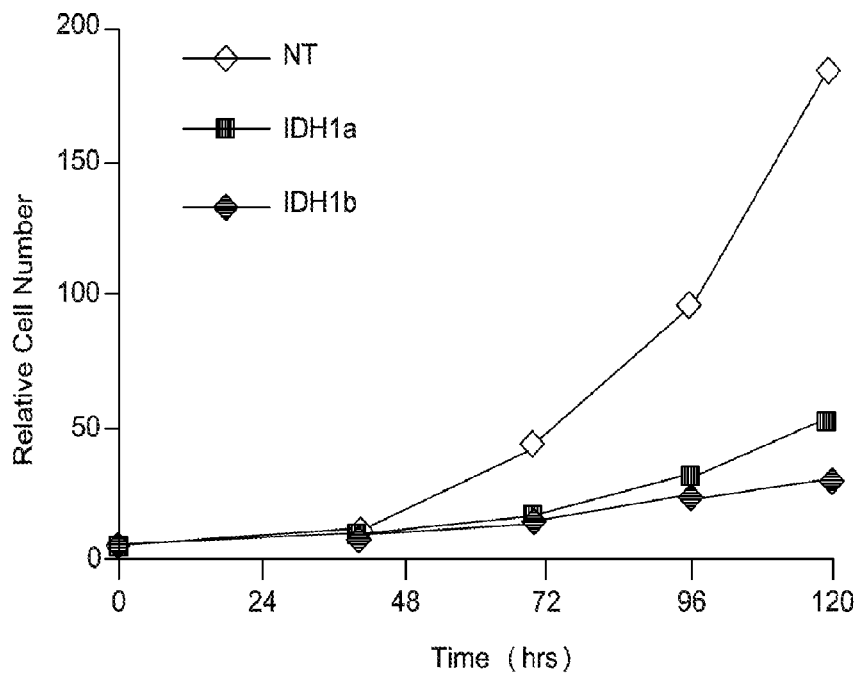
Figure 2F:
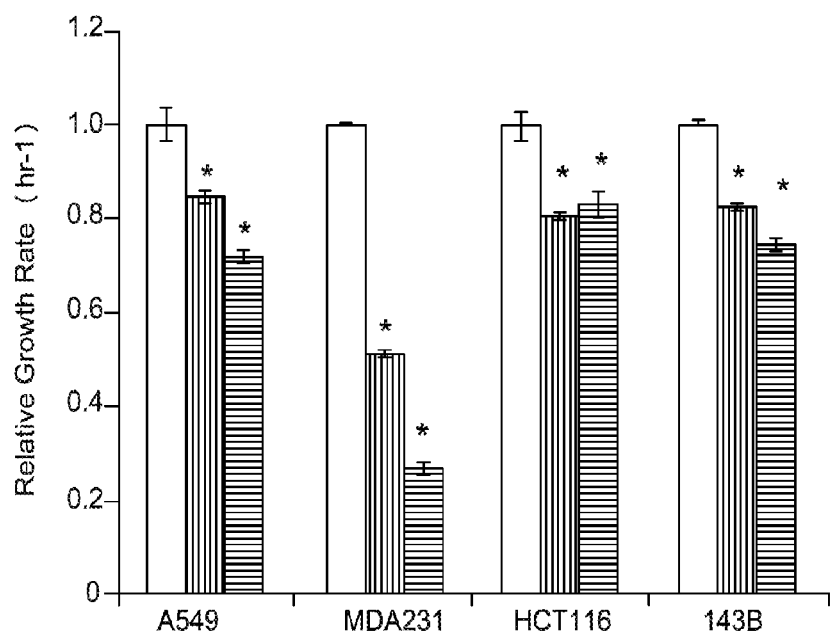
Figure 13A:
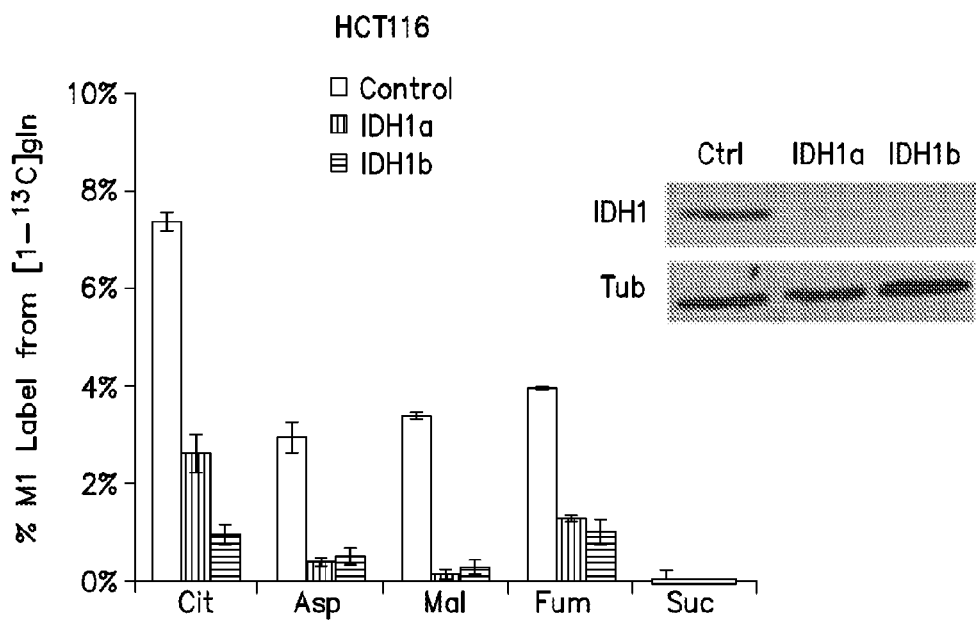
FIG. 13. Targeting of IDH1 mRNA with shRNA's reduces reductive carboxylation flux in HCT116 colon carcinoma (A), MDA-MB-231 breast carcinoma (B), and 143B osteosarcoma (C) cell lines. A,B) Decreased M1 label was observed in citrate, asparatate, malate, and fumarate from the [1-$^{13}$C]glutamine tracer. From left in each set of bars: control, IDH1a shRNA, IDH1b shRNA. Error bars indicate s.e.m. (n=3). Western blots indicate decreased protein levels of IDH1 upon shRNA expression. Knockdown of protein was not complete, as indicated by detection of IDH1 in blots at long exposures (not shown for B).
Figure 13B:
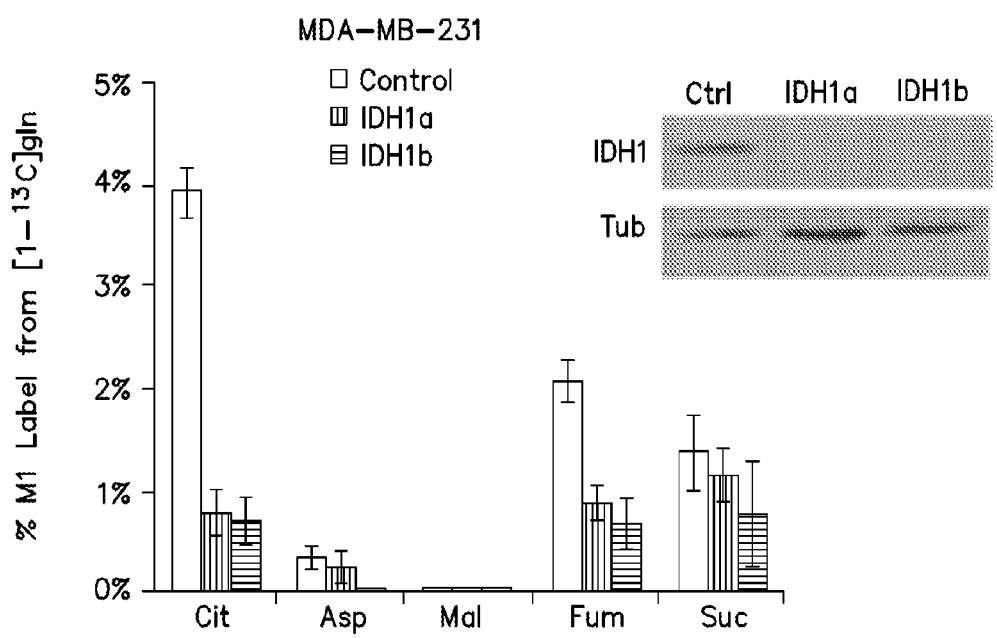
Figure 13C:
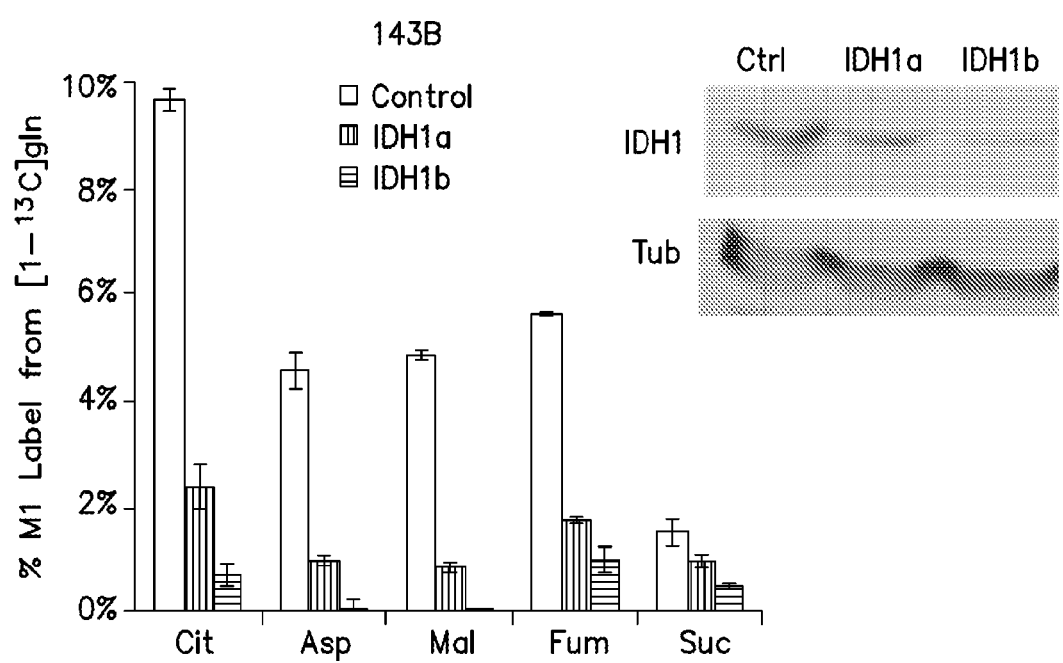
Figure 14:
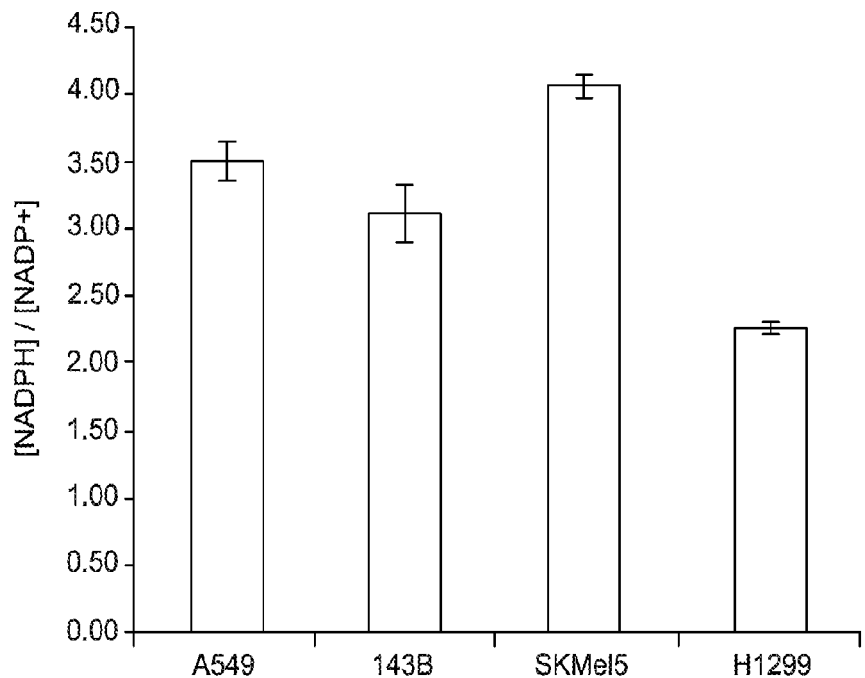
FIG. 14. Ratio of NADPH to NADP+ in total cell lysates from various cell lines indicates that NADPH levels are adequate for driving the reductive flux. Sufficient NADPH is presumably generated through the oxidative pentose phosphate pathway or other reactions to maintain activity of reductive carboxylation.
Figure 15A:
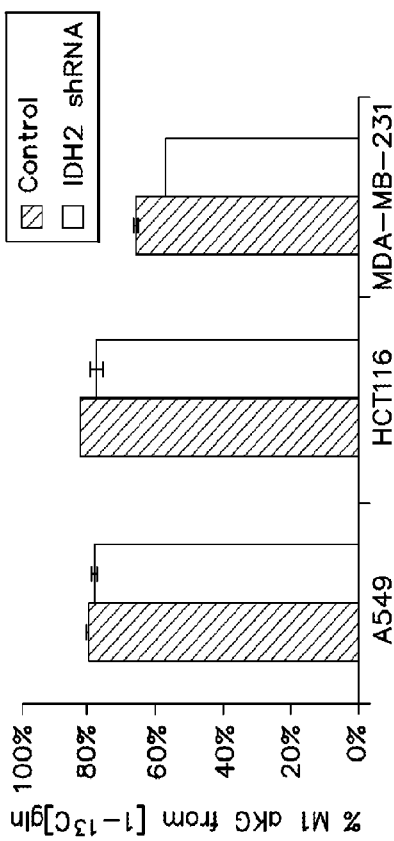
FIG. 15. Knockdown of IDH2 protein with shRNA does not affect reductive carboxylation flux. A) Stable A549, HCT116, and MDA-MB-231 cell lines expressing decreased levels of IDH2 generated similar citrate labeling patterns from [1-$^{13}$C]glutamine to control cells expressing scrambled shRNAs. B) The slight decrease in M1 citrate levels in MDA-MB-231 cells arises from decreases in M1 label in the αKG pool. Error bars indicate s.e.m. (n=3). C) Validation of knockdown in each cell line by Western blotting. From left in each set of bars: control, IDH2 shRNA.
Figure 15B:
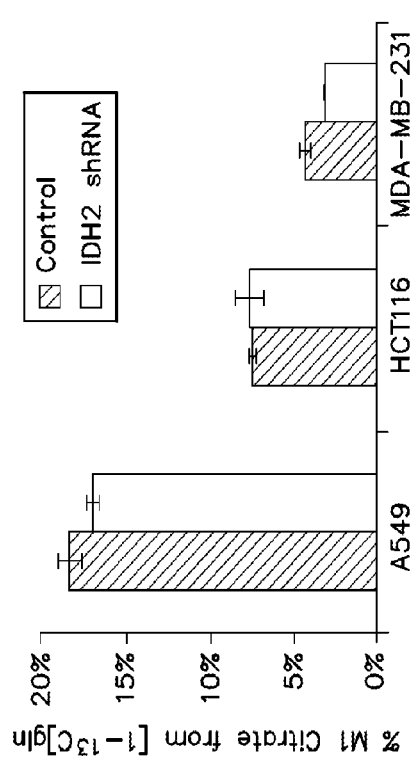
Figure 15C:
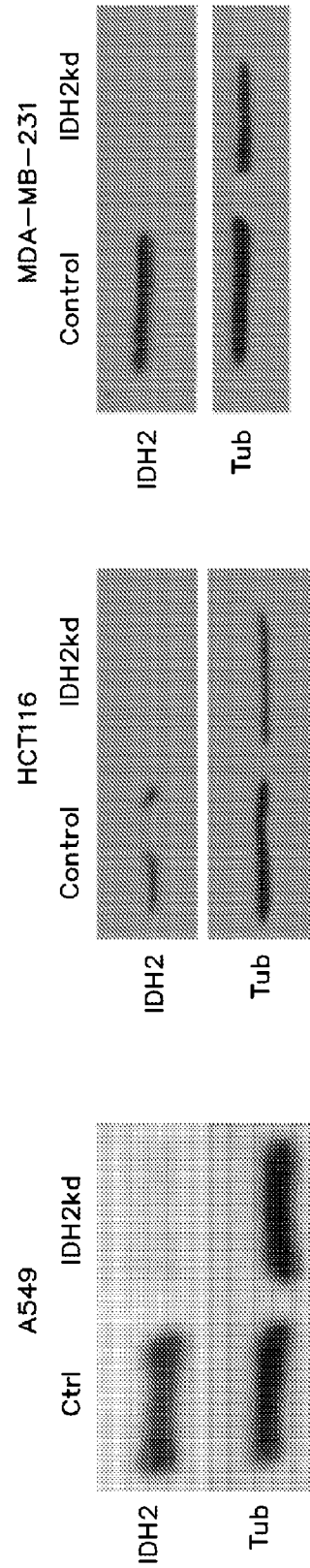
Figure 18A:
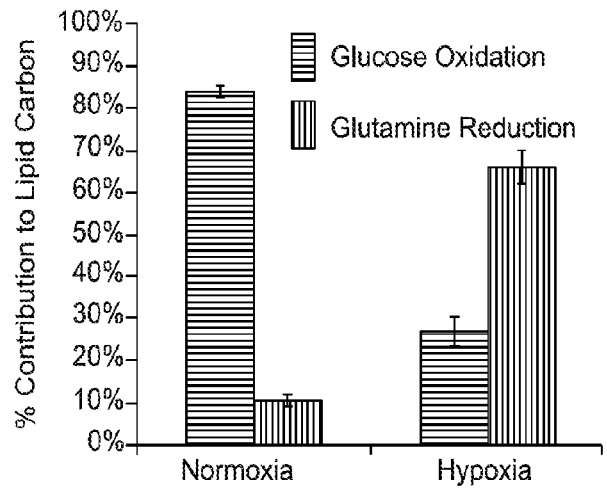
FIG. 18. Tumor cells change their carbon source for lipid synthesis under hypoxia. A-E) ISA analysis to determine the contribution of glucose and glutamine (reductive pathway only) to AcCoA in 143B (A), HCT116 (B), H1299 (C), MDA-MB-231 (D), and MCF10A (E) cells. Cells were grown for 3 days under 21% or 1-2% $O_2$ in the presence of [U-$^{13}$C$_6$]glucose or [5-$^{13}$C]glutamine tracers before extraction. Spent medium was analyzed at the conclusion of culture to ensure that tracer substrates did not expire. Note that MCF10A cells were cultured in DMEM/F12 basal medium with 5% horse serum that was not dialyzed. Therefore unlabeled glutamine, glutamate, and proline were present an potentially dilute the contribution of [5-$^{13}$C]glutamine to lipids. From left in each set of bars: glucose oxidation (blue/dark grey bars), glutamine reduction (red/light grey bars). Error bars indicate 95% confidence intervals from ISA model.
Figure 18B:
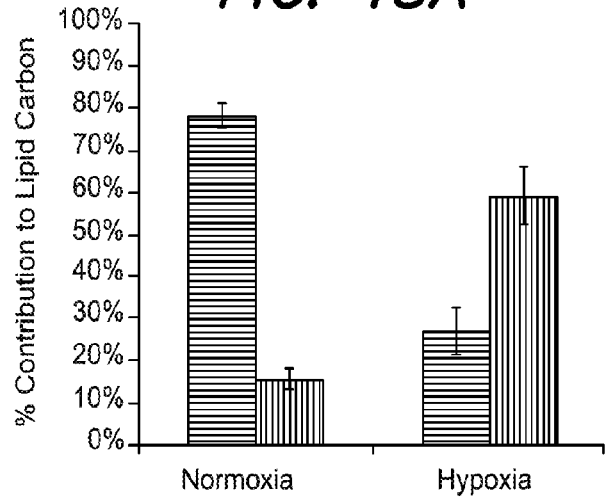
Figure 18C:
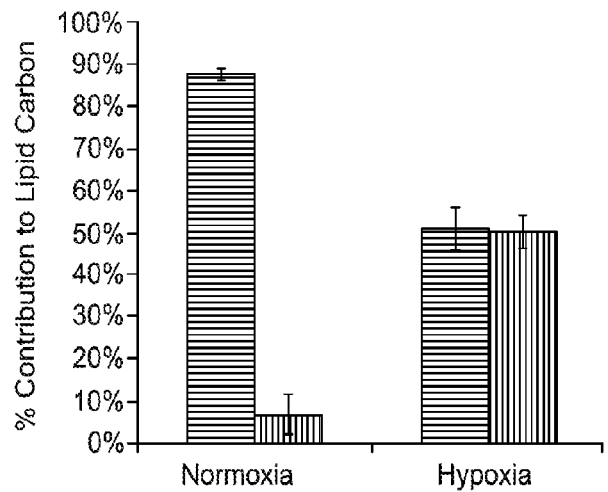
Figure 18D:
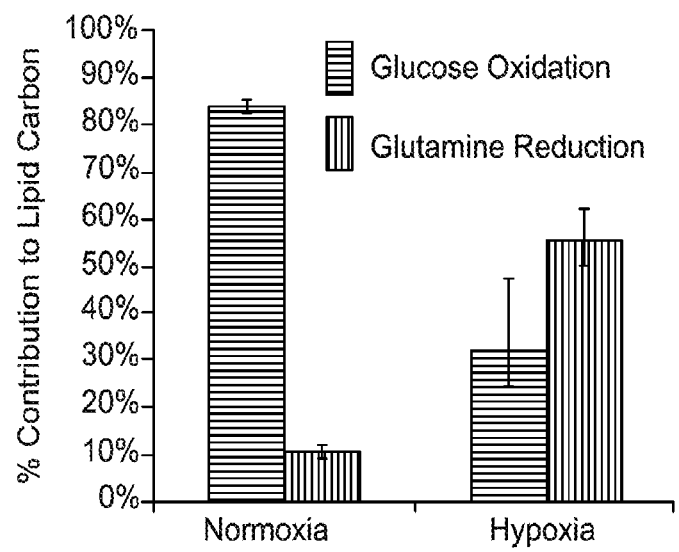
Figure 18E:
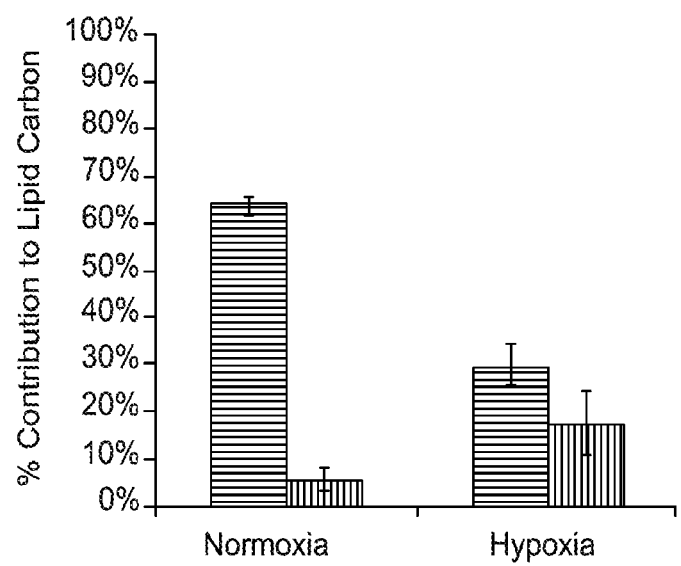

Similar findings were obtained by performing shRNA-mediated IDH1 knockdown in three additional cell lines of various tissue origins: HCT116 (colon), MDA-MB-231 (breast), and 143B (osteosarcoma) cells (FIG. 13), demonstrating that IDH1-mediated reductive carboxylation is common to several cell types with different genetic backgrounds. These data suggest that IDH1 consumes αKG and NADPH in the cytosol, ultimately producing isocitrate, which, in turn, is converted to lipogenic citrate by aconitase (ACO1). Despite this increased requirement for NADPH, we measured NADPH and NADP levels in total cell lysates and confirmed that the pool was predominantly in the reduced form (FIG. 14). Furthermore, enzymatic analysis using recombinant IDH1 indicated that this protein is indeed capable of consuming NADPH and is responsive to physiological levels of $CO_2$ (FIG. 2D). Importantly, the growth rate of all cell lines with IDH1 knockdown was impaired (FIG. 2E, 2F), indicating that reductive metabolism of αKG in the cytosol may be necessary for robust growth of some human cells. In contrast to our results with IDH1 knockdown, we detected no significant change in reductive flux when targeting IDH2 mRNA, as measured by M1 citrate labeling in cells cultured with [1-$^{13}$C]glutamine (FIG. 15). Although IDH2 may participate in the reductive pathway in some cell types, results in the cells we tested are consistent with the interpretation of IDH2 as an oxidative TCA cycle enzyme (31).

Figure 2G:
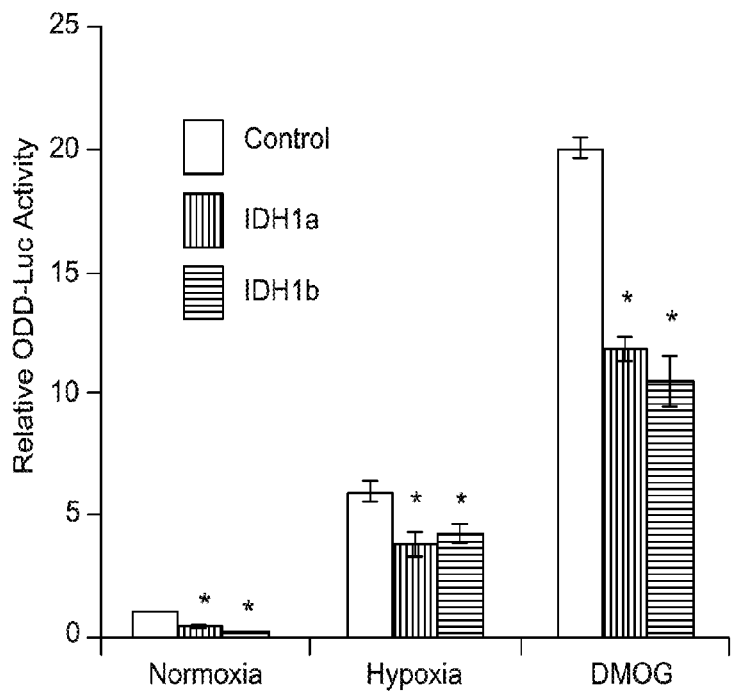
Figure 2H:
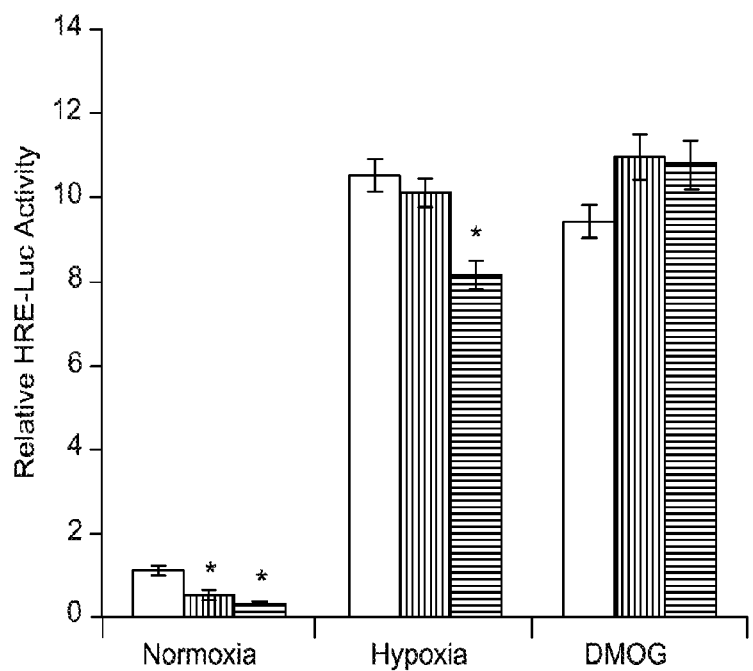
Figure 3A:
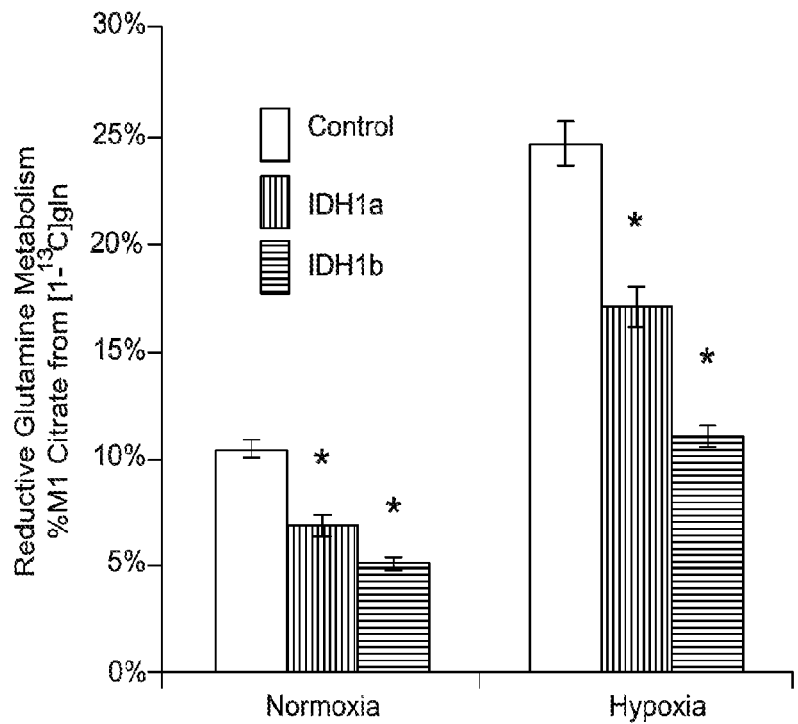
FIG. 3. Hypoxia reprograms cells to rely on reductive carboxylation for lipid synthesis. A) Reductive glutamine metabolism increases in A549 cells expressing IDH1-shRNAs cultured under hypoxia. White bars indicate control, red/dark grey bars indicate IDH1a, and blue/light grey bars indicate IDH1b shRNAs. B) Cell-specific uptake of glucose and glutamine and secretion of lactate and glutamate in A549 cells cultured under normoxia or hypoxia. Blue/light grey bars indicate normoxia and red/dark grey bars indicate hypoxia. C,D) MIDs of palmitate extracts from A549 cells cultured under normoxia or hypoxia with either [5-$^{13}$C] glutamine (C) or [U-$^{13}$C$_6$]glucose (D). Similar results were observed in the labeling of oleate and stearate (not shown). Error bars indicate s.e.m. (n=3). Blue/light grey bars indicate normoxia and red/dark grey bars indicate hypoxia. E,F) Percent contribution of glucose oxidation (using [U-$^{13}$C$_6$] glucose) or glutamine reduction (using [5-$^{13}$C]glutamine) to lipogenic AcCoA in A549 (D) or MRC5 (E) cells cultured for 3 days under normoxia or hypoxia (results from ISA; error bars indicate 95% CI). Grey bars indicate glucose oxidation and white bars indicate glutamine reduction. * denotes p<0.05.
Figure 16:
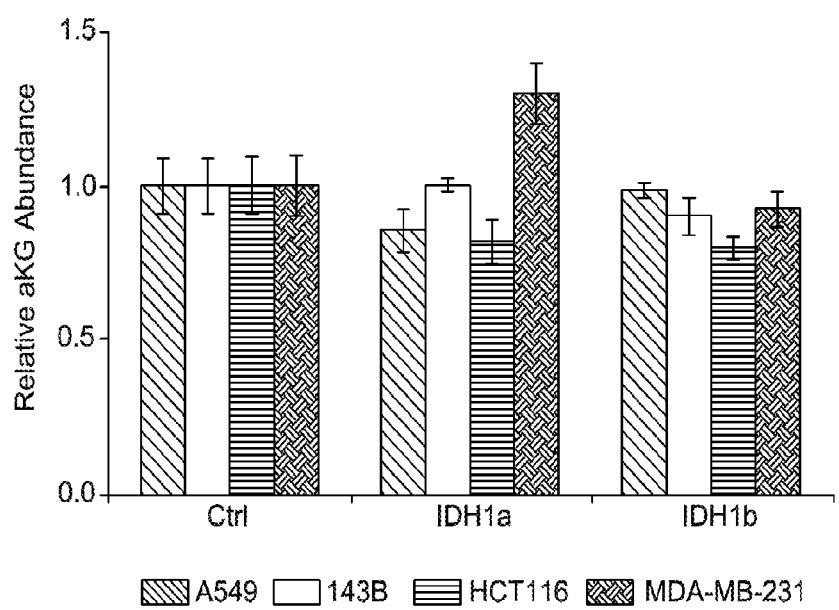
FIG. 16. No change in relative αKG levels was detected in cells expressing IDH1-targeting shRNAs. All potentially labeled ions for the αKG 346 m/z fragment were integrated, and overall abundance was normalized to the internal control, norvaline, and control cells expressing non-targeting shRNA. From left in each set of bars: A549, 143B, HCT116, MDA-MB-231. Error bars indicate s.e.m. (n=3).

Recently it has been proposed that IDH1 exhibits tumor suppressor activity through the production of αKG (32), which is a necessary substrate in the prolyl hydroxylase (PHD)-mediated degradation of HIFα subunits (14, 15). Mutations in this enzyme, which have been observed in both glioma and leukemia, are proposed to dominantly inhibit the assumed oxidative activity of IDH1 and thereby induce the HIF pathway, contributing to tumorigenesis (32). Since our results suggest that IDH1 reductively consumes αKG in the cytosol, we examined the activity of PHDs upon IDH1 knockdown to observe any potential changes. Notably, we did not observe a significant change in αKG levels in any cell line expressing IDH1-targeting shRNAs (FIG. 16). After transiently expressing luciferase reporters modified to include the oxygen-degradation domain of HIF-1α (ODD-Luc) we observed a significant decrease in luciferase activity in A549-IDH1 shRNA cells cultured under normoxia, hypoxia, or in the presence of the αKG analog dimethyloxalylglycine (DMOG) (FIG. 2G). These data are consistent with our flux analysis results, as a decrease in reductive carboxylation would increase αKG flux through PHDs by virtue of enhancing αKG availability. We also observed a slight, though less robust decrease in HIF-mediated transcription and HIF-1α stabilization (FIGS. 2H, 17). Intriguingly, we detected a significant increase in reductive carboxylation activity when culturing cells under hypoxia (FIGS. 3A, 17). As such, IDH1 may not play a dominant role in regulating HIF signaling; rather, the cellular response to hypoxia acts to drive reductive flux through IDH1.

Example 3

Figure 3B:
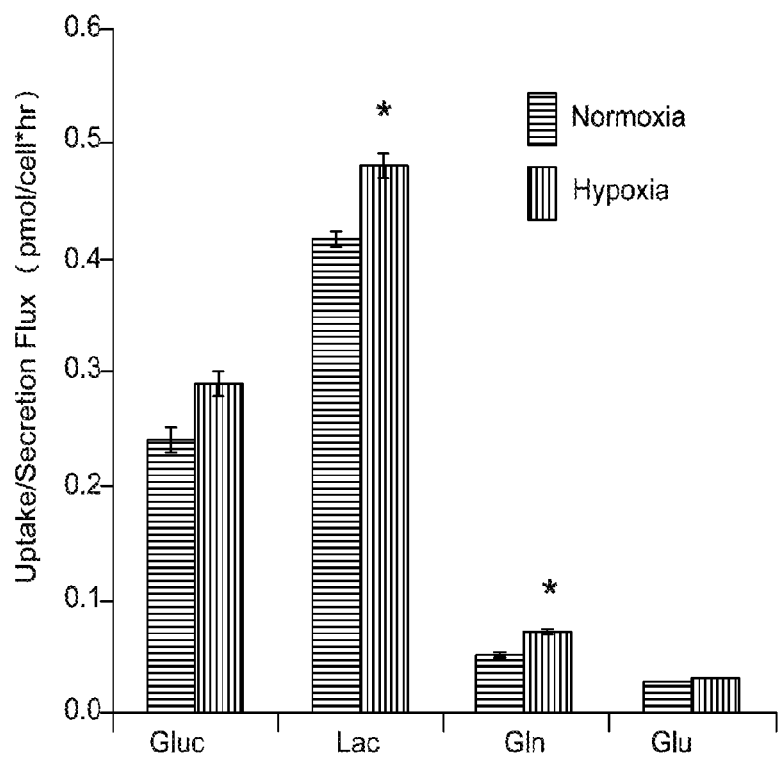

Hypoxia Reprograms Metabolism to Use Reductive Carboxylation as the Primary Source of Lipogenic AcCoA In general, hypoxia shifts cells toward a glycolytic or "Warburg-like" phenotype while shunting carbon away from oxidative metabolism (11). However, a functional electron transport chain and glutamine-derived carbon, in particular, are required for proliferation of transformed cells under hypoxia (33). Consistent with these changes, we measured increases in glucose and glutamine consumption as well as lactate secretion in A549 cells cultured under hypoxia (FIG. 3B). Notably, there was no increase in glutamate secretion, indicating that glutamine carbon is used at elevated rates under low $O_2$ conditions.

Figure 3C:
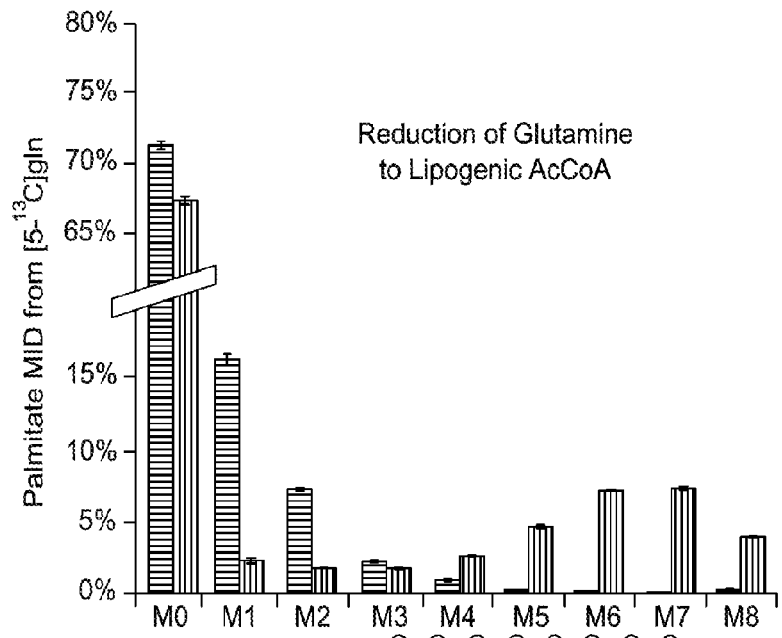
Figure 3D:
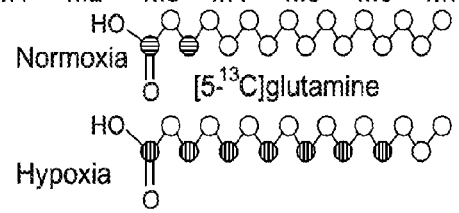
Figure 3D:
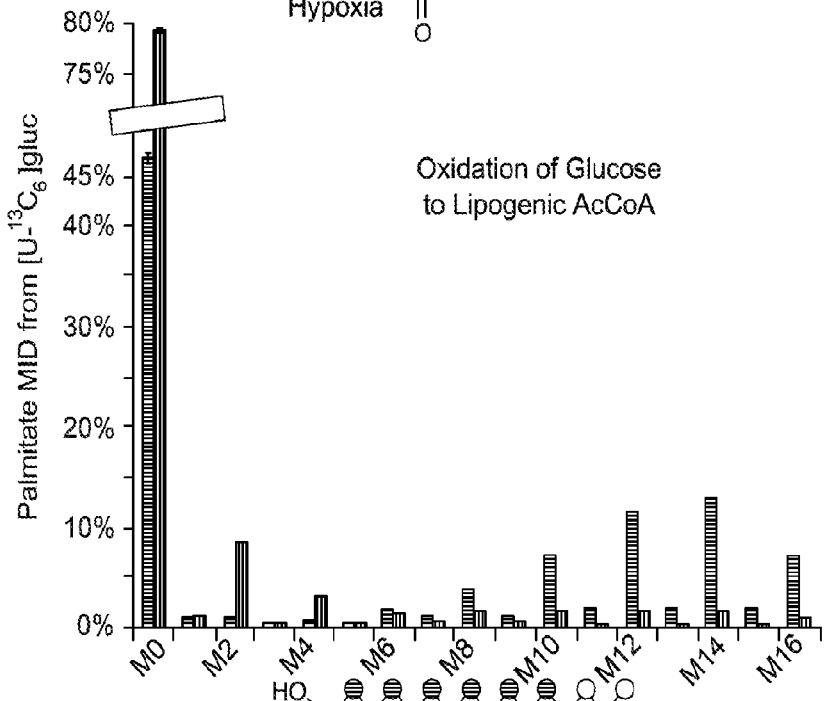
Figure 3E:
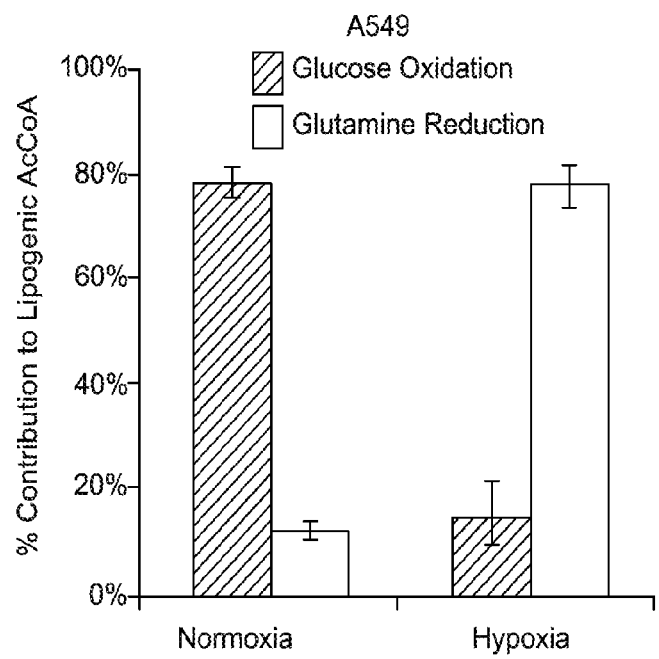
Figure 3F:
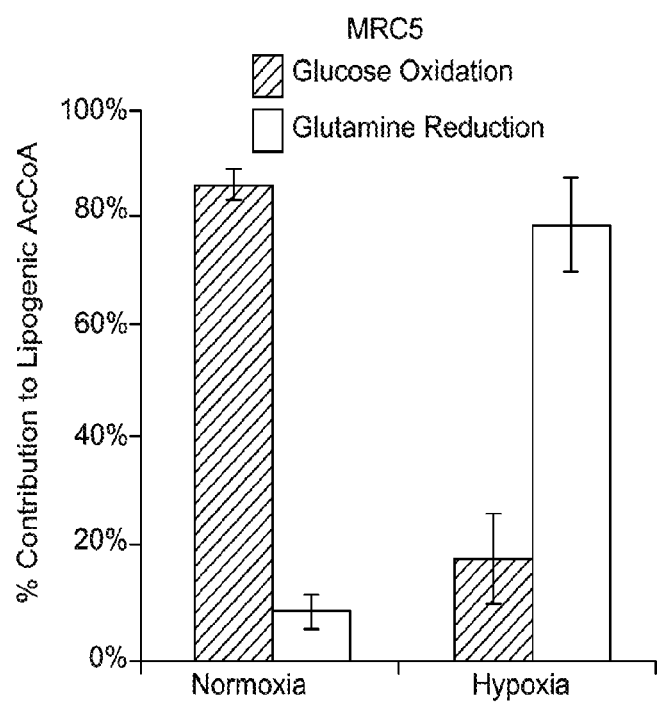
Figure 19A:
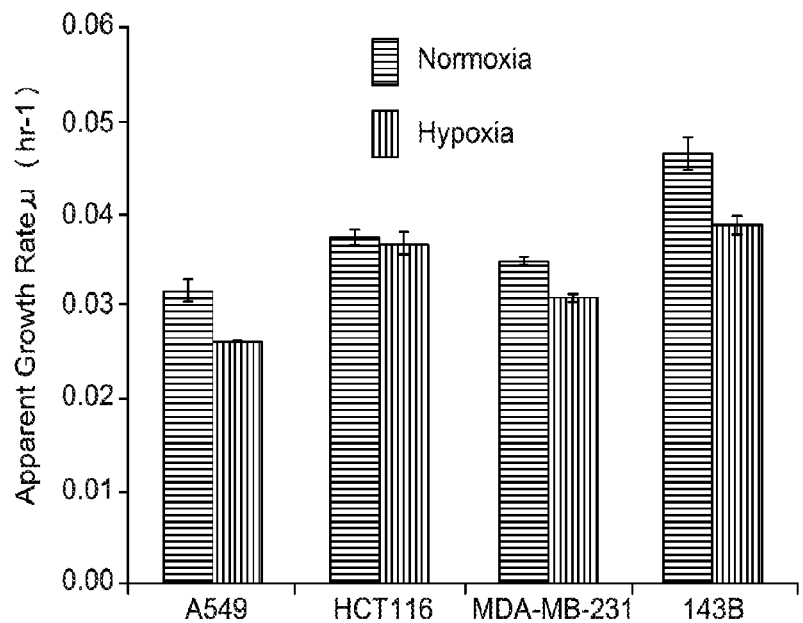
FIG. 19. Rates of proliferation and de novo lipogenesis in cells cultured under hypoxia. A) Apparent cell growth rates were calculated assuming exponential growth from cells grown for 3 days under normoxia or hypoxia. Error bars for proliferation rates indicate s.e.m. (n=3). B) Relative rates of de novo lipogenesis were determined via ISA modeling as described in FIG. 9. g(t) values were normalized to that of normoxic culture and further scaled by palmitate abundances (measured by GC/MS) in order to account for differences in cell growth/number. From left in each set of bars: normoxia (blue/dark grey bars), hypoxia (red/light grey bars). Error bars for de novo lipogenesis estimates are 95% confidence intervals.
Figure 19B:
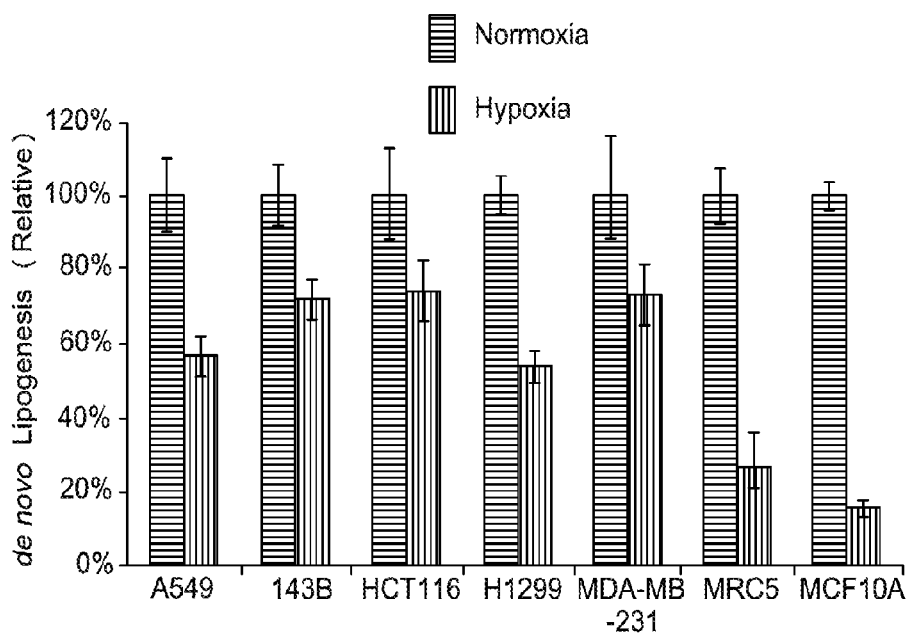

We then compared the contributions of reductive glutamine metabolism and glucose oxidation to fatty acid synthesis in cells cultured at normoxia and hypoxia by performing ISA using either [5-$^{13}$C]glutamine or uniformly labeled [U-$^{13}C_6$]glucose, respectively. Strikingly, we observed significant changes in fatty acid labeling from both tracers when culturing cells under hypoxia (FIG. 3C, 3D). Cells preferentially utilized glucose carbon for palmitate synthesis under normoxic conditions, consistent with previous reports (1, 3). However, fatty acids produced under hypoxia were primarily synthesized via the reductive pathway using glutamine carbon rather than glucose. Using ISA to model the contribution of each tracer to lipogenic AcCoA, we observed that the reductive carboxylation of glutamine-derived αKG contributed approximately 80% of the carbon for de novo lipogenesis in A549 cells (FIG. 3E). Significant increases in the relative utilization of reductive glutamine metabolism were observed in all tested cell lines under hypoxia, including HCT116, 143B, MDA-MB-231, and H1299s, which exhibited minimal reductive activity under normoxia (FIG. 18). Conversely, we detected a concomitant decrease in the contribution of [U-$^{13}C_6$]glucose to fatty acid synthesis under hypoxia. This switch to glutamine-fueled lipogenesis was also observed to varying extents in non-transformed human cell lines, including MRC5 fetal lung fibroblasts (FIG. 3F) and MCF10A immortalized mammary epithelia (FIG. 18). Importantly, all cells continued to grow under hypoxia, albeit at a slower rate, as indicated by decreases in both proliferation and de novo lipogenesis under hypoxia (FIG. 19). Despite these changes, the contribution of reductive glutamine metabolism to fatty acid synthesis under hypoxia was equal to or greater than that of glucose oxidation for all cells tested. These data demonstrate that proliferating human cells generate cytosolic citrate and AcCoA predominantly through reductive carboxylation when $O_2$ levels are low.

Figure 27A:
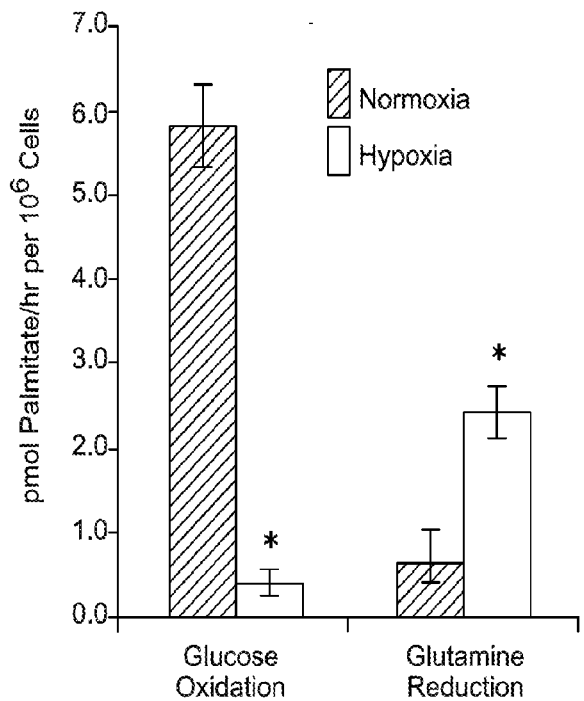
FIG. 27. Hypoxia reprograms cells to rely on reductive carboxylation of glutamine for lipid synthesis. (A) Absolute fluxes of [U-$^{13}$C6]glucose and [5-$^{13}$C]glutamine to palmitate in A549 cells. From left in each set of bars in (A): normoxia (grey bars) and hypoxia (white bars) (B) Cell number of Huh7 cells after 100,000 cells were plated and cultured for 4 days in the presence or absence of glutamine. From left in each set of bars in (B): Gln+ (white bars) and Gln− (grey bars). Error bars indicate s.e.m. (n=3) for (B).  denotes p<0.005 comparing glutamine-free cultures. * denotes p<0.001 comparing normoxia and hypoxia under glutamine-free conditions. Error bars indicate 95% CI from ISA model for A; * denotes p<0.05 comparing normoxia to hypoxia (A).
Figure 27B:
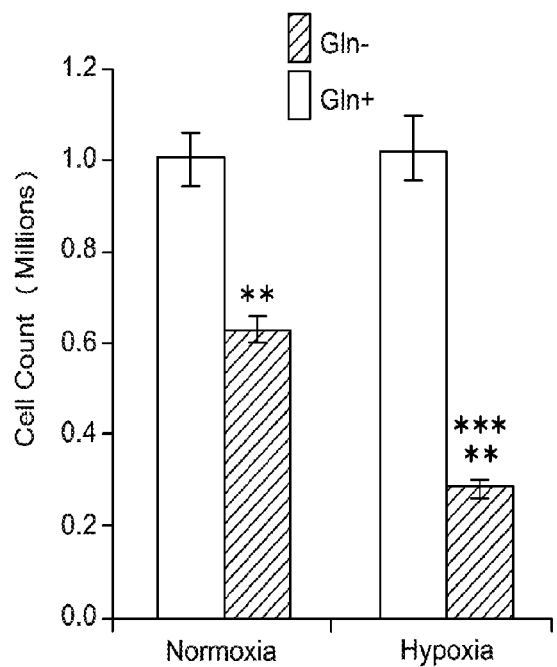
Figure 28A:
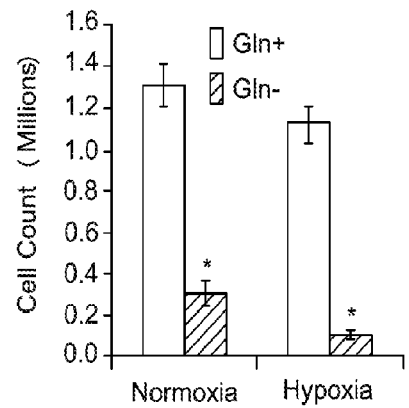
FIG. 28. Net flux of glutamine to palmitate through the reductive pathway increases under hypoxia in cells capable of growing without glutamine. A,B) A549 cells require glutamine for proliferation at normoxia and hypoxia. Cell number (A) and viability (B) data for A549 cells grown for 3 days under normoxia or hypoxia in the presence and absence of glutamine. From left in each set of bars in (A,B): Gln+(white bars) and Gln− (grey bars). Error bars indicate s.e.m., and * denotes p<0.05 comparing +/− glutamine samples. C) Huh7 cells, which can proliferate in the absence of glutamine, were cells were cultured for 4 days in the presence of [5-$^{13}$C]glutamine under normoxia or hypoxia. Cells were extracted and labeling was observed in palmitate methyl esters obtained from the total pool of fatty acids (free fatty acids and biomass). Absolute flux was calculated using the ISA fit parameters, quantifying measured fatty acids with a heptadeconoate internal standard, and dividing by the integral viable cell density. Error bars represent 95% confidence intervals obtained from the ISA fit. Results were reproduced in 3 replicates.
Figure 28B:
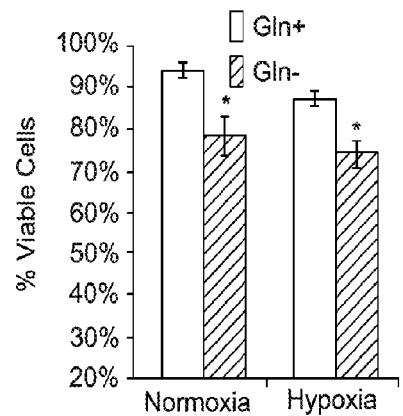
Figure 28C:
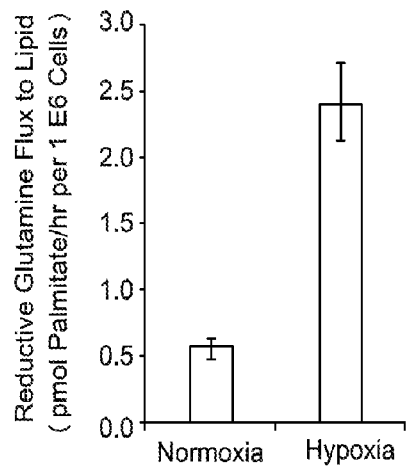

Importantly, the net flux of reductive glutamine metabolism to palmitate synthesis was significantly increased in hypoxic cultures (FIG. 27A). Although mammalian cells require glutamine for nucleotide and hexosamine biosynthesis, some cells can grow in the absence of exogenous sources of glutamine, presumably by synthesizing it de novo25. Remarkably, we found that hypoxia increases the dependence of such cells on glutamine, as evidenced by decreased proliferation in the absence of glutamine and increased reductive glutamine metabolism under hypoxia when glutamine is present (FIGS. 27B, 28).

Figure 4A:
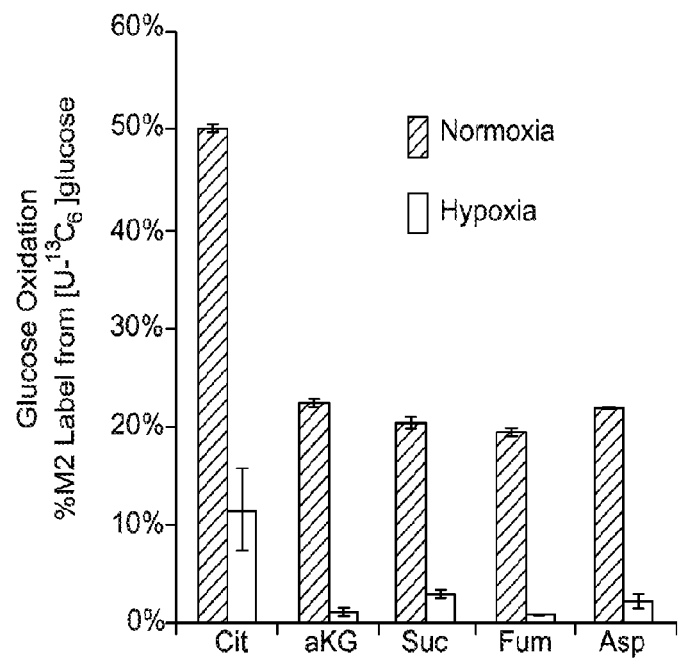
FIG. 4. Reductive TCA metabolism increases under hypoxia. MRC5 cells were cultured under normoxia or hypoxia for 3 days in the presence of tracer. A) Relative level of glucose oxidation as determined by M2 labeling from [U-$^{13}$C$_6$]glucose (see FIG. 20 for atom transition map). B) Relative abundance of citrate/isocitrate (cannot be differentiated by GC/MS). C) Relative flux of glutamine carbon into the TCA cycle. D) Generation of TCA metabolites from glutamine via reductive carboxylation. Grey bars indicate normoxia and white bars indicate hypoxia. Error bars indicate s.e.m. (n=3).
Figure 4B:
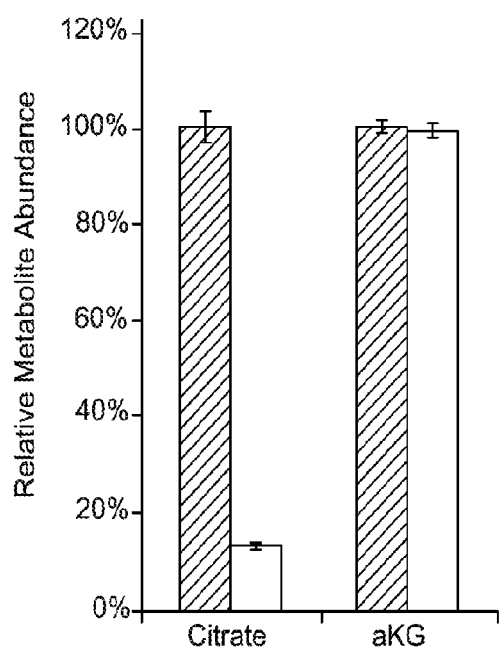
Figure 4C:
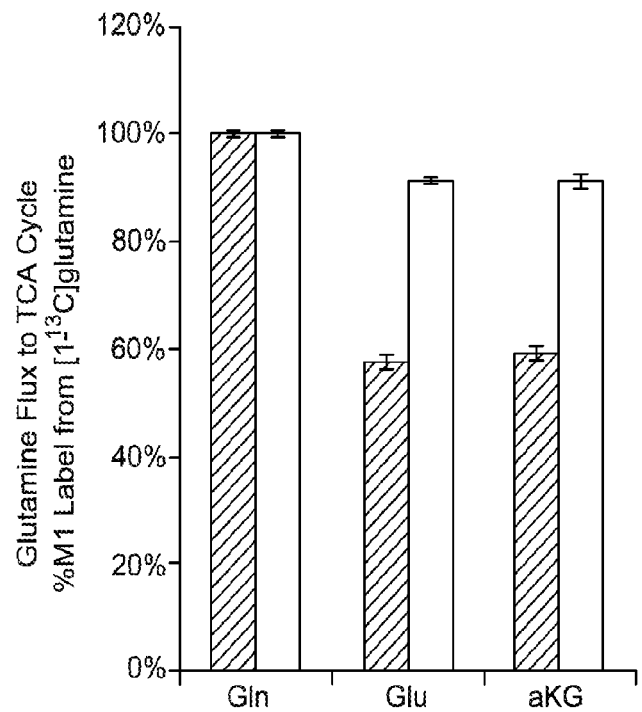
Figure 4D:
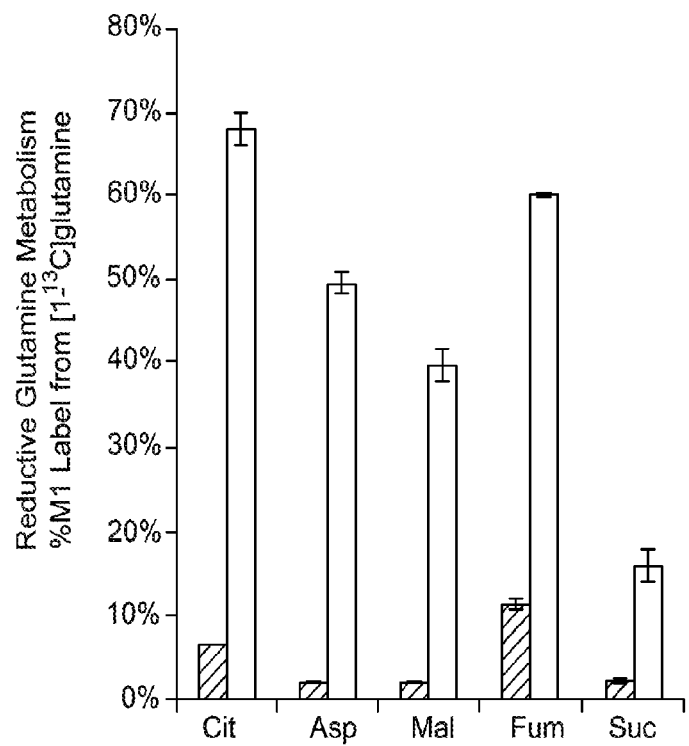
Figure 20C:
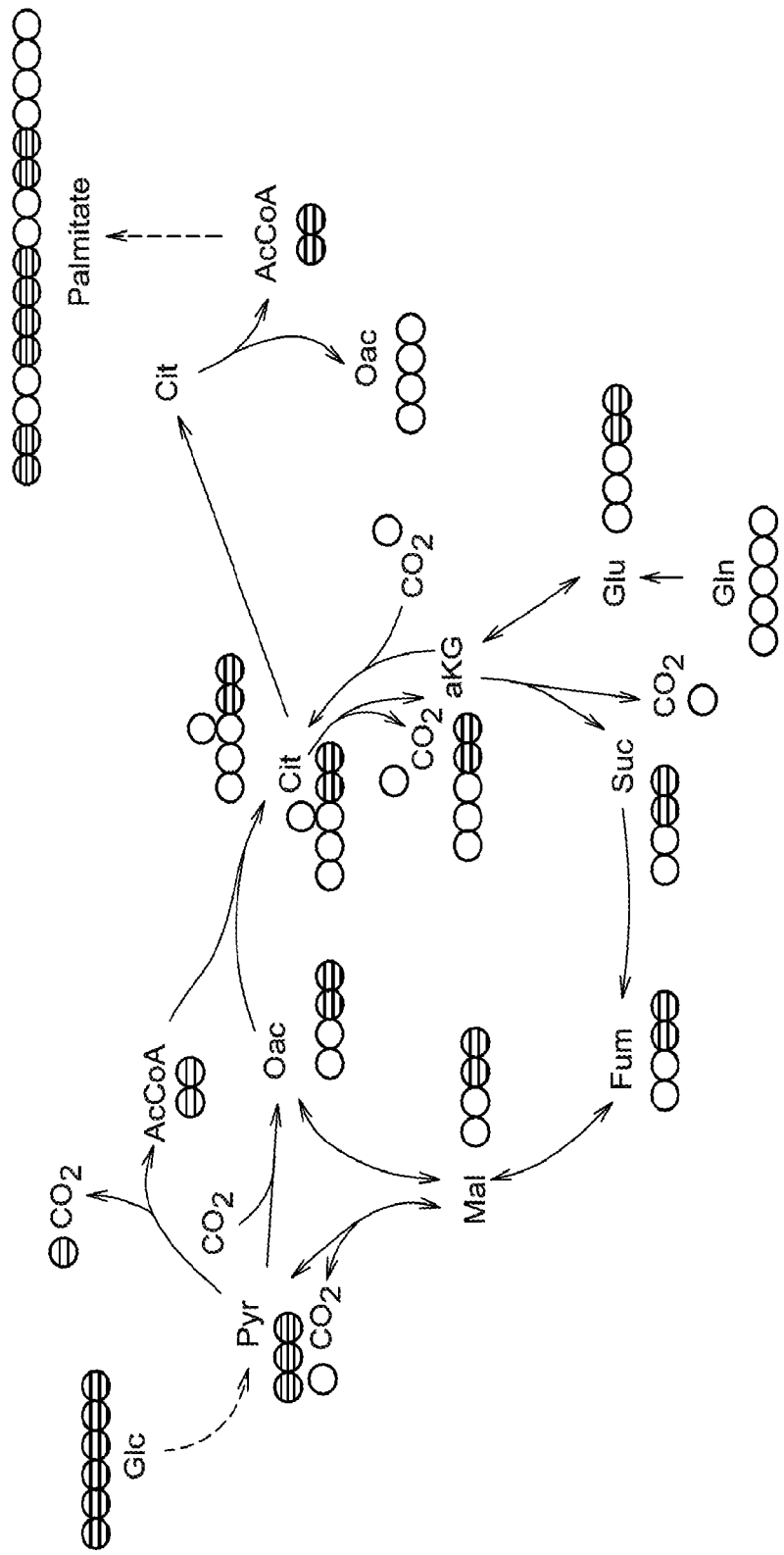
FIG. 20. Hypoxia affects citrate levels and flux through PDH. A) Relative citrate levels decrease significantly in A549 cells cultured under hypoxia while aKG levels remain unchanged. Sum integration of all potentially labeled ions is shown, with abundances normalized to cell number and internal standard signal. B) Transfer of label from [U-$^{13}$C$_6$] glucose oxidation to TCA cycle metabolites in A549 cells cultured under normoxia and hypoxia indicates a relative decrease in PDH flux. Error bars indicate s.e.m. (n=3). C) Atom transition map depicting oxidation of [U-$^{13}$C$_6$]glucose. M2 labeled TCA cycle metabolites (or aspartate) arise from PDH activity (red), generating dually labeled AcCoA that enters the TCA cycle. Although some recycling occurs, the most abundant isotopologues observed using [U-$^{13}$C$_6$] glucose were M2, as anaplerosis of unlabeled carbons from glutamine/glutamine is significant in cultured cells. D) Reductive carboxylation specific isotopomers from [U-$^{13}$C$_5$] glutamine are elevated under hypoxia. From left in each set of bars: normoxia (grey bars), hypoxia (white bars). Error bars indicate s.e.m. (n=3).

To gain insight into the metabolic mechanisms of this phenomenon we analyzed changes in the labeling and abundances of TCA cycle metabolites in MRC5 and A549 cells grown under hypoxia. In particular, we observed a significant decrease in the transfer of glucose carbons to the TCA cycle under hypoxia, indicating decreased activity of the pyruvate dehydrogenase (PDH) complex (FIGS. 4A, 20). In addition, the citrate/isocitrate pool became depleted, conditions which would be expected to increase reductive carboxylation flux (FIGS. 4B, 20). In some cases these decreases prevented us from obtaining accurate measurements of citrate labeling under hypoxia. In contrast to our results with [U-$^{13}C_6$]glucose, we detected increased amounts of isotopic label in TCA cycle intermediates when using glutamine tracers under hypoxia (FIG. 4C, 4D, 20). Ultimately, reductively metabolized glutamine accounted for as much as 40-70% of the intracellular citrate, aspartate, malate, and fumarate pools in these culture conditions (FIG. 4D). These data highlight the metabolic changes which occur upon prolonged growth under hypoxia, as cells reductively metabolize amino acids to generate citrate and AcCoA.

Example 4

Figure 5A:
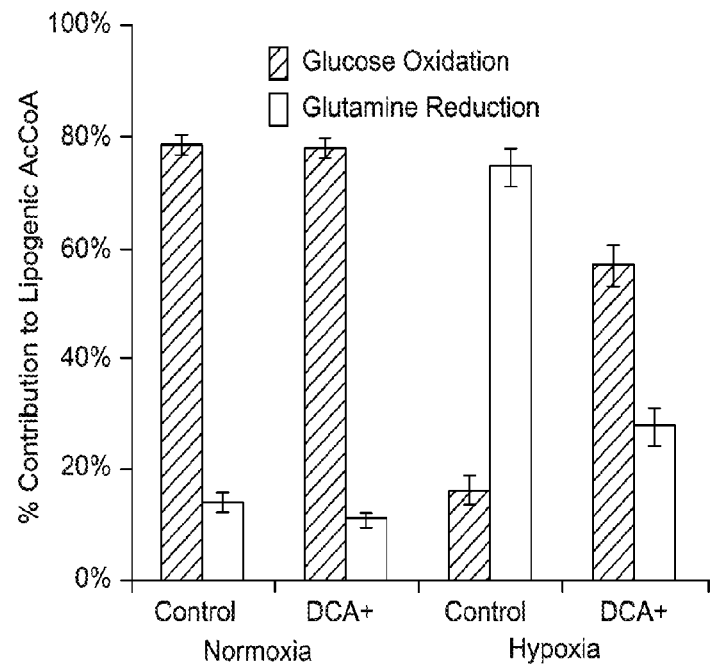
FIG. 5. The HIF/ARNT/VHL signaling axis regulates carbon utilization. A) Contribution of glucose oxidation and glutamine reduction to lipogenesis in A549 cells cultured under normoxia/hypoxia with or without 5 mM DCA. Grey bars indicate glucose oxidation and white bars indicate glutamine reduction. B) Relative level of glucose oxidation in cells in (A). White bars indicate normoxia control, white striped bars indicate normoxia with DCA, grey bars indicate hypoxia control and grey striped bars indicate hypoxia with DCA. C-E) Contribution of glucose oxidation and glutamine reduction to lipogenesis in RCC lines (C), parental control (PRC3) and VHL+ (WT8) cells derived from 786-O line (36) (D), or vector control (pTV) or HIF2α shRNA (pTR) cells derived from 786-O line (42) (E). Grey bars indicate glucose oxidation and white bars indicate glutamine reduction. F) Relative level of glucose oxidation for cells in (D) and (E). From left in each set of bars: WT8 (VHL+), PRC3 (VHL−), pTR (HIF2a kd), and pTV (ctrl). G) HIF2α levels for cells in (C-E). H) Pathway contributions to lipogenesis in UMRC2 cells expressing ARNT-targeting shRNAs. Grey bars indicate glucose oxidation and white bars indicate glutamine reduction. I) Glucose oxidation in control and ARNT knockdown cells. From left in each set of bars: control (blue/darker grey), ARNT kd (red/lighter grey). Error bars indicate 95% confidence intervals for lipid ISA measurements and s.e.m. for glucose labeling (n=3).
Figure 5B:
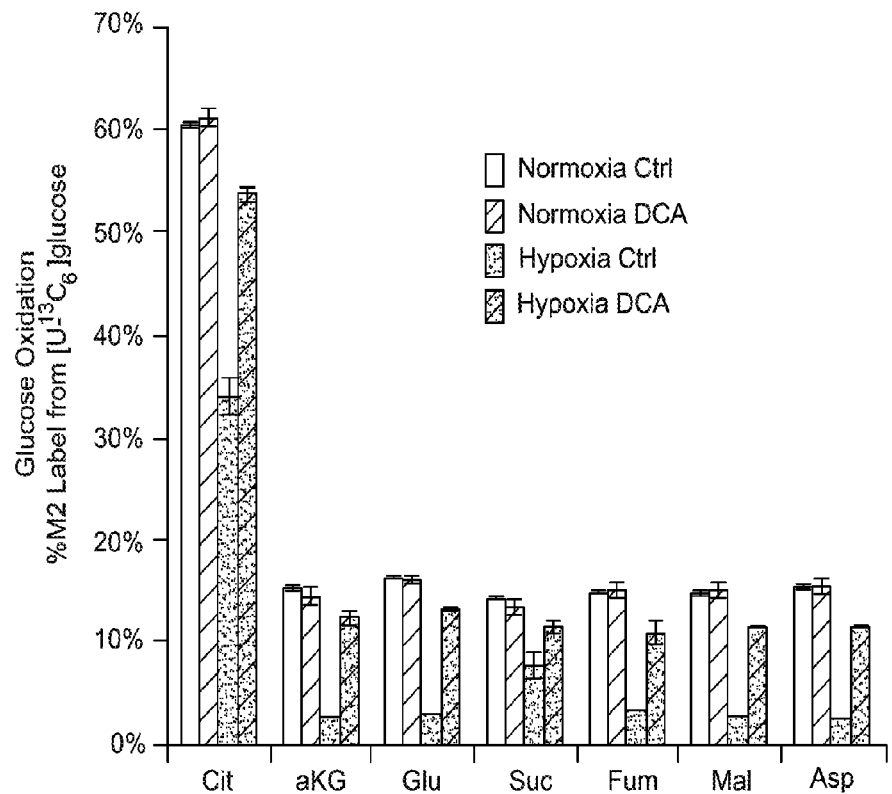

Loss of the VHL Tumor Suppressor Drives the Switch to Reductive Glutamine Metabolism Given the marked reduction in PDH activity observed under hypoxia, we tested the ability of dichloroacetate (DCA) to mitigate the contribution of reductive metabolism to lipogenesis. DCA inhibits PDK1, a known target of HIF-1α and the cellular response to hypoxia that inhibits the activity of PDH through phosphorylation (16, 17, 34). While DCA treatment had no observable effect on carbon utilization under normoxia, reductive glutamine metabolism was inhibited and glucose oxidation was partially restored in A549 cells cultured with DCA under hypoxia (FIGS. 5A, 5B), suggesting that PDK1 inhibition downstream of HIF signaling contributes to the use of reductive carboxylation for fatty acid synthesis.

Figure 5C:
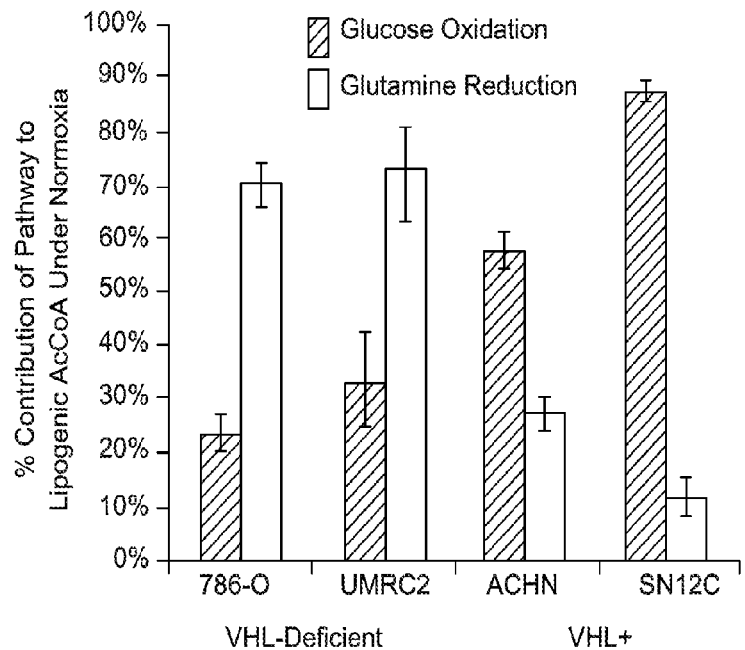
Figure 5D:
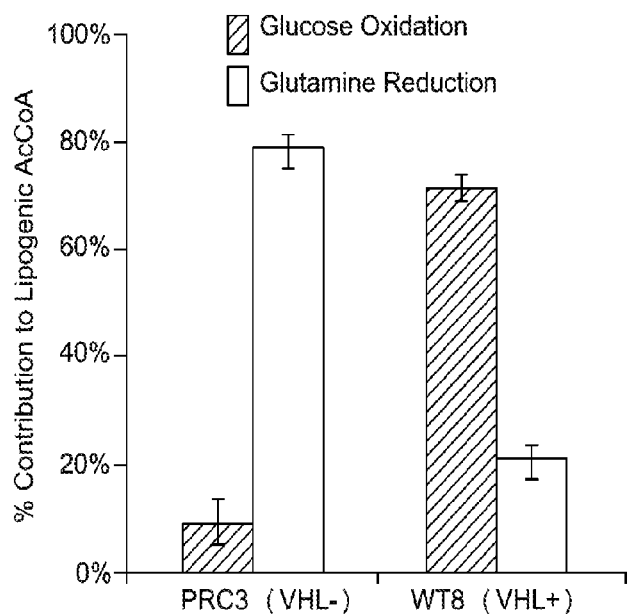
Figure 5I:
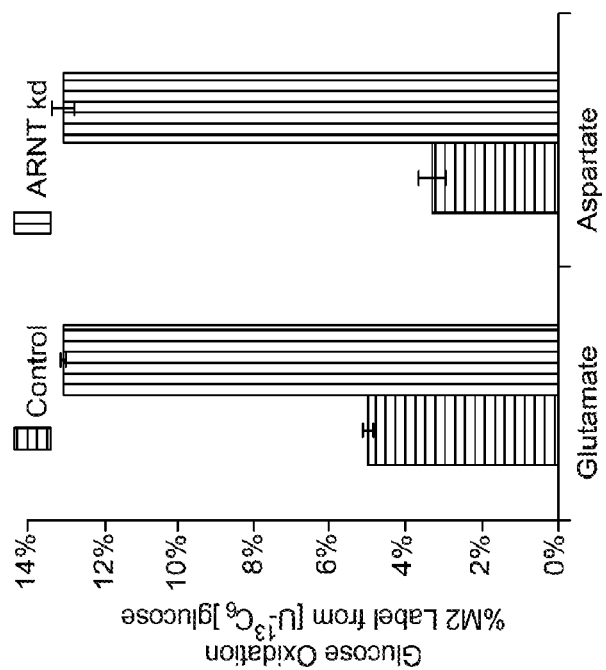
Figure 5H:
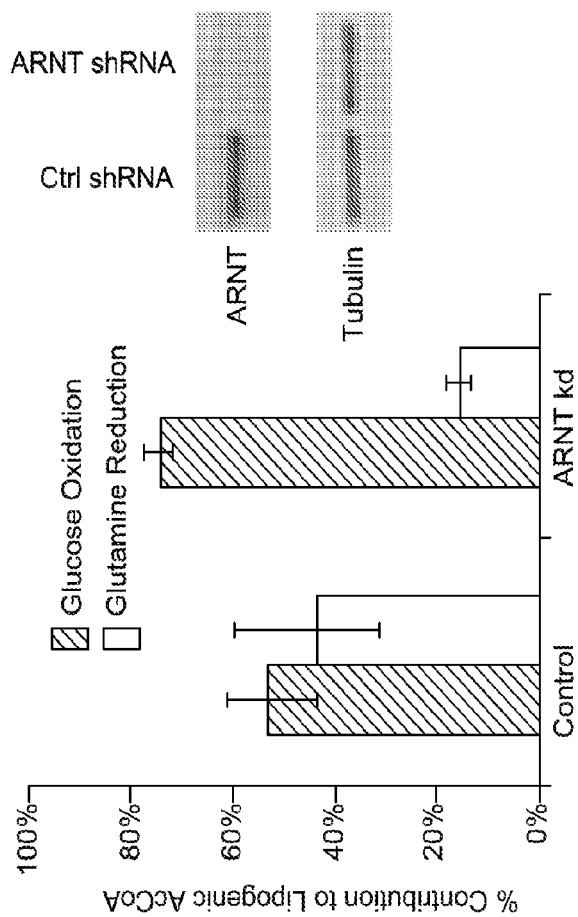
Figure 21A:
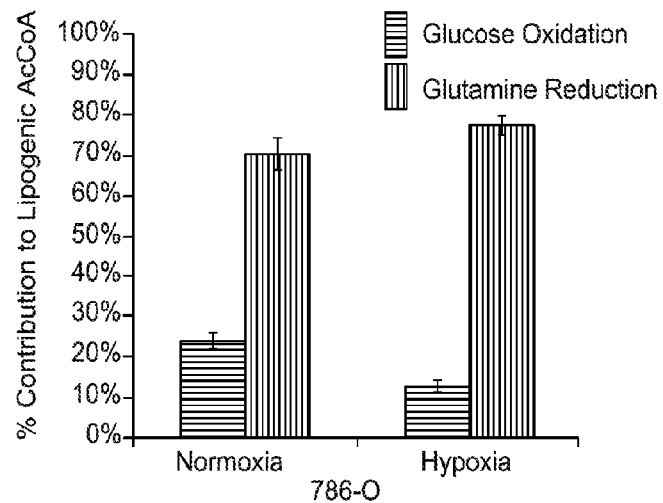
FIG. 21. ISA of lipogenesis in renal clear cell carcinoma (RCC) cell lines under normoxia and hypoxia. A) VHL-deficient 786-O cells slightly increase the utilization of reductive glutamine metabolism for lipogenesis under hypoxia, as this pathway is used at high levels even under normoxia. B,C) RCC cell lines that express wild-type VHL behave normally, preferentially using glucose oxidation under normoxia and reductive carboxylation under hypoxia. From left in each set of bars: glucose oxidation (blue/dark grey bars), glutamine reduction (red/light grey bars). Error bars indicate 95% confidence intervals from ISA model.
Figure 21B:
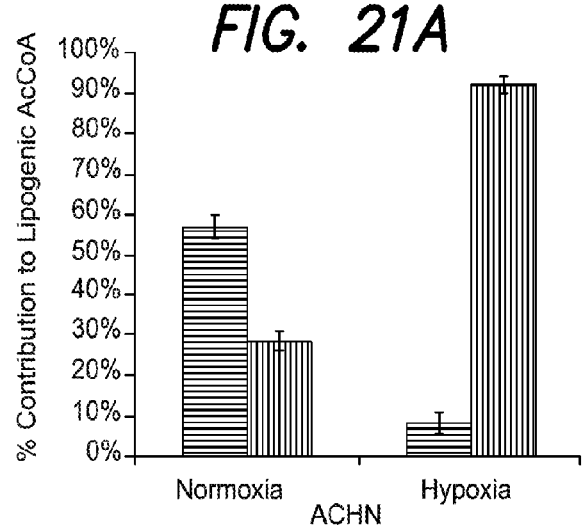
Figure 21C:
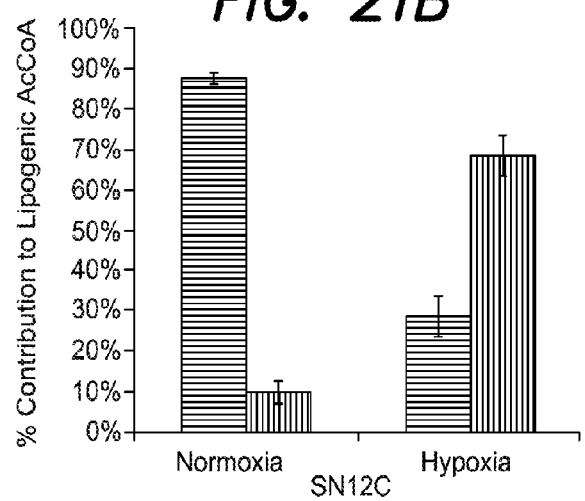
Figure 22A:
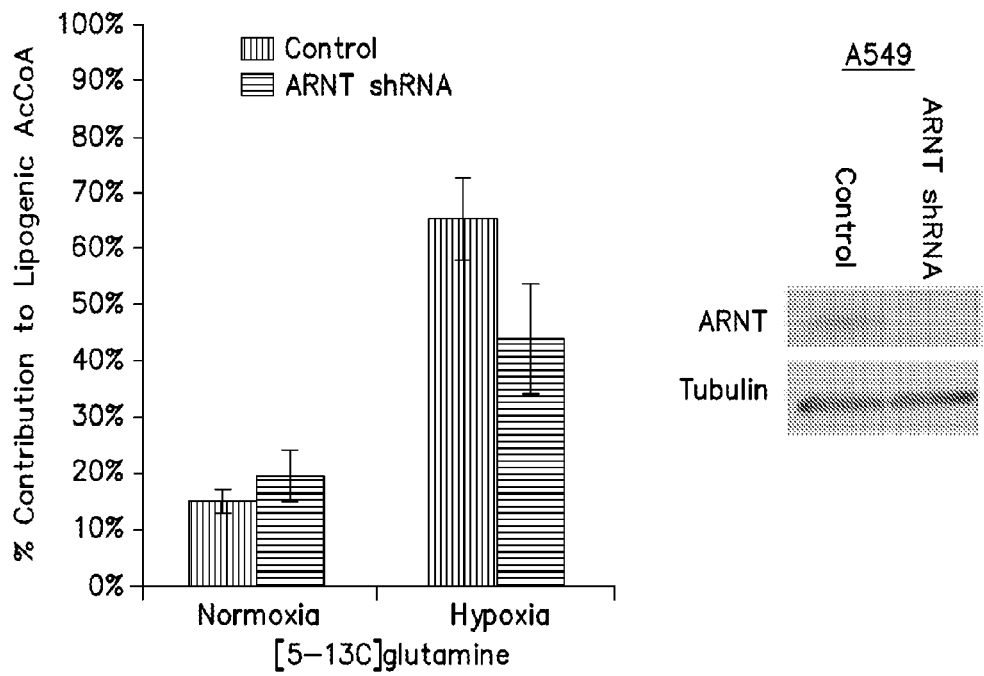
FIG. 22. ISA of lipogenesis using [5-$^{13}$C]glutamine with A549 (A) and 143B (B) cells expressing shRNAs targeting ARNT. From left in each set of bars: control (red/light grey bars), ARNT shRNA (blue/dark grey bars). Error bars indicate 95% confidence intervals from ISA model.
Figure 22B:
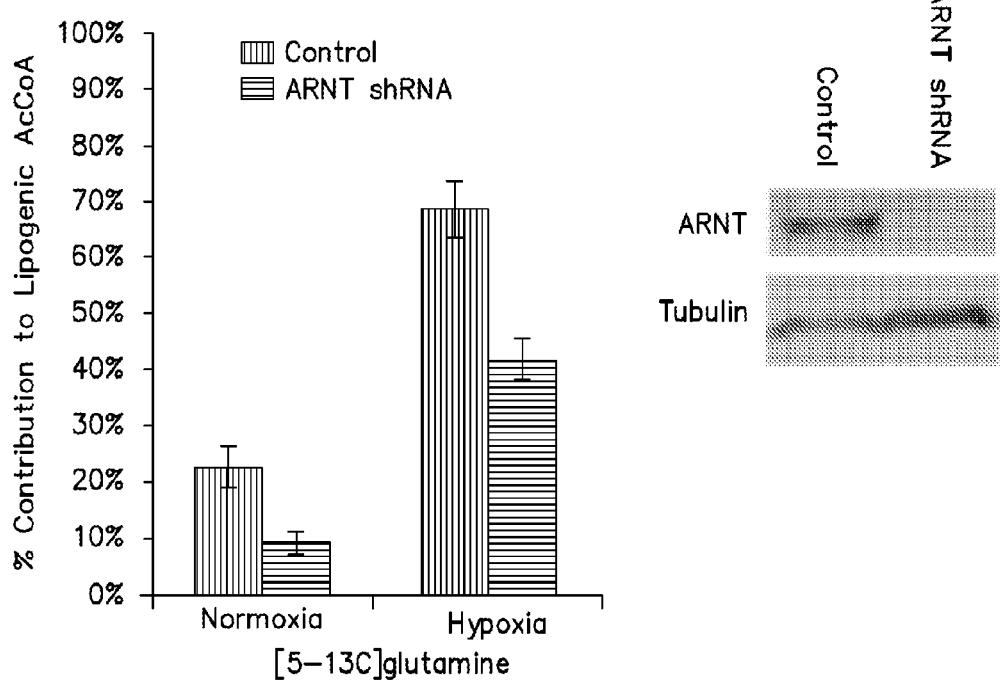
Figure 30B:
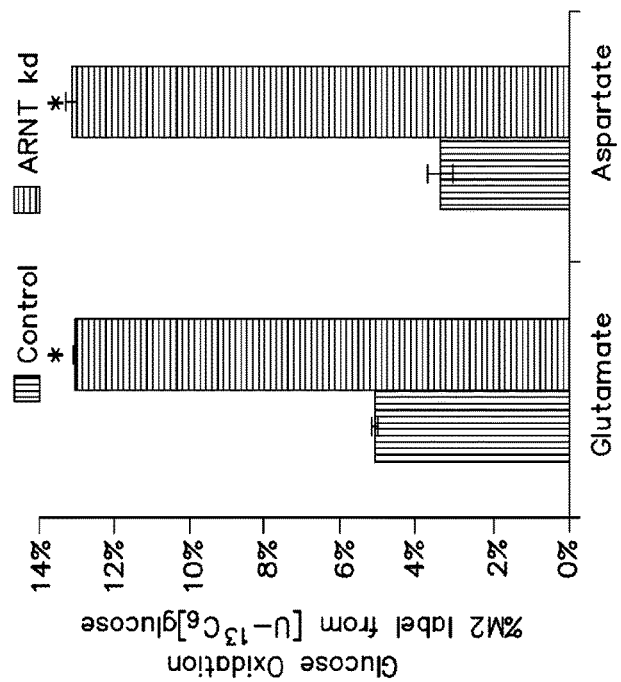
FIG. 30. ARNT knockdown modulates glucose oxidation and reductive glutamine metabolism. A) ISA of lipogenesis in UMRC2 cells expressing control or ARNT-targeting shRNAs. From left in each set of bars in (A): Glucose oxidation (grey bars) and Glutamin reduction (white bars). B) Relative glucose oxidation in cells in (A), as measured by M2 labeling from [U-$^{13}$C6]glucose. From left in each set of bars in (B): Control (dark grey bars) and ARNT kd (light grey bars). Error bars indicate s.e.m. (n=3). * indicates p<0.05 comparing control to knockdown.
Figure 30A:
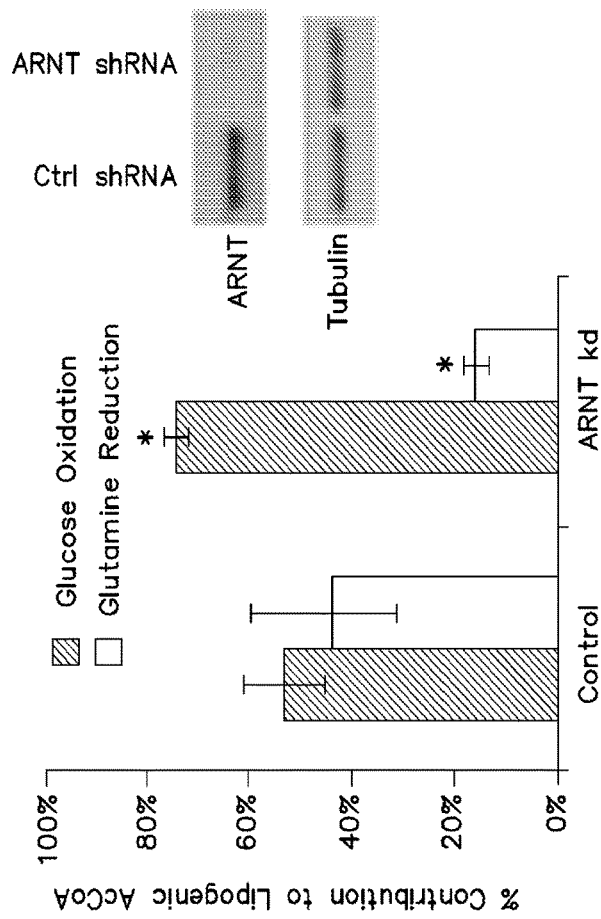

To understand the role of this pathway in driving the switch to reductive lipogenesis we tested renal clear cell carcinoma (RCC) cells deficient in VHL using ISA. RCCs are often defective in the VHL tumor suppressor and exhibit "pseudohypoxia," as HIFα subunits are not degraded in the presence of $O_2$ (35). Remarkably, renal cell lines lacking functional VHL protein, but not those expressing wild-type (WT) VHL, preferentially utilized glutamine for lipogenesis via reductive metabolism under normal culture conditions (FIG. 5C). While VHL-deficient 786-O cells increased their use of reductive carboxylation under hypoxia only slightly, RCC lines expressing WT VHL behaved similarly to previously analyzed cells (FIG. 21). This "normoxic" utilization of reductive metabolism was dependent upon the absence of VHL, as expression of WT VHL in isogenic cells caused them to regain the ability to oxidize glucose for lipid synthesis (FIG. 5D). Re-expression of WT VHL in previously VHL-deficient cell lines resulted in reduced extracellular fluxes of glucose, lactate, and glutamine (FIG. 29A), and increased the pool of intracellular citrate relative to αKG (FIG. 29B) under normoxia. Furthermore, shRNA-mediated knockdown of HIF-2α was able to partially restore glucose-mediated lipogenesis in 786-O cells (FIG. 5E). Consistent with our observations under hypoxia, VHL-deficient cells did not oxidize glucose into the TCA cycle, as we were unable to detect significant quantities of label in glutamate or aspartate pools after 3 days of culture with $[U-^{13}C_6]$glucose (FIG. 5F). However, comparative analysis of VHL+ WT8 or pTR HIF-2α shRNA cells demonstrated that glucose oxidation could be restored in the parental line by perturbing the hypoxic signaling axis (FIG. 5F). Consistent with VHL and HIF influencing the switch to reductive glutamine metabolism during hypoxia, glucose entry into the TCA cycle via PDH was increased under normoxia upon introduction of WT VHL or knockdown of HIF-2α in 786-O cells (FIG. 23C). Additionally, a similar response was observed by knocking down the HIFα dimerization partner ARNT (aryl hydrocarbon receptor nuclear translocator) in VHL-deficient UMRC2 cells (FIG. 5G, 5H), which express both HIF-1α and HIF-2α (36), or following ARNT knock down in hypoxic A549 and 143B cells (FIG. 30). Similarly, expression of ARNT-targeting shRNAs in A549 and 143B cells reduced the utilization of $[5-^{13}C]$glutamine for lipogenesis (FIG. 22). Together, these data implicate the VHL/ARNT/HIF signaling axis in driving cells to utilize reductive glutamine metabolism for fatty acid biosynthesis.

Summary

We have demonstrated that IDH1 catalyzes the reductive conversion of αKG to isocitrate in human cells. Under conditions of hypoxia or VHL-deficiency this pathway is the primary route through which cells generate lipogenic AcCoA, highlighting an important role for reductive carboxylation in cells proliferating under low $O_2$ conditions. Given the almost exclusive use of reductive carboxylation for lipogenesis under hypoxia, a redundant or contributing role of IDH2 in this pathway is probable under such conditions. However, our data provide evidence that the reductive pathway involves IDH1-mediated catalysis in the cytoplasm.

While the carbon source that cells use for lipid synthesis appears to be determined, in part, by HIF-mediated regulation of PDK1, additional hypoxia-associated changes may also promote reductive glutamine metabolism. For example, HIF-2α enhances c-MYC activity (37), which in turn drives glutamine catabolism through the regulation of numerous genes (38). It is intriguing to note that VHL and HIF-2α are associated with tumor progression in a number of tumor types (35, 39), and reintroduction of VHL protein into deficient renal cell lines suppresses their ability to form tumors in nude mice (35). When accounting for the relative rate of de novo lipogenesis, tumor cell lines exhibited an enhanced activity of reductive glutamine metabolism under hypoxia compared to non-transformed cells, suggesting that this metabolic switch may be important for tumor growth when $O_2$ levels are low or VHL is lost (FIGS. 3, 5D, 18, 19). While more extensive studies are required to elucidate the individual and potentially cell-specific contributions of each player along the HIF/ARNT/VHL signaling pathway to this metabolic phenomenon, tumor cells with inactivating mutations in enzymes catalyzing oxidative glutaminolysis (e.g. succinate dehydrogenase, fumarate hydratase) that induce pseudohypoxia and tumorigenesis may also rely on reductive glutamine metabolism for lipid synthesis (40). It is also possible that reductive metabolism in hypoxic, normal, lipogenic cells, such as adipocytes or hepatocytes, contributes to metabolic disease.

Figure 6B:
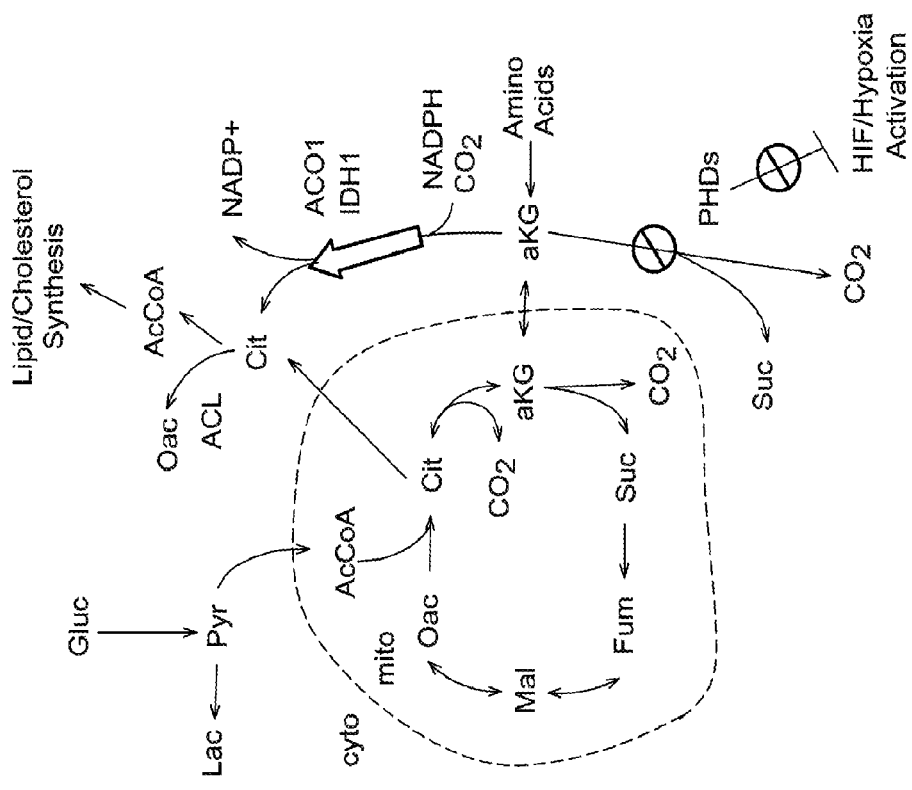
FIG. 6. Metabolic maps depicting the conventional view of central carbon metabolism and a new characterization of IDH1 function and αKG/citrate metabolism under hypoxia. A) The citrate shuttle (red) is thought to be fueled primarily by glucose carbon and represent the main source of cytosolic acetyl coenzyme A (AcCoA), which is generated from citrate via ATP-citrate lyase (ACL). The current understanding of ACO1 and IDH1 activity in mammalian cells involves the conversion of citrate to αKG and generation of NADPH for reductive biosynthesis. αKG in the cytosol takes part in transamination reactions (not shown) or is converted to succinate via αKG-dependent oxygenases such as prolyl hydroxylases (PHDs). B) Our results demonstrate that IDH1 catalyzes the reductive carboxylation of αKG, generating isocitrate and consuming NADPH (red). Under hypoxia, αKG-dependent oxygenases are inhibited and cellular metabolism is reconfigured such that the reductive IDH reaction becomes the primary source of cytosolic AcCoA (red). Amino acids fuel the supply of αKG in the cytosol, and glucose-derived pyruvate is diverted to lactate (blue). Both IDH1 and IDH2 (mitochondrial) presumably operate in reverse to maintain the supply of lipogenic carbon required for growth in hypoxic tumors. For simplicity, some exchange reactions are omitted.
Figure 6A:
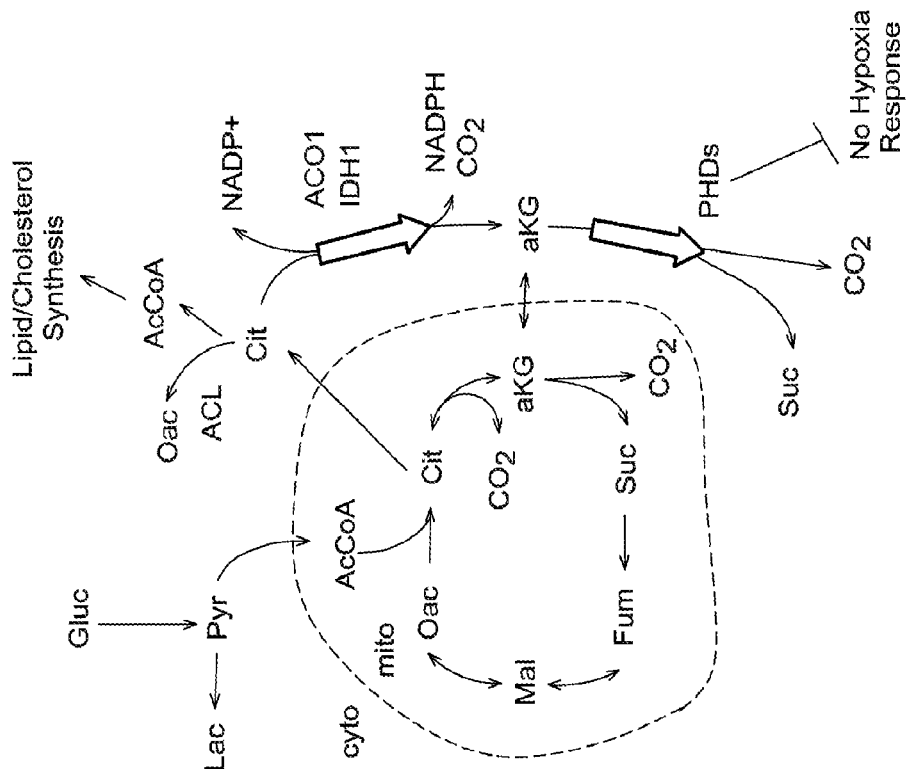
Figure 23:
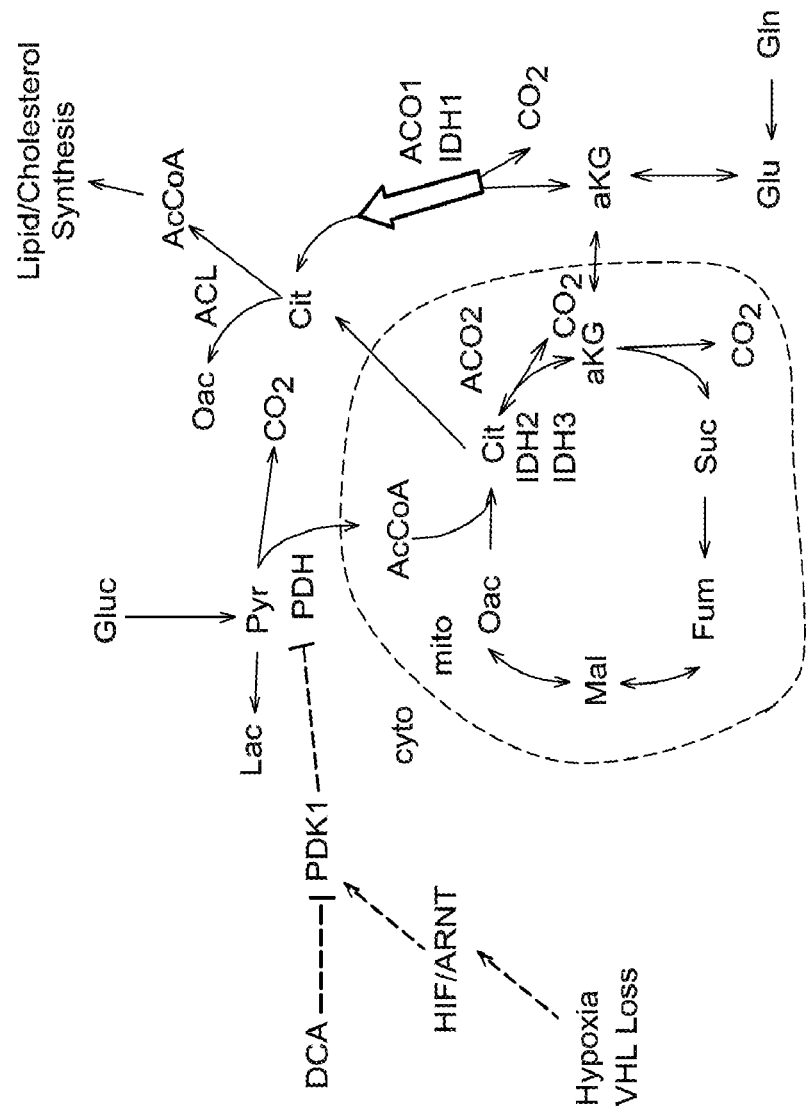
FIG. 23. Mechanism through which hypoxia and/or VHL loss reprograms carbon utilization. Low oxygen environment or deficiency in the VHL protein causes stabilization of HIFα proteins. HIFa subunits interact with ARNT to mediate the hypoxic gene response, including the induction of pyruvate dehydrogenase kinase 1 (PDK1), which encodes a protein that inhibits pyruvate dehydrogenase (PDH) complex activity via phosphorylation. PDH activity under hypoxia or VHL loss decreases in part through HIF-mediated transcription of PDK1, and consequently, intracellular levels of citrate and isocitrate become depleted. These changes can be reversed by culturing cells under hypoxia in the presence of dichloroacetate (DCA), a chemical inhibitor of PDK1. The metabolic network compensates for decreased production of glucose-derived citrate and AcCoA by increasing the reductive metabolism of glutamine-derived aKG. As a result, reductive glutamine metabolism is the primary source of lipogenic citrate and AcCoA in hypoxic cells.

We have identified that the cellular response to hypoxia involves the increased reductive metabolism of glutamine (FIG. 6B, 23). This metabolic reprogramming provides an effective, glucose-independent means of generating AcCoA for biosynthesis. In hypoxic microenvironments glucose is also likely to be limited, and cells must conserve glucose carbon for synthesizing ribose and other glycolytic intermediates necessary for amino acid and nucleic acid biosynthesis (e.g. serine and glycine) (41). On the other hand, necrotic tumor regions may be rich in proteins and amino acids, which could be converted to AcCoA and αKG and subsequently metabolized via reductive carboxylation to synthesize lipids. Thus, hypoxic reprogramming of reductive metabolism may allow cells to more efficiently distribute available nutrients in such microenvironments. In addition, our findings solve a fundamental paradox of the Warburg effect and hypoxic cell growth. That is, how do tumor cells support fatty acid biosynthesis when much of the glucose carbon is fermented to lactate? We demonstrate that cells employ reductive metabolism of glutamine for this purpose rather than oxidative glutaminolysis. These results add a new dimension to our understanding of cell metabolism, generating potential targets along the reductive carboxylation pathway that could mitigate hypoxic tumor growth.

REFERENCES

1. G. Hatzivassiliou et al., *Cancer Cell* 8, 311 (2005).
2. K. E. Wellen et al., *Science* 324, 1076 (2009).
3. T. Migita et al., *Cancer Res* 68, 8547 (2008).
4. R. J. DeBerardinis et al., *Proc Natl Acad Sci USA* 104, 19345 (2007).
5. D. R. Wise et al., *Proc Natl Acad Sci USA* 105, 18782 (2008).
6. C. Des Rosiers et al., *J Biol Chem* 270, 10027 (1995).
7. H. Yoo, M. R. Antoniewicz, G. Stephanopoulos, J. K. Kelleher, *J Biol Chem* 283, 20621 (2008).
8. G. Siebert, M. Carsiotis, G. W. Plaut, *J Biol Chem* 226, 977 (1957).
9. A. F. D'Adamo, Jr., K. D. Tobin, *Life Sci* 24, 2011 (1979).
10. K. L. Olszewski et al., *Nature* 466, 774 (2010).
11. G. L. Semenza, *Curr Opin Genet Dev* 20, 51 (2010).
12. J. Pouyssegur, F. Dayan, N. M. Mazure, *Nature* 441, 437 (2006).

13. M. M. Hickey, M. C. Simon, *Curr Top Dev Biol* 76, 217 (2006).
14. M. Ivan et al., *Science* 292, 464 (2001).
15. P. Jaakkola et al., *Science* 292, 468 (2001).
16. J. W. Kim, I. Tchernyshyov, G. L. Semenza, C. V. Dang, *Cell Metab* 3, 177 (2006).
17. I. Papandreou, R. A. Cairns, L. Fontana, A. L. Lim, N. C. Denko, *Cell Metab* 3, 187 (2006).
18. J. D. Gordan, C. B. Thompson, M. C. Simon, *Cancer Cell* 12, 108 (2007).
19. M. K. Hellerstein, *Metab Eng* 6, 85 (2004).
20. U. Sauer, *Mol Syst Biol* 2, 62 (2006).
21. L. G. Boros et al., *Blood* 102, 3556 (2003).
22. W. N. Lee et al., *Am J Physiol* 274, E843 (1998).
23. J. Munger et al., *Nat Biotechnol* 26, 1179 (2008).
24. J. D. Young, J. L. Walther, M. R. Antoniewicz, H. Yoo, G. Stephanopoulos, *Biotechnol Bioeng* 99, 686 (2008).
25. K. Maier, U. Hofmann, M. Reuss, K. Mauch, *Biotechnol Bioeng* 100, 355 (2008).
26. C. M. Metallo, J. L. Walther, G. Stephanopoulos, *J Biotechnol* 144, 167 (2009).
27. P. S. Ward et al., *Cancer Cell* 17, 225 (2010).
28. J. M. Lemons et al., *PLoS Biol* 8, e1000514 (2010).
29. M. K. Hellerstein, R. A. Neese, *Am J Physiol* 263, E988 (1992).
30. A. T. Kharroubi, T. M. Masterson, T. A. Aldaghlas, K. A. Kennedy, J. K. Kelleher, *Am J Physiol* 263, E667 (1992).
31. D. T. Hartong et al., *Nat Genet* 40, 1230 (2008).
32. S. Zhao et al., *Science* 324, 261 (2009).
33. F. Weinberg et al., *Proc Natl Acad Sci USA* 107, 8788 (2010).
34. S. Bonnet et al., *Cancer Cell* 11, 37 (2007).
35. W. G. Kaelin, Jr., *Nat Rev Cancer* 2, 673 (2002).
36. M. Zimmer et al., *Mol Cell* 32, 838 (2008).
37. J. D. Gordan, J. A. Bertout, C. J. Hu, J. A. Diehl, M. C. Simon, *Cancer Cell* 11, 335 (2007).
38. C. V. Dang, *Cell Cycle* 8, 3243 (2009).
39. G. Qing, M. C. Simon, *Curr Opin Genet Dev* 19, 60 (2009).
40. J. P. Bayley, P. Devilee, *Curr Opin Genet Dev* 20, 324 (2010).
41. R. M. Sutherland, *Science* 240, 177 (1988).
42. M. Zimmer, D. Doucette, N. Siddiqui, O. Iliopoulos, *Mol Cancer Res* 2, 89 (2004).
43. O. Iliopoulos, A. Kibel, S. Gray, W. G. Kaelin, Jr., *Nat Med* 1, 822 (1995).
44. D. D. Sarbassov, D. A. Guertin, S. M. Ali, D. M. Sabatini, *Science* 307, 1098 (2005).
45. C. A. Fernandez, C. Des Rosiers, S. F. Previs, F. David, H. Brunengraber, *J Mass Spectrom* 31, 255 (1996).
46. M. R. Antoniewicz, J. K. Kelleher, G. Stephanopoulos, *Metab Eng* 8, 324 (2006).
47. M. R. Antoniewicz, J. K. Kelleher, G. Stephanopoulos, *Metab Eng* 9, 68 (2007).
48. Y. Noguchi et al., *J Biol Chem* 284, 33425 (2009).
49. M. Safran et al., *Proc Natl Acad Sci USA* 103, 105 (2006).
50. E. L. Bell, T. A. Klimova, J. Eisenbart, P. T. Schumacker, N. S. Chandel, *Mol Cell Biol* 27, 5737 (2007).
51. J. C. Chatham, B. Bouchard, C. Des Rosiers, *Mol Cell Biochem* 249, 105 (2003).
52. P. Vizan et al., *Cancer Res* 65, 5512 (2005).

TABLE 1

GC/MS metabolites and fragments used for isotope quantification

| Metabolite | Carbons | Formula | m/z range |
|---|---|---|---|
| αKG | 12345 | C14H28O5NSi2 | 346-355 |
| Ala | 23 | C10H26ONSi2 | 232-239 |
| Ala | 123 | C11H26O2NSi2 | 260-268 |
| Asp | 12 | C14H32O2NSi2 | 302-310 |
| Asp | 1234 | C18H40O4NSi3 | 418-428 |
| Cit | 123456 | C20H39O6Si3 | 459-470 |
| Cit | 123456 | C26H55O7Si4 | 591-602 |
| Fum | 1234 | C12H23O4Si2 | 287-297 |
| Gln | 12345 | C19H43N2O3Si3 | 431-441 |
| Glu | 2345 | C16H36O2NSi2 | 330-340 |
| Glu | 12345 | C19H42O4NSi3 | 432-442 |
| Mal | 1234 | C18H39O5Si3 | 419-428 |
| Lac | 23 | C10H25O2Si2 | 233-240 |
| Lac | 123 | C11H25O3Si2 | 261-269 |
| Pyr | 123 | C6H12O3NSi | 174-182 |
| Suc | 1234 | C12H25O4Si2 | 289-298 |
| Palmitate | 1-16 | C17H34O2 | 270-276 |
| Stearate | 1-18 | C19H38O2 | 298-316 |

TABLE 2

Network and carbon atom transitions describing central carbon metabolism for MFA. Suffixes indicate localization to a specific compartment: .x, extracellular; .c, cytosolic; .m, mitochondrial; .d, dilution; .mnt, measurement. Dilution and measurement compartments do not partake in central metabolism. Metabolites lacking a suffix are assumed to be equilibrated between compartments. → indicates net flux: ($v_F$-$v_R$); ←→ indicates exchange flux: min($v_F$, $v_R$).

Glycolysis

Glc.x (abcdef) → G6P (abcdef)
G6P (abcdef) ←→ F6P (abcdef)
F6P (abcdef) → DHAP (cba) + GAP(def)
DHAP (abc) ←→ GAP (abc)
GAP (abc) ←→ 3PG (abc)
3PG (abc) → Pyr.c (abc)
Pyr.c (abc) ←→ Lac (abc)
Lac (abc) → Lac.x (abc)
Pentose Phosphate Pathway G6P (abcdef) → P5P (bcdef) + CO2 (a)
P5P (abcde) + P5P (fghij) ←→ S7P (abfghij) + GAP (cde)
S7P (abcdefg) + GAP (hij) ←→ F6P (abchij) + E4P (defg)
P5P (abcde) + E4P (fghi) ←→ F6P (abfghi) + GAP (cde)
Anaplerotic Fluxes Pyr.m (abc) + CO2 (d) → Oac (abcd)
Mal (abcd) ←→ Pyr.m (abc) + CO2 (d)
Glu (abcde) ←→ Akg (abcde)
Oac (abcd) ←→ Asp (abcd)
TCA cycle Pyr.m (abc) → AcCoA.m (bc) + CO2 (a)
AcCoA.m (ab) + Oac (cdef) → Cit (fedbac)
Cit (abcdef) ←→ Akg (abcde) + CO2 (f)
Akg (abcde) → Suc (bcde) + CO2 (a)
Suc (abcd) ←→ Fum (abcd)
Fum (abcd) ←→ Mal (abcd)
Mal (abcd) ←→ Oac (abcd)
Amino acids Pyr.m (abc) ←→ Ala (abc)
Gln.x (abcde) → Gln (abcde)
Gln (abcde) → Glu (abcde)
Glu (abcde) → Glu.x (abcde)
Biomass production Cit (abcdef) → AcCoA.c (ed) + Oac (fcba)
AcCoA.c (ab) → Fatty acids (ab)
0.6 Asp + 0.5 Glu + 0.42 Ala + 0.5 Gln → Biomass
P5P (abcde) → NTP (abcde)

TABLE 2-continued

Network and carbon atom transitions describing central carbon metabolism for MFA. Suffixes indicate localization to a specific compartment: .x, extracellular; .c, cytosolic; .m, mitochondrial; .d, dilution; .mnt, measurement. Dilution and measurement compartments do not partake in central metabolism. Metabolites lacking a suffix are assumed to be equilibrated between compartments. → indicates net flux: ($v_F$-$v_R$); ←→ indicates exchange flux: min($v_F$, $v_R$).

Dilution and Mixing Fluxes

Suc.d (abcd) → Suc.mnt (abcd)
0 Suc (abcd) → Suc.mnt (abcd)
Pyr.c (abc) ←→ Pyr.m (abc)
0 Pyr.c (abc) → Pyr.mnt (abc)
0 Pyr.m (abc) → Pyr.mnt (abc)

TABLE 3

Estimated fluxes for A549 cells expressing non-targeting control shRNAs

| Pathway/Reaction | Flux fmol/cell*hr | 95% confidence interval Lower bound | Upper bound |
|---|---|---|---|
| Glycolysis | | | |
| Glc.x -> G6P | 98.23 | 87.81 | 108.90 |
| G6P -> F6P | 90.22 | 79.77 | 100.90 |
| G6P <-> F6P | 648.20 | 0.00 | Inf |
| F6P -> DHAP + GAP | 95.23 | 84.80 | 106.00 |
| DHAP -> GAP | 95.23 | 84.80 | 106.00 |
| DHAP <-> GAP | 168.90 | 0.00 | Inf |
| GAP -> 3PG | 193.00 | 172.10 | 214.50 |
| GAP <-> 3PG | 497.60 | 0.00 | Inf |
| 3PG -> Pyr.c | 193.00 | 172.10 | 214.50 |
| Pyr.c -> Lac | 183.90 | 163.10 | 205.50 |
| Pyr.c <-> Lac | 3.0E+03 | 0.00 | Inf |
| Lac -> Lac.x | 183.90 | 163.10 | 205.50 |
| Pentose Phosphate Pathway | | | |
| G6P -> P5P + CO2 | 8.00 | 6.43 | 9.57 |
| P5P + P5P -> S7P + GAP | 2.50 | 2.18 | 2.83 |
| P5P + P5P <-> S7P + GAP | 4.1E+08 | 0.00 | Inf |
| S7P + GAP -> F6P + E4P | 2.50 | 2.18 | 2.83 |
| S7P + GAP <-> F6P + E4P | 283.60 | 0.00 | Inf |
| P5P + E4P -> F6P + GAP | 2.50 | 2.18 | 2.83 |
| P5P + E4P <-> F6P + GAP | 397.50 | 0.00 | Inf |
| Anaplerotic reactions | | | |
| Pyr.m + CO2 -> Oac | 0.00 | 0.00 | 0.27 |
| Mal -> Pyr.m + CO2 | 4.42 | 3.75 | 5.06 |
| Mal <-> Pyr.m + CO2 | 1.52 | 0.99 | 1.60 |
| Glu -> Akg | 5.04 | 4.76 | 5.48 |
| Glu <-> Akg | 477.60 | 198.40 | Inf |
| Oac -> Asp | 0.62 | 0.50 | 0.73 |
| Oac <-> Asp | 942.60 | 0.00 | Inf |
| TCA Cycle | | | |
| Pyr.m -> AcCoA.m + CO2 | 13.01 | 12.22 | 13.90 |
| AcCoA.m + Oac -> Cit | 13.01 | 12.22 | 13.90 |
| Cit -> Akg + CO2 | 3.52 | 3.35 | 3.69 |
| Cit <-> Akg + CO2 | 2.93 | 2.80 | 3.07 |
| Akg -> Suc + CO2 | 8.56 | 8.29 | 8.91 |
| Suc -> Fum | 8.56 | 8.29 | 8.91 |
| Suc <-> Fum | 0.00 | 0.00 | 1.61 |
| Fum -> Mal | 8.56 | 8.29 | 8.91 |
| Fum <-> Mal | 9.9E+05 | 311.30 | Inf |
| Mal -> Oac | 4.14 | 3.86 | 4.36 |
| Mal <-> Oac | 134.60 | 64.70 | 1768.00 |

TABLE 3-continued

Estimated fluxes for A549 cells expressing non-targeting control shRNAs

| Pathway/Reaction | Flux fmol/cell*hr | 95% confidence interval Lower bound | Upper bound |
|---|---|---|---|
| Amino acids | | | |
| Pyr.m -> Ala | 0.43 | 0.35 | 0.51 |
| Pyr.m <-> Ala | 0.03 | 0.00 | Inf |
| Gln.x -> Gln | 19.68 | 18.49 | 21.19 |
| Gln -> Glu | 19.16 | 18.03 | 20.70 |
| Glu -> Glu.x | 13.61 | 11.90 | 15.27 |
| Biomass | | | |
| Cit -> AcCoA.c + Oac | 9.49 | 8.88 | 10.03 |
| AcCoA.c -> Fatty acids | 9.49 | 8.88 | 10.03 |
| 0.6*Asp + 0.5*Glu + 0.42*Ala + 0.5*Gln -> Biomass | 1.03 | 0.84 | 1.22 |
| P5P -> NTP | 0.50 | 0.40 | 0.60 |
| Dilution/Mixing | | | |
| Suc.d -> Suc.mnt | 0.55 | 0.53 | 0.56 |
| 0*Suc -> Suc.mnt | 0.45 | 0.44 | 0.47 |
| Pyr.c -> Pyr.m | 9.02 | 8.15 | 9.79 |
| Pyr.c <-> Pyr.m | 98.59 | 70.22 | 140.20 |
| 0*Pyr.c -> Pyr.mnt | 1.00 | 0.84 | 1.00 |
| 0*Pyr.m -> Pyr.mnt | 0.00 | 0.00 | 0.16 |

SSE = 83.6
Expected SSE = [72.5 127.3] (95% conf., 98 DOF)

TABLE 4

Estimated fluxes for A549 cells expressing IDH1-targeting shRNAs (IDH1a)

| Pathway/Reaction | Flux fmol/cell*hr | 95% confidence interval Lower bound | Upper bound |
|---|---|---|---|
| Glycolysis | | | |
| Glc.x -> G6P | 94.96 | 82.80 | 107.10 |
| G6P -> F6P | 86.95 | 74.71 | 99.19 |
| G6P <-> F6P | 3.2E+04 | 0.00 | Inf |
| F6P -> DHAP + GAP | 91.96 | 79.79 | 104.10 |
| DHAP -> GAP | 91.96 | 79.79 | 104.10 |
| DHAP <-> GAP | 566.90 | 0.00 | Inf |
| GAP -> 3PG | 186.40 | 162.10 | 210.80 |
| GAP <-> 3PG | 1.7E+08 | 0.00 | Inf |
| 3PG -> Pyr.c | 186.40 | 162.10 | 210.80 |
| Pyr.c -> Lac | 174.60 | 149.90 | 199.30 |
| Pyr.c <-> Lac | 706.50 | 0.00 | Inf |
| Lac -> Lac.x | 174.60 | 149.90 | 199.30 |
| Pentose Phosphate Pathway | | | |
| G6P -> P5P + CO2 | 8.01 | 6.45 | 9.58 |
| P5P + P5P -> S7P + GAP | 2.50 | 1.98 | 3.03 |
| P5P + P5P <-> S7P + GAP | 3.0E+04 | 0.00 | Inf |
| S7P + GAP -> F6P + E4P | 2.50 | 1.98 | 3.03 |
| S7P + GAP <-> F6P + E4P | 1.9E+05 | 0.00 | Inf |
| P5P + E4P -> F6P + GAP | 2.50 | 1.98 | 3.03 |
| P5P + E4P <-> F6P + GAP | 1.76 | 0.00 | Inf |
| Anaplerotic reactions | | | |
| Pyr.m + CO2 -> Oac | 2.14 | 0.52 | 2.57 |
| Mal -> Pyr.m + CO2 | 5.44 | 3.47 | 7.22 |
| Mal <-> Pyr.m + CO2 | 0.00 | 0.00 | 1.69 |
| Glu -> Akg | 3.90 | 2.59 | 5.28 |

TABLE 4-continued

Estimated fluxes for A549 cells expressing IDH1-targeting shRNAs (IDH1a)

| Pathway/Reaction | Flux fmol/cell*hr | 95% confidence interval Lower bound | Upper bound |
|---|---|---|---|
| Glu <-> Akg | 499.30 | 145.90 | Inf |
| Oac -> Asp | 0.61 | 0.49 | 0.72 |
| Oac <-> Asp | 0.01 | 0.00 | Inf |
| TCA Cycle | | | |
| Pyr.m -> AcCoA.m + CO2 | 14.66 | 13.30 | 16.02 |
| AcCoA.m + Oac -> Cit | 14.66 | 13.30 | 16.02 |
| Cit -> Akg + CO2 | 4.01 | 3.38 | 4.67 |
| Cit <-> Akg + CO2 | 1.88 | 1.50 | 2.34 |
| Akg -> Suc + CO2 | 7.91 | 6.48 | 9.41 |
| Suc -> Fum | 7.91 | 6.48 | 9.41 |
| Suc <-> Fum | 0.00 | 0.00 | 4.32 |
| Fum -> Mal | 7.91 | 6.48 | 9.41 |
| Fum <-> Mal | 1.1E+06 | 46.26 | Inf |
| Mal -> Oac | 2.48 | 1.82 | 3.32 |
| Mal <-> Oac | 98.66 | 41.31 | Inf |
| Amino acids | | | |
| Pyr.m -> Ala | 0.42 | 0.34 | 0.50 |
| Pyr.m <-> Ala | 0.00 | 0.00 | Inf |
| Gln.x -> Gln | 23.47 | 20.64 | 26.29 |
| Gln -> Glu | 22.97 | 20.44 | 25.78 |
| Glu -> Glu.x | 18.56 | 15.70 | 21.42 |
| Biomass | | | |
| Cit -> AcCoA.c + Oac | 10.65 | 9.48 | 11.84 |
| AcCoA.c -> Fatty acids | 10.65 | 9.48 | 11.84 |
| 0.6*Asp + 0.5*Glu + 0.42*Ala + 0.5*Gln -> Biomass | 1.01 | 0.81 | 1.20 |
| P5P -> NTP | 0.50 | 0.40 | 0.60 |
| Dilution/Mixing | | | |
| Suc.d -> Suc.mnt | 0.76 | 0.74 | 0.78 |
| 0*Suc -> Suc.mnt | 0.24 | 0.22 | 0.26 |
| Pyr.c -> Pyr.m | 11.79 | 9.98 | 13.61 |
| Pyr.c <-> Pyr.m | 82.77 | 42.18 | 154.10 |
| 0*Pyr.c -> Pyr.mnt | 1.00 | 0.68 | 1.00 |
| 0*Pyr.m -> Pyr.mnt | 0.00 | 0.00 | 0.32 |

SSE = 93.4
Expected SSE = [58.0 107.8] (95% conf., 81 DOF)

TABLE 5

Estimated fluxes for A549 cells expressing IDH1-targeting shRNAs (IDH1b)

| Pathway/Reaction | Flux fmol/cell*hr | 95% confidence interval Lower bound | Upper bound |
|---|---|---|---|
| Glycolysis | | | |
| Glc.x -> G6P | 110.60 | 95.97 | 125.50 |
| G6P -> F6P | 102.60 | 87.90 | 117.60 |
| G6P <-> F6P | 0.00 | 0.00 | Inf |
| F6P -> DHAP + GAP | 107.60 | 92.96 | 122.50 |
| DHAP -> GAP | 107.60 | 92.96 | 122.50 |
| DHAP <-> GAP | 550.40 | 0.00 | Inf |
| GAP -> 3PG | 217.80 | 188.40 | 247.50 |
| GAP <-> 3PG | 160.00 | 0.00 | Inf |
| 3PG -> Pyr.c | 217.80 | 188.40 | 247.50 |
| Pyr.c -> Lac | 204.60 | 175.20 | 234.30 |
| Pyr.c <-> Lac | 695.70 | 0.00 | Inf |
| Lac -> Lac.x | 204.60 | 175.20 | 234.30 |
| Pentose Phosphate Pathway | | | |
| G6P -> P5P + CO2 | 8.01 | 6.45 | 9.57 |
| P5P + P5P -> S7P + GAP | 2.50 | 1.99 | 3.02 |
| P5P + P5P <-> S7P + GAP | 6.3E+07 | 0.00 | Inf |
| S7P + GAP -> F6P + E4P | 2.50 | 1.99 | 3.02 |
| S7P + GAP <-> F6P + E4P | 1.1E+06 | 0.00 | Inf |
| P5P + E4P -> F6P + GAP | 2.50 | 1.99 | 3.02 |
| P5P + E4P <-> F6P + GAP | 1.9E+06 | 0.00 | Inf |
| Anaplerotic reactions | | | |
| Pyr.m + CO2 -> Oac | 0.00 | 0.00 | 1.30 |
| Mal -> Pyr.m + CO2 | 3.56 | 2.40 | 5.03 |
| Mal <-> Pyr.m + CO2 | 1.64 | 0.27 | 1.81 |
| Glu -> Akg | 4.16 | 3.36 | 5.04 |
| Glu <-> Akg | 442.50 | 216.10 | 7234.00 |
| Oac -> Asp | 0.60 | 0.48 | 0.71 |
| Oac <-> Asp | 372.30 | 0.00 | Inf |
| TCA Cycle | | | |
| Pyr.m -> AcCoA.m + CO2 | 16.33 | 15.07 | 17.43 |
| AcCoA.m + Oac -> Cit | 16.33 | 15.07 | 17.43 |
| Cit -> Akg + CO2 | 5.05 | 4.43 | 5.69 |
| Cit <-> Akg + CO2 | 2.39 | 2.06 | 2.63 |
| Akg -> Suc + CO2 | 9.21 | 8.33 | 10.21 |
| Suc -> Fum | 9.21 | 8.33 | 10.21 |
| Suc <-> Fum | 0.29 | 0.00 | 1.74 |
| Fum -> Mal | 9.21 | 8.33 | 10.21 |
| Fum <-> Mal | 1.6E+07 | 310.60 | Inf |
| Mal -> Oac | 5.65 | 4.31 | 6.30 |
| Mal <-> Oac | 124.70 | 55.82 | Inf |
| Amino acids | | | |
| Pyr.m -> Ala | 0.42 | 0.34 | 0.50 |
| Pyr.m <-> Ala | 0.00 | 0.00 | Inf |
| Gln.x -> Gln | 25.06 | 22.28 | 27.84 |
| Gln -> Glu | 24.57 | 21.78 | 27.33 |
| Glu -> Glu.x | 19.91 | 16.95 | 22.85 |
| Biomass | | | |
| Cit -> AcCoA.c + Oac | 11.28 | 10.40 | 12.17 |
| AcCoA.c -> Fatty acids | 11.28 | 10.40 | 12.17 |
| 0.6*Asp + 0.5*Glu + 0.42*Ala + 0.5*Gln -> Biomass | 1.00 | 0.80 | 1.19 |
| P5P -> NTP | 0.50 | 0.40 | 0.60 |
| Dilution/Mixing | | | |
| Suc.d -> Suc.mnt | 0.15 | 0.13 | 0.17 |
| 0*Suc -> Suc.mnt | 0.85 | 0.83 | 0.87 |
| Pyr.c -> Pyr.m | 13.19 | 11.76 | 14.42 |
| Pyr.c <-> Pyr.m | 49.63 | 30.59 | 75.51 |
| 0*Pyr.c -> Pyr.mnt | 0.82 | 0.66 | 0.98 |
| 0*Pyr.m -> Pyr.mnt | 0.18 | 0.02 | 0.34 |

SSE = 107.4
Expected SSE = [72.5 127.3] (95% conf., 98 DOF)

TABLE 6

Simplified network for Isotopomer Spectral Analysis

% Enrichment of AcCoA (D parameter)

| | |
|---|---|
| Ac.l (ab) → Ac (ab) | (AcCoA containing tracer label) |
| Ac.d (ab) → Ac (ab) | (unlabeled AcCoA) |
| 8*Ac (ab) → Palm.s (abababababababab) | |

TABLE 6-continued

Simplified network for Isotopomer Spectral Analysis de novo lipogenesis (g(t) parameter)

| | |
|---|---|
| Palm.s → Palm | Newly synthesized palmitate |
| Palm.d → Palm | Pre-existing (unlabeled) palmitate |
| 0*Palm.s + 0*Palm.d → Palm.mnt | Mixing of pools for measurement |

EQUIVALENTS

While several inventive embodiments have been described and illustrated herein, those of ordinary skill in the art will readily envision a variety of other means and/or structures for performing the function and/or obtaining the results and/or one or more of the advantages described herein, and each of such variations and/or modifications is deemed to be within the scope of the inventive embodiments described herein. More generally, those skilled in the art will readily appreciate that all parameters, dimensions, materials, and configurations described herein are meant to be exemplary and that the actual parameters, dimensions, materials, and/or configurations will depend upon the specific application or applications for which the inventive teachings is/are used. Those skilled in the art will recognize, or be able to ascertain using no more than routine experimentation, many equivalents to the specific inventive embodiments described herein. It is, therefore, to be understood that the foregoing embodiments are presented by way of example only and that, within the scope of the appended claims and equivalents thereto, inventive embodiments may be practiced otherwise than as specifically described and claimed. Inventive embodiments of the present disclosure are directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the inventive scope of the present disclosure.

All definitions, as defined and used herein, should be understood to control over dictionary definitions, definitions in documents incorporated by reference, and/or ordinary meanings of the defined terms.

All references, patents and patent applications disclosed herein are incorporated by reference with respect to the subject matter for which each is cited, which in some cases may encompass the entirety of the document.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of." "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

It should also be understood that, unless clearly indicated to the contrary, in any methods claimed herein that include more than one step or act, the order of the steps or acts of the method is not necessarily limited to the order in which the steps or acts of the method are recited.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

We claim:

1. A method for regulating alpha-ketoglutarate (αKG)-dependent oxygenases in a pseudohypoxic cancer or tumor cell comprising contacting the cell with a compound that reduces the activity or expression of isocitrate dehydrogenase 1 (IDH1) or isocitrate dehydrogenase 2 (IDH2) in an amount effective to regulate alpha-ketoglutarate (αKG)-dependent oxygenase activity, wherein the pseudohypoxic cancer or tumor cell is a von Hippel-Lindau (VHL)-deficient carcinoma cell or comprises one or more mutations in succinate dehydrogenase or fumarate hydrogenase.

2. The method of claim 1, wherein the compound that reduces the activity or expression of IDH1 or IDH2 is a small interfering RNA molecule.

3. The method of claim 1, wherein the compound that reduces the activity or expression of IDH1 or IDH2 is a small molecule inhibitor of IDH1 or IDH2.

4. The method of claim 1, wherein the alpha-ketoglutarate (αKG)-dependent oxygenase is a prolyl hydroxylase (PHD) and/or wherein the pseudohypoxic cancer or tumor cell is contacted under hypoxic conditions.

5. The method of claim 3, wherein the compound is oxalomalate or 2-methylisocitrate.

* * * * *